(12) United States Patent
Thomas

(10) Patent No.: US 10,016,793 B2
(45) Date of Patent: Jul. 10, 2018

(54) ENHANCED KNUCKLE-JOINTED LANCE USEFUL FOR INTERNAL CLEANING AND INSPECTION OF TUBULARS

(71) Applicant: Thomas Engineering Solutions & Consulting, LLC, New Iberia, LA (US)

(72) Inventor: William C. Thomas, Lafayette, LA (US)

(73) Assignee: Thomas Engineering Solutions & Consulting, LLC, New Iberia, LA (US)

( * ) Notice: Subject to any disclaimer, the term of this patent is extended or adjusted under 35 U.S.C. 154(b) by 0 days.

(21) Appl. No.: 15/603,332

(22) Filed: May 23, 2017

(65) Prior Publication Data

US 2017/0252783 A1 Sep. 7, 2017

Related U.S. Application Data

(63) Continuation-in-part of application No. 13/833,108, filed on Mar. 15, 2013, now abandoned.
(Continued)

(51) Int. Cl.
*B08B 9/043* (2006.01)
*B08B 9/045* (2006.01)
(Continued)

(52) U.S. Cl.
CPC .......... *B08B 9/0436* (2013.01); *B08B 9/0321* (2013.01); *B08B 9/043* (2013.01);
(Continued)

(58) Field of Classification Search
CPC .......... F28G 1/04; F22B 37/483; B08B 9/032; B08B 9/043; B08B 9/0433; B08B 9/045; E03F 9/005
(Continued)

(56) References Cited

U.S. PATENT DOCUMENTS

D945,971      1/1910  Maslin
1,608,347 A   11/1926 Thompson et al.
(Continued)

FOREIGN PATENT DOCUMENTS

CN    200480012199.4    2/2009

OTHER PUBLICATIONS

International Search Report and the Written Opinion of the International Searching Authority in PCT/US2014/028760 dated Aug. 26, 2014 (11 pages).
(Continued)

*Primary Examiner* — Marc Lorenzi
(74) *Attorney, Agent, or Firm* — Zeman-Mullen & Ford, LLP

(57) ABSTRACT

A Knuckle Jointed Lance (KJL), comprising a segmented lance including a plurality of connected KJL segments in a concatenated string thereof. The first end of one KJL segment is rotatably connected to the second end of a neighboring KJL segment via a pinned connection. Responsive to user assignment of a predetermined length to each KJL segment in the concatenated string according to the KJL segment's corresponding pre-ordained position in the concatenated string, the lance is disposed to spool onto a reel in "nested" fashion, such that as the lance makes spooling revolutions onto the reel, (a) KJL segments stack in circumferential registered layers around the reel and (b) pinned connections trace substantially radial vectors from a center of the reel. Other embodiments provide additional features to facilitate nesting and to generally strengthen the KJL.

11 Claims, 31 Drawing Sheets

Related U.S. Application Data

(60) Provisional application No. 61/707,780, filed on Sep. 28, 2012.

(51) Int. Cl.

| | | |
|---|---|---|
| *B65H 75/38* | (2006.01) | |
| *G01N 29/04* | (2006.01) | |
| *E21B 41/00* | (2006.01) | |
| *B08B 9/032* | (2006.01) | |
| *B65G 47/14* | (2006.01) | |
| *B65G 47/34* | (2006.01) | |
| *E21B 37/00* | (2006.01) | |
| *E21B 19/14* | (2006.01) | |
| *E21B 19/22* | (2006.01) | |
| *G01M 99/00* | (2011.01) | |

(52) U.S. Cl.
CPC .............. *B08B 9/045* (2013.01); *B65G 47/14* (2013.01); *B65G 47/34* (2013.01); *B65H 75/38* (2013.01); *E21B 19/14* (2013.01); *E21B 19/22* (2013.01); *E21B 37/00* (2013.01); *E21B 41/00* (2013.01); *G01N 29/043* (2013.01); *G01M 99/00* (2013.01); *Y10T 74/2186* (2015.01); *Y10T 82/2514* (2015.01); *Y10T 408/381* (2015.01)

(58) Field of Classification Search
USPC ........................................ 134/172; 15/104.33
See application file for complete search history.

(56) References Cited

U.S. PATENT DOCUMENTS

| | | | |
|---|---|---|---|
| 1,923,328 A | | 8/1933 | Reed |
| 2,659,540 A | | 11/1953 | Sketchley |
| 3,492,768 A | | 2/1970 | Schuster |
| 4,508,577 A | | 4/1985 | Conn et al. |
| 4,648,733 A | * | 3/1987 | Merkt ............... F16L 11/18 138/120 |
| 4,771,500 A | | 9/1988 | Kovacs |
| 4,980,120 A | | 12/1990 | Bowman et al. |
| 5,022,463 A | | 6/1991 | Boisture |
| 5,129,455 A | | 7/1992 | Boisture |
| 5,913,320 A | * | 6/1999 | Varrin, Jr. ............ F22B 37/483 122/392 |
| 6,490,748 B1 | | 12/2002 | O'Neill |
| 6,543,392 B1 | | 4/2003 | Ashton, III |
| 6,615,848 B2 | | 9/2003 | Coats |
| 7,263,887 B2 | | 9/2007 | Sfeir et al. |
| 7,401,518 B2 | | 7/2008 | Sfeir et al. |
| 7,530,363 B2 | | 5/2009 | Garman |
| 7,552,640 B2 | | 6/2009 | Sfeir et al. |
| 7,997,138 B2 | | 8/2011 | Sfeir et al. |
| 8,377,231 B2 | | 2/2013 | Richards et al. |
| 8,398,785 B2 | | 3/2013 | Marschall |
| 8,719,989 B1 | | 5/2014 | Qanaei |
| 2002/0092647 A1 | | 7/2002 | Terry |
| 2002/0104471 A1 | | 8/2002 | Awashima et al. |
| 2002/0108644 A1 | * | 8/2002 | Hoadley ................ F23J 3/023 134/172 |
| 2006/0249185 A1 | | 11/2006 | Garman |
| 2007/0039570 A1 | | 2/2007 | Wilfert |
| 2007/0154254 A1 | | 7/2007 | Bevirt |
| 2010/0326481 A1 | | 12/2010 | Buckner |
| 2011/0016940 A1 | | 1/2011 | Poloni et al. |
| 2011/0017021 A1 | | 1/2011 | Minko |
| 2011/0030734 A1 | | 2/2011 | Marschall |
| 2011/0054687 A1 | * | 3/2011 | Buckingham .......... B08B 9/045 700/253 |
| 2011/0155174 A1 | | 6/2011 | Moll et al. |
| 2012/0055521 A1 | * | 3/2012 | Kim ..................... B08B 3/12 134/184 |
| 2013/0019684 A1 | | 1/2013 | Krywyj |

OTHER PUBLICATIONS

Technical Industries, Inc., "Vision Array" marketing brochure, publication date unknown.

English version of claims from Chinese Patent No. 200480012199.4.

Decuir, Perry J., "Optimizing Hydraulic Pressure Using Data Acquisition Systems", proposed IFPE Paper, actual publication date unknown but prior to Feb. 1, 2012.

* cited by examiner

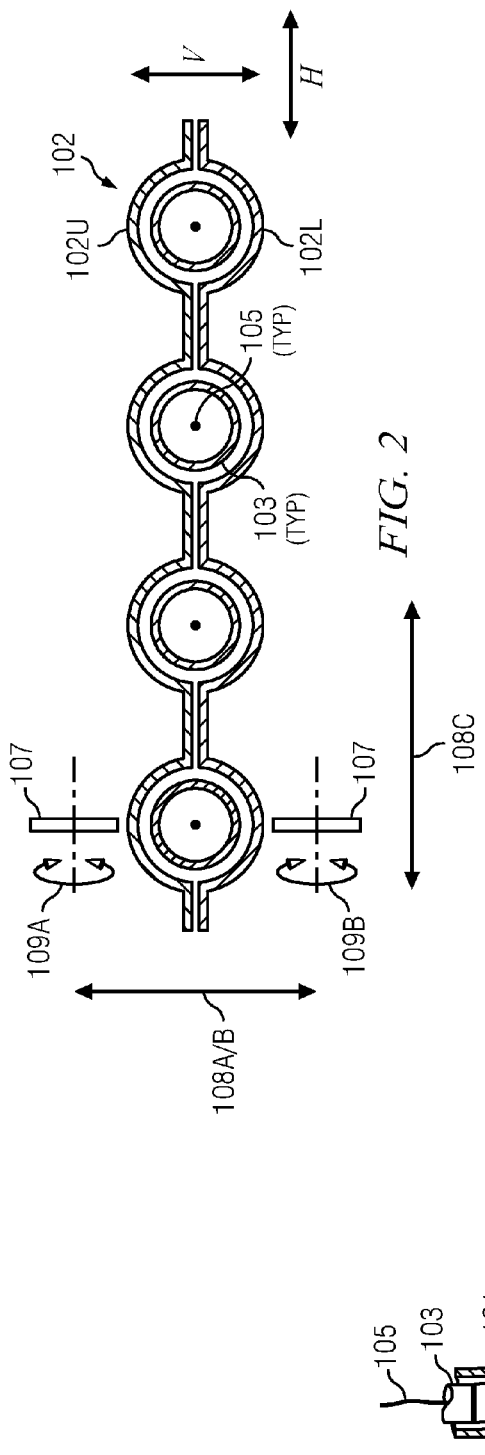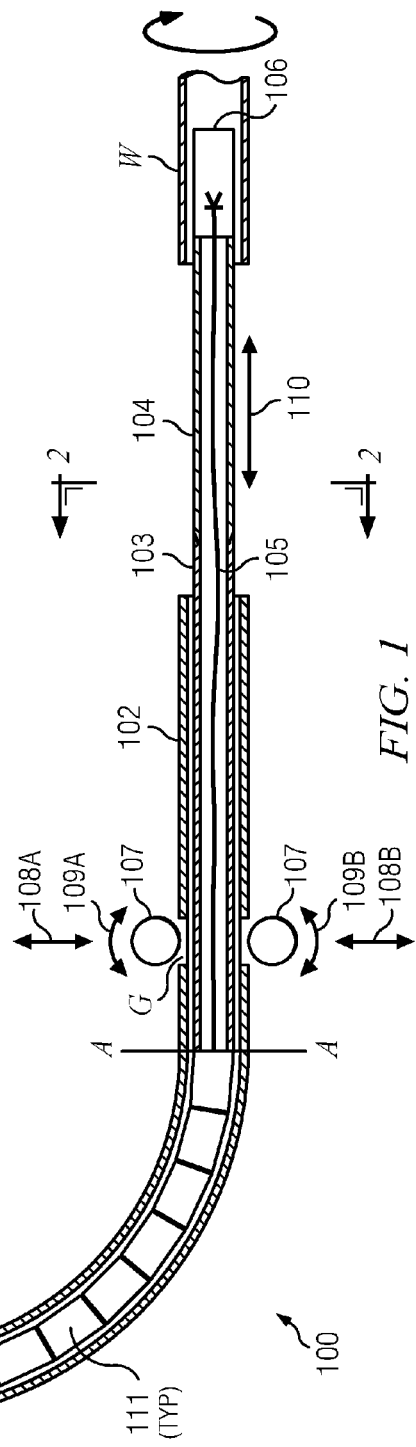

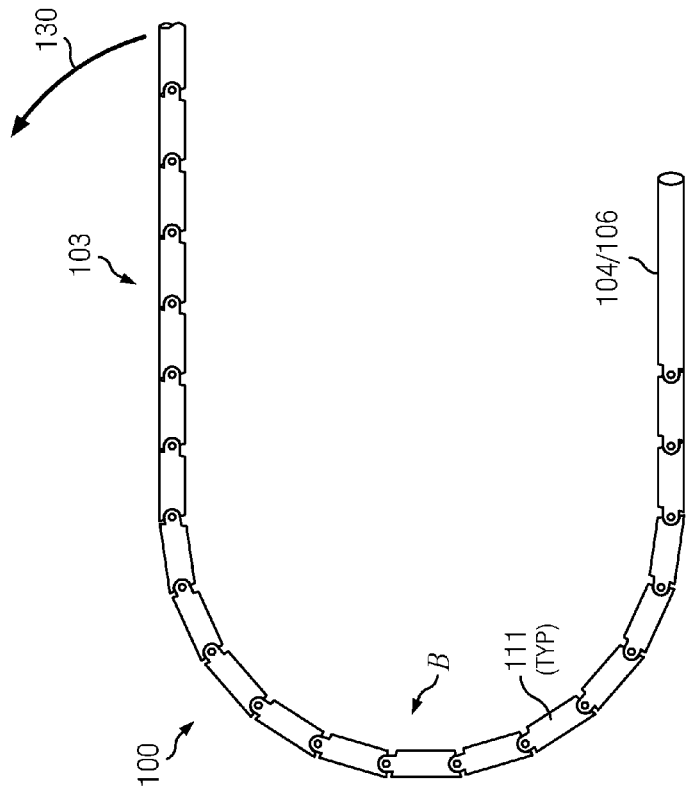
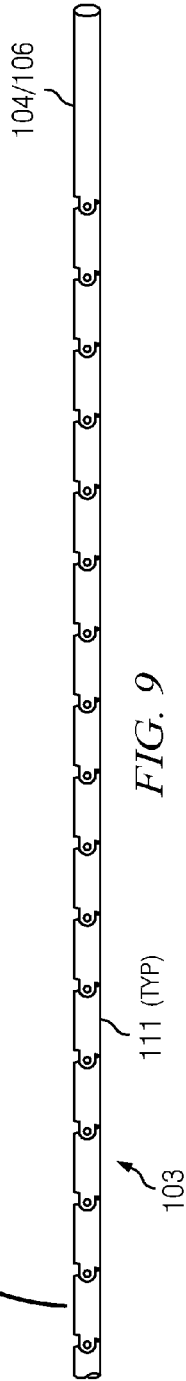
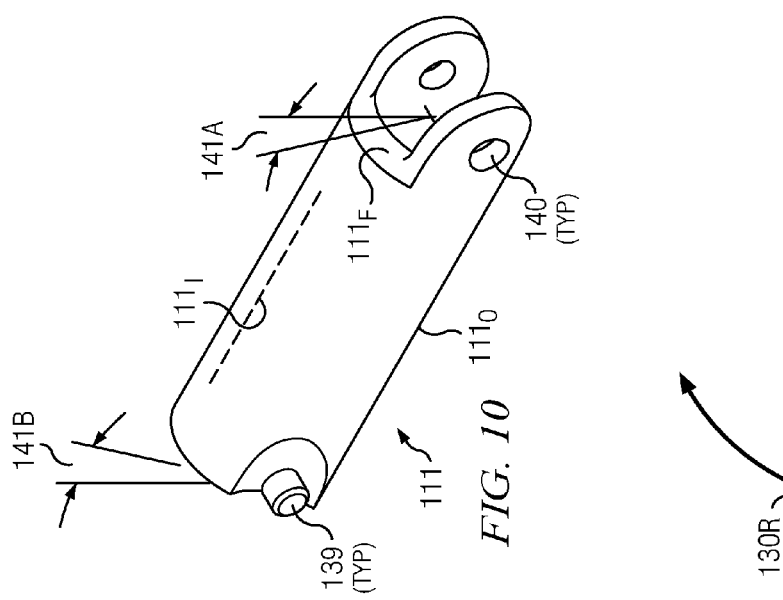

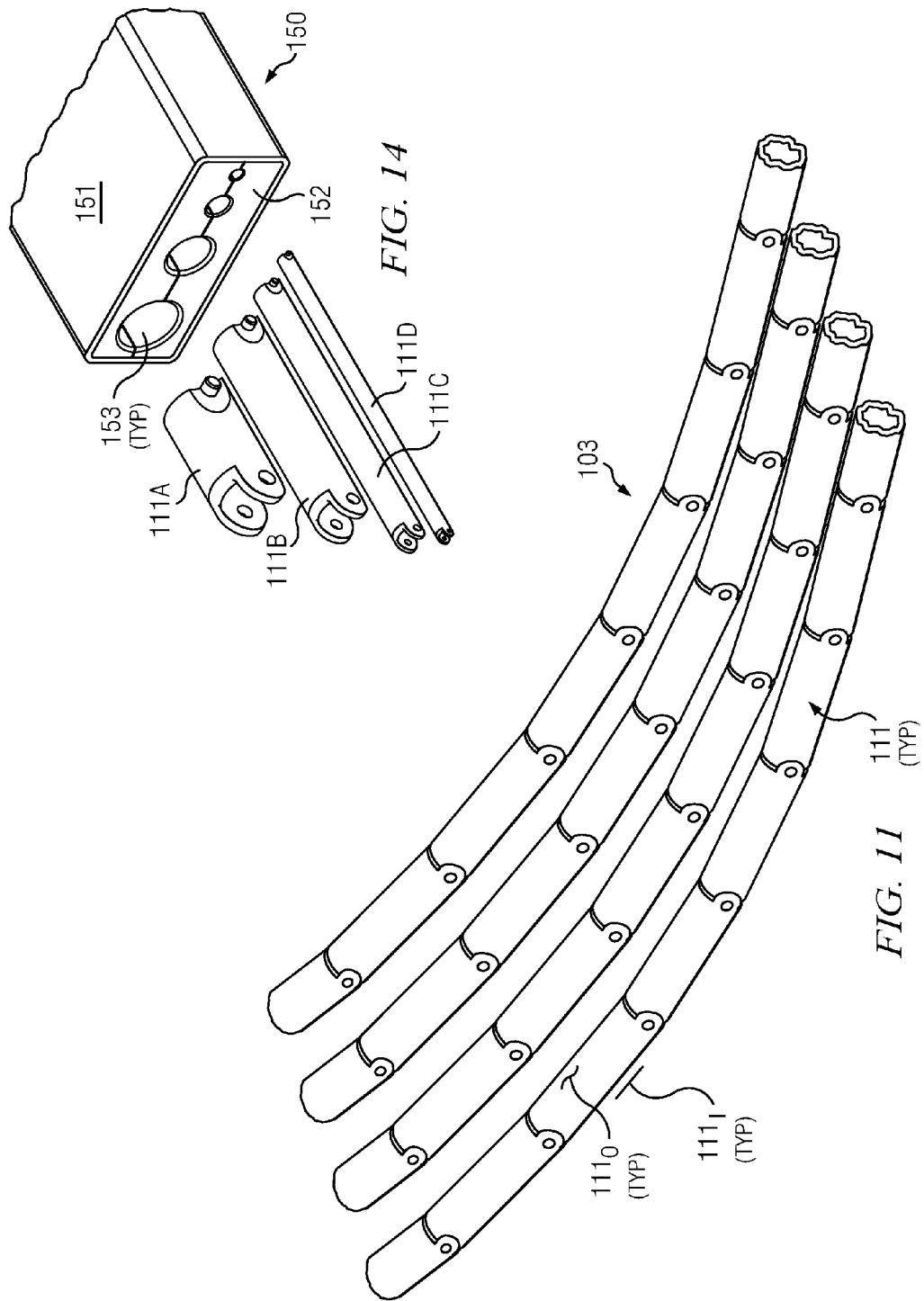

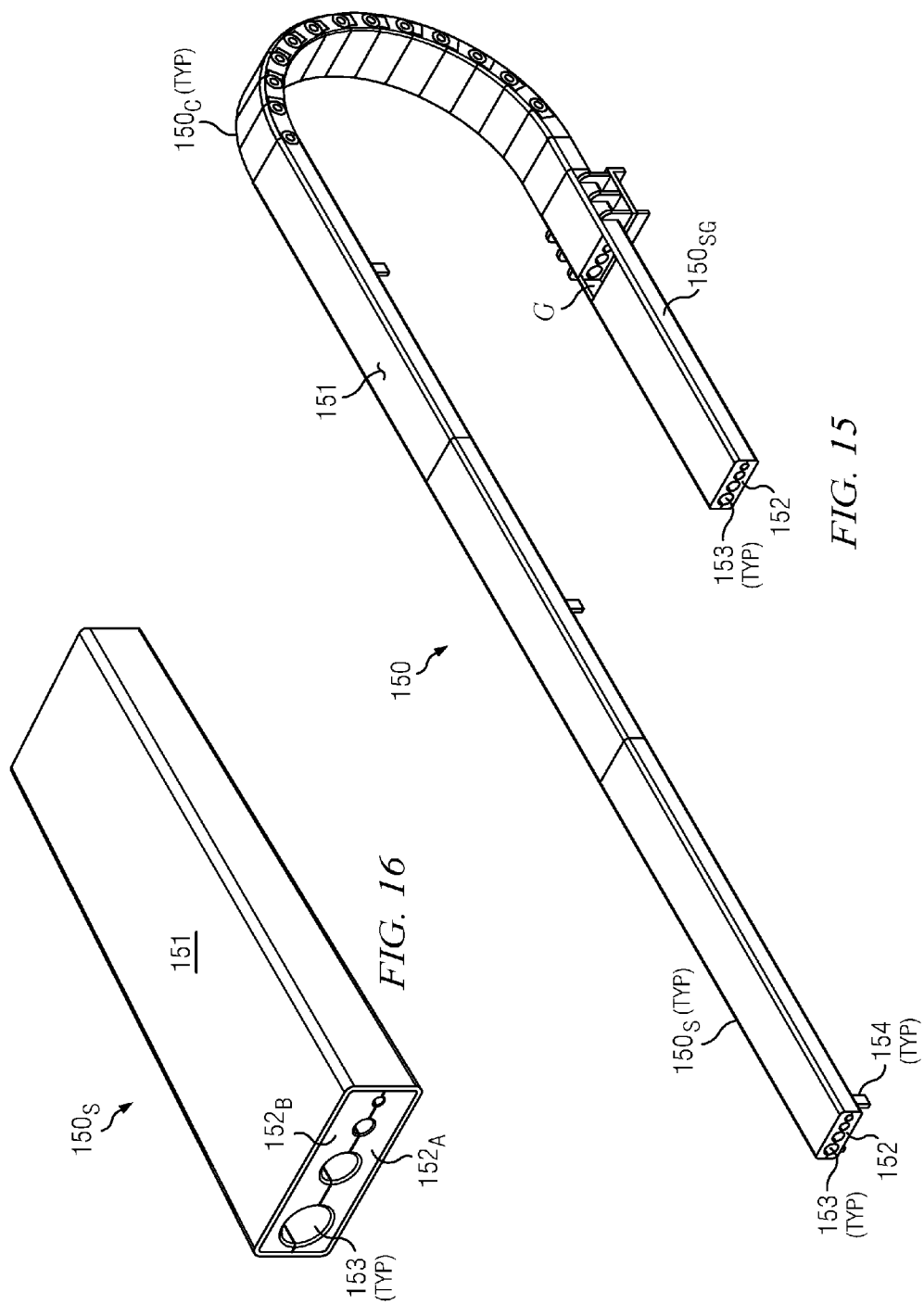

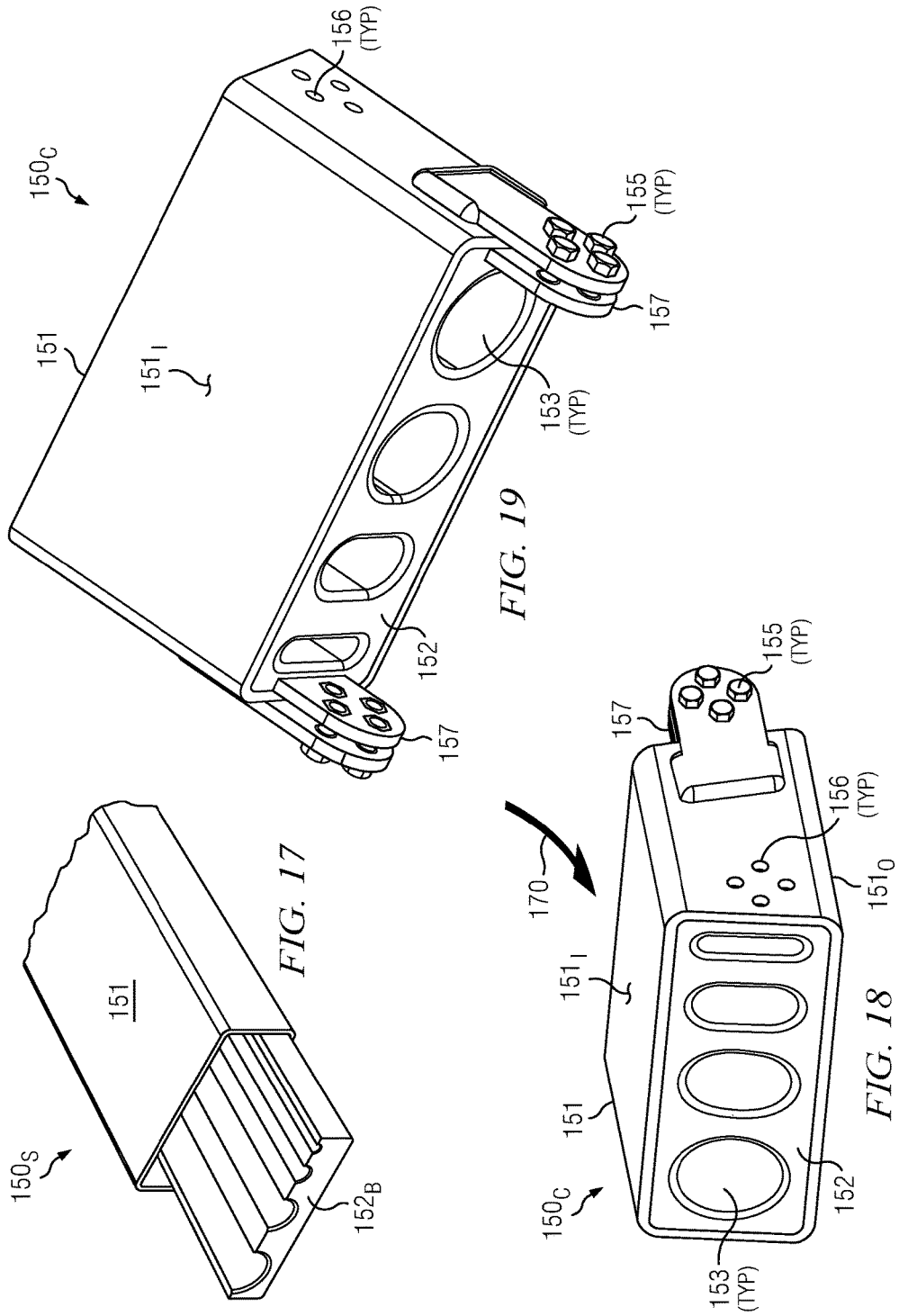

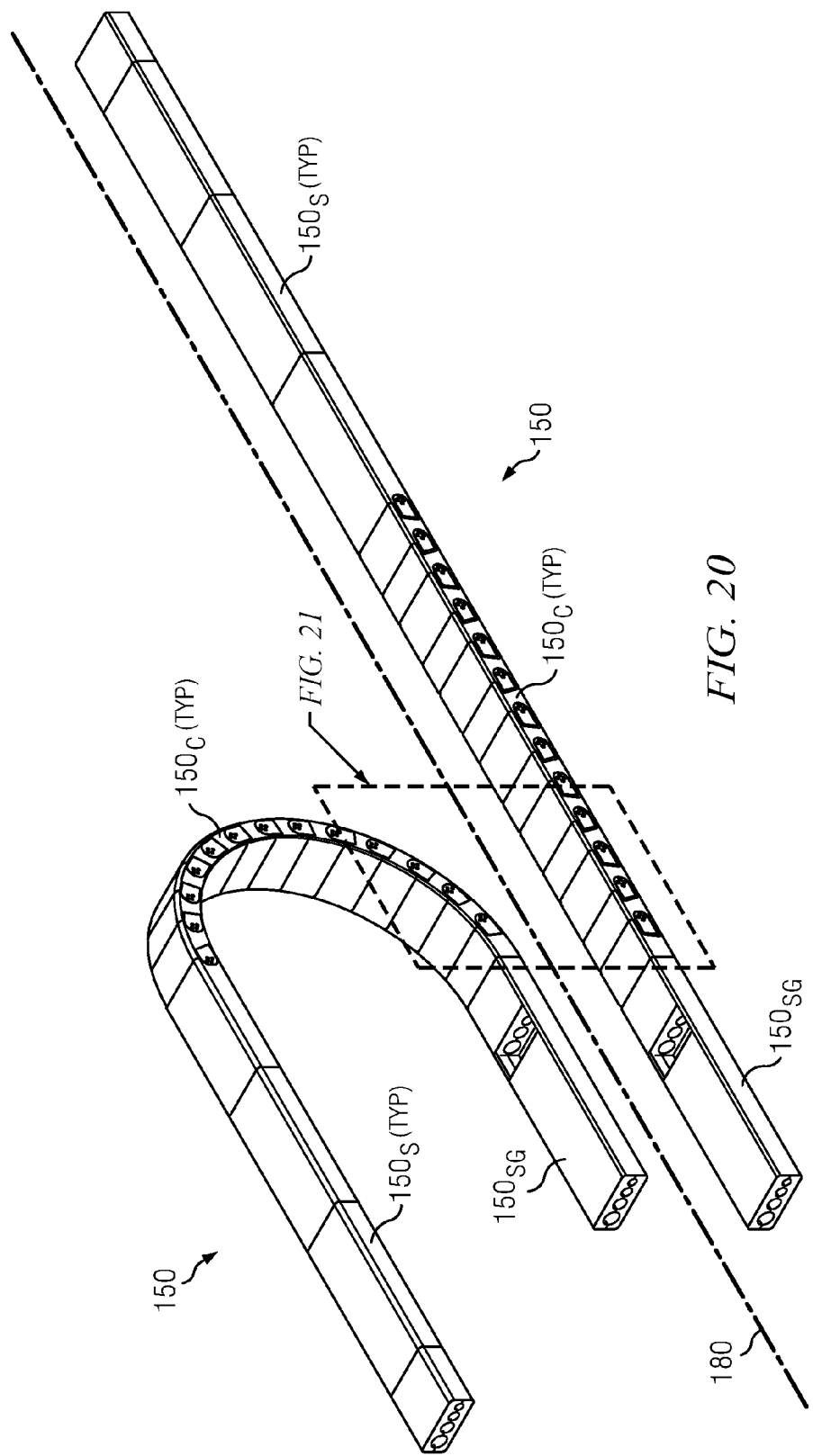

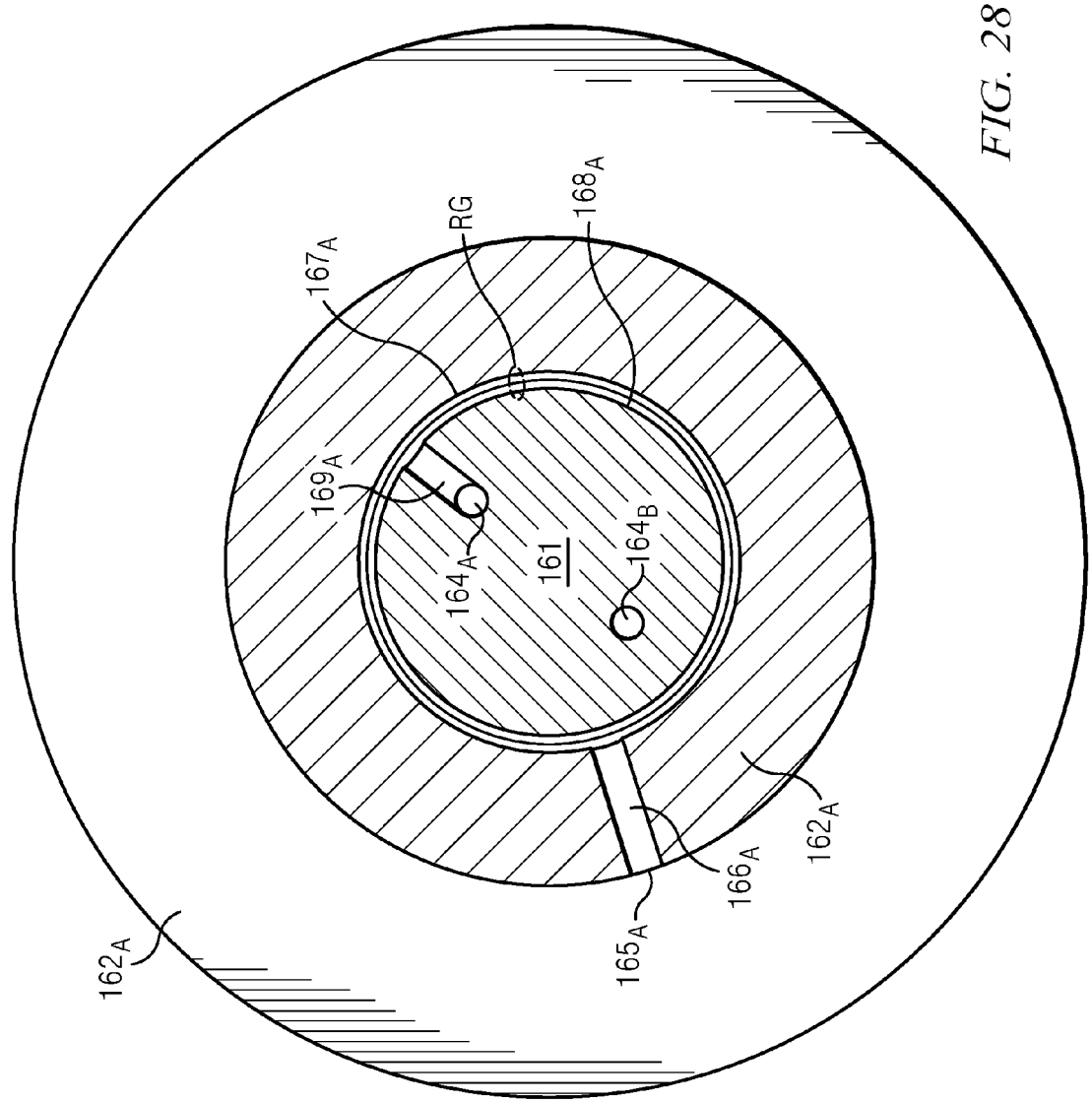

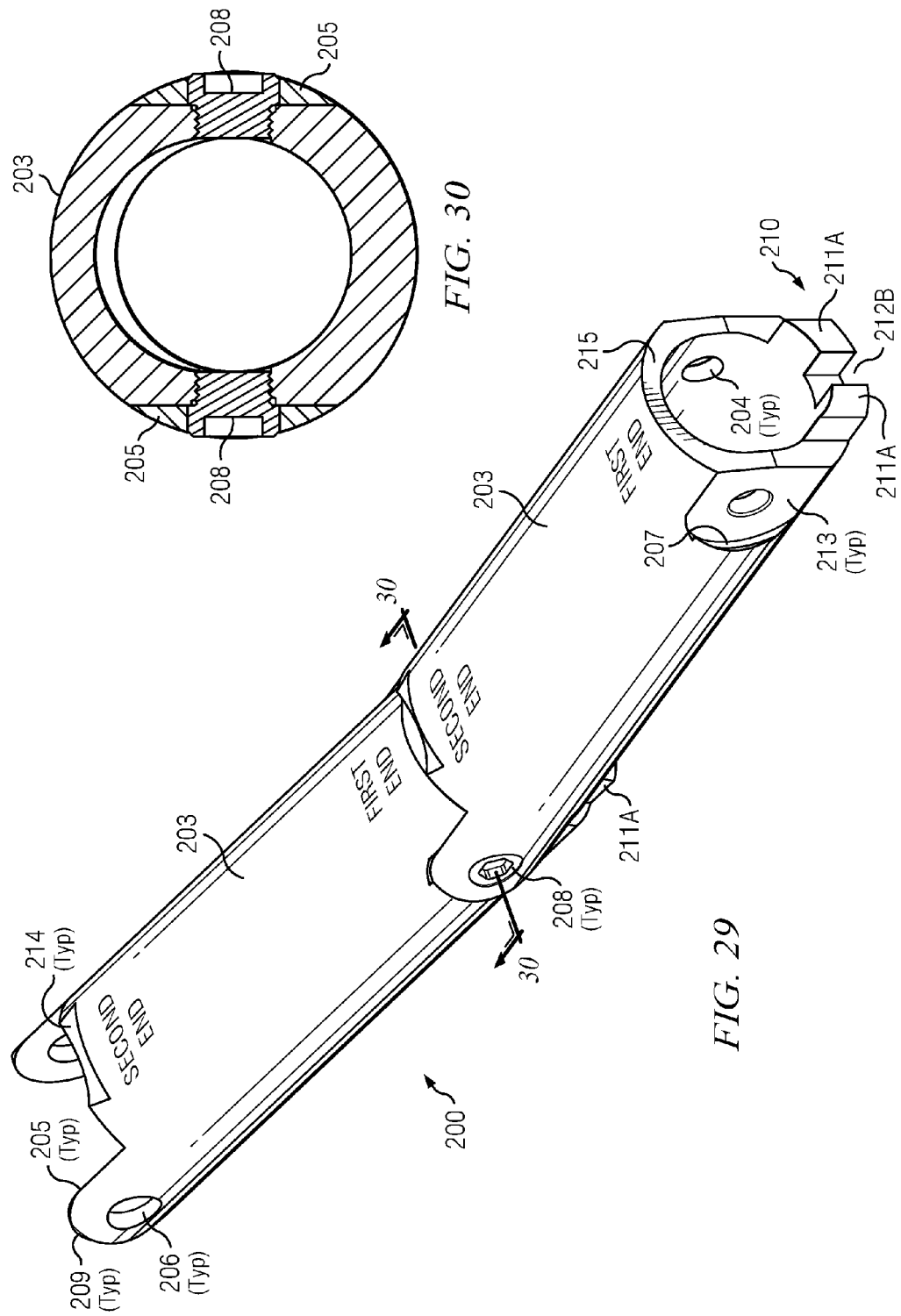

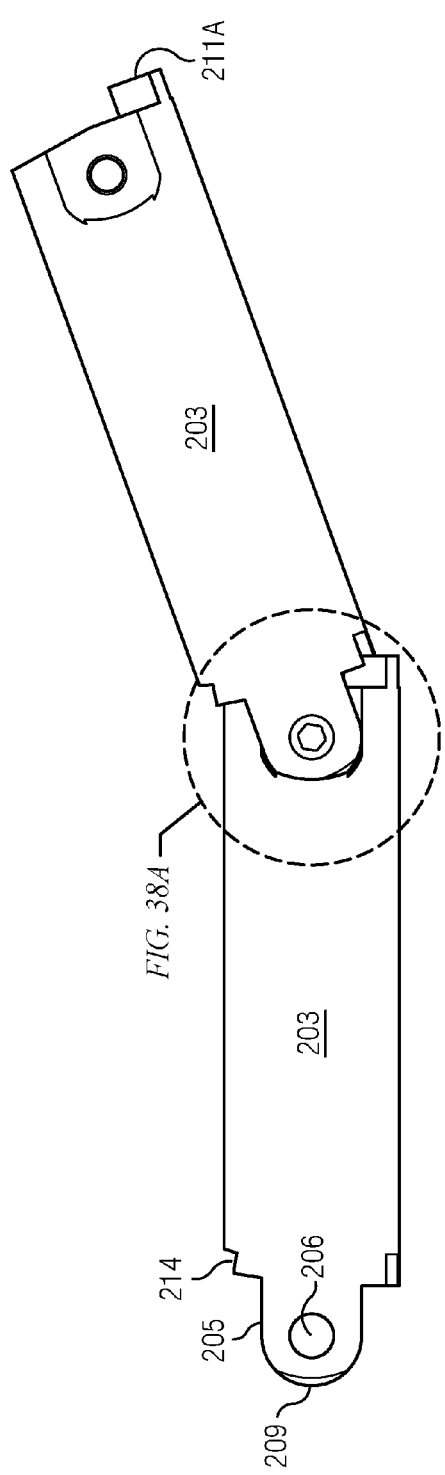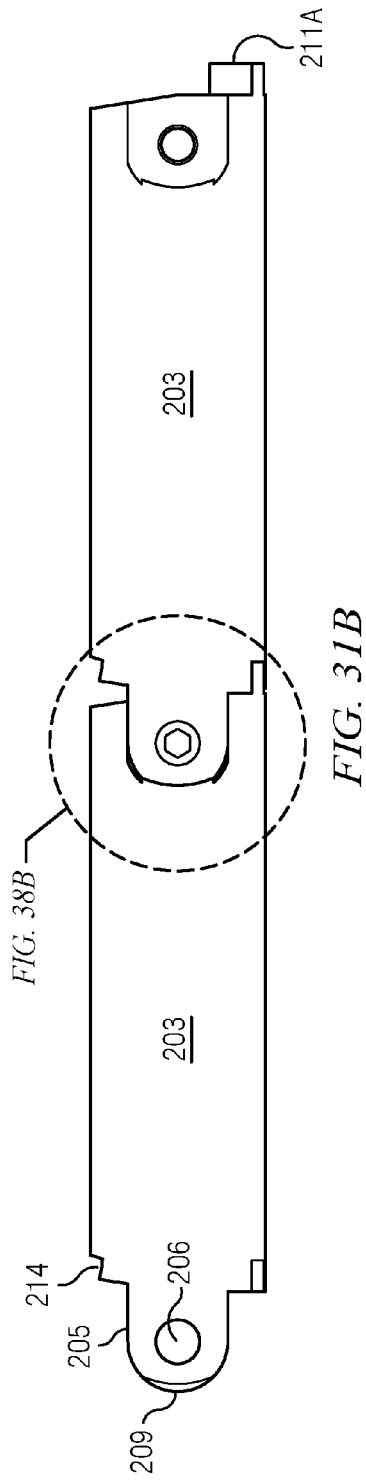

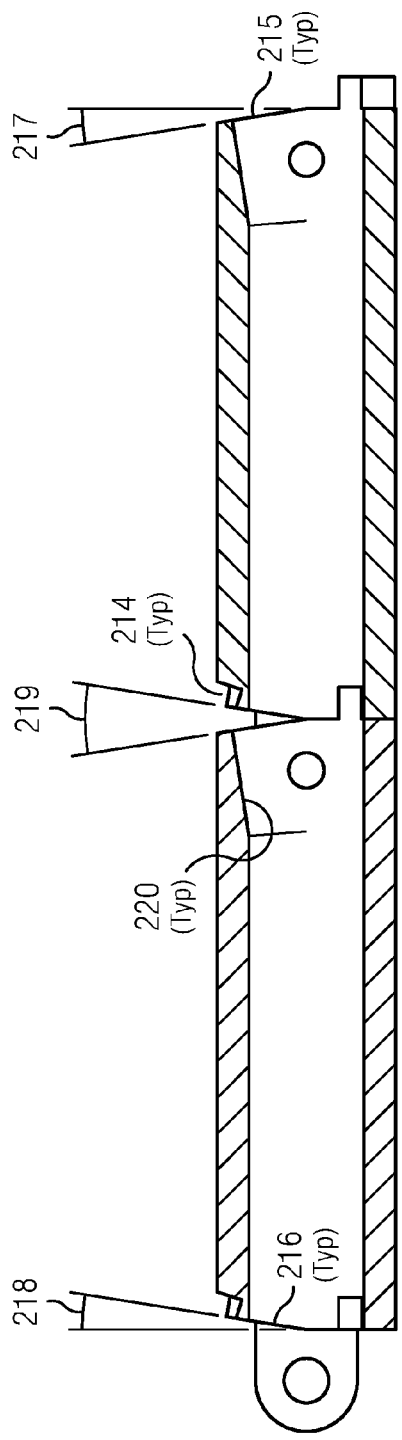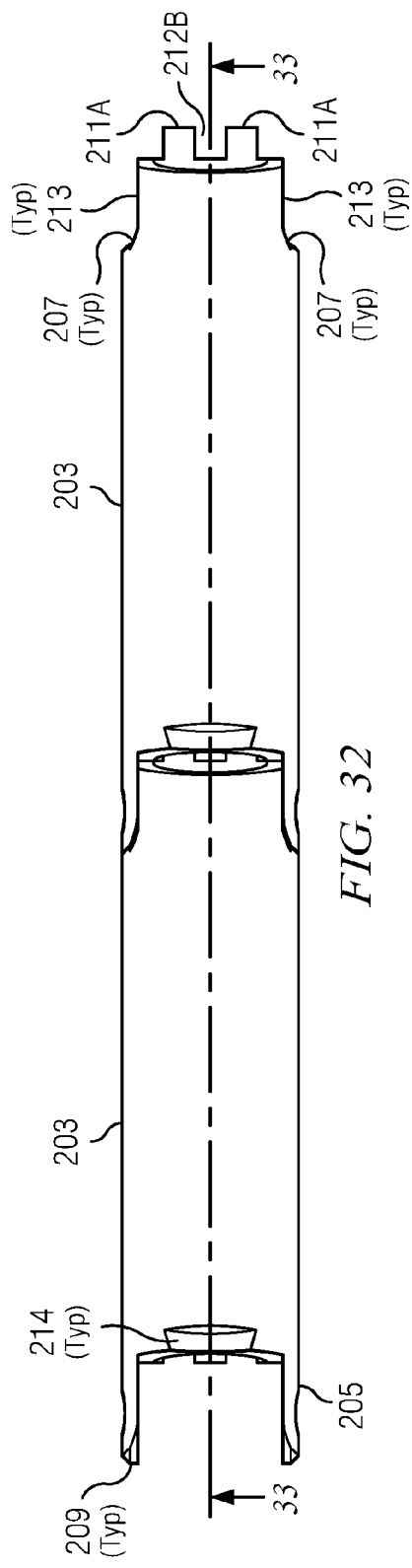

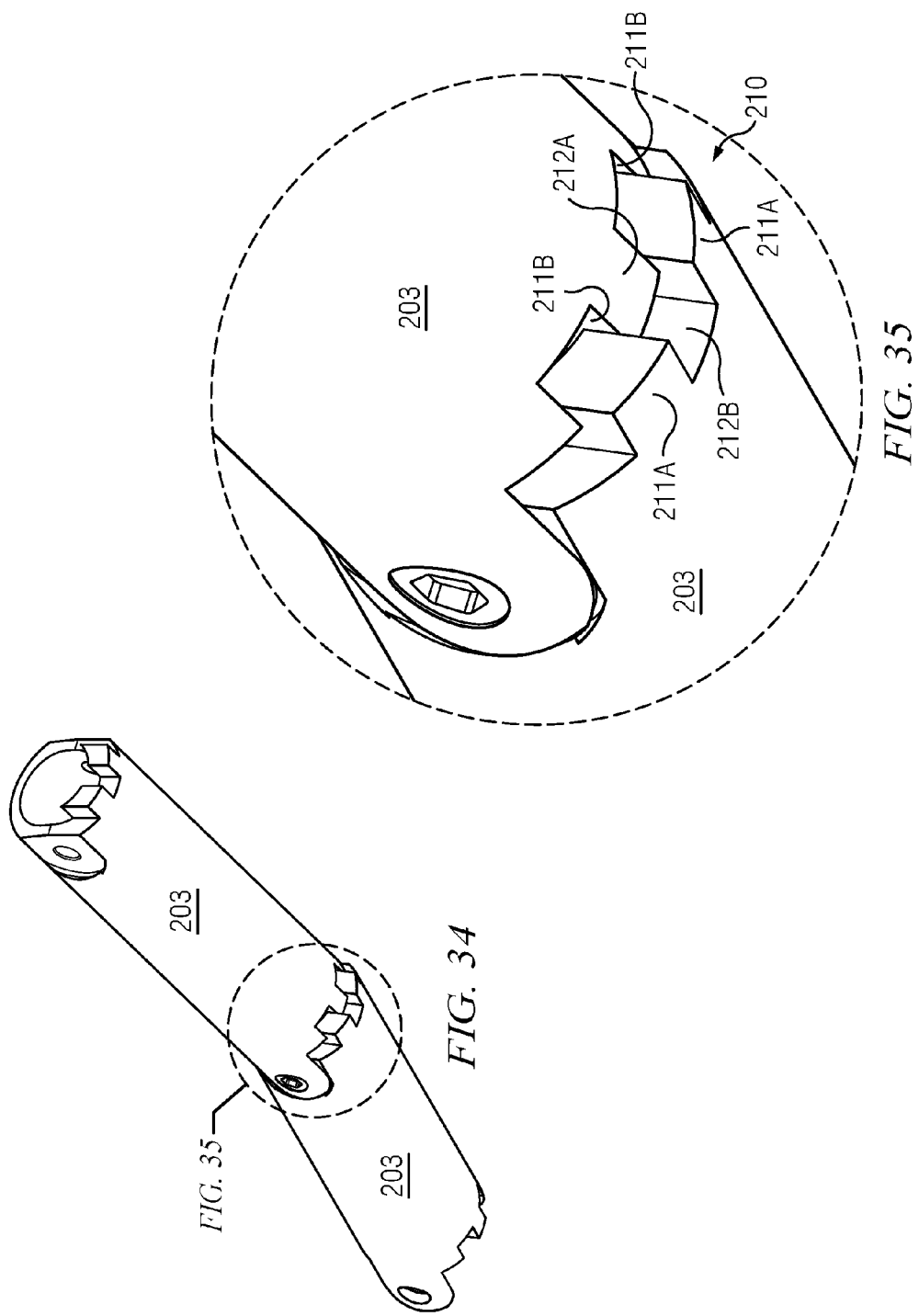

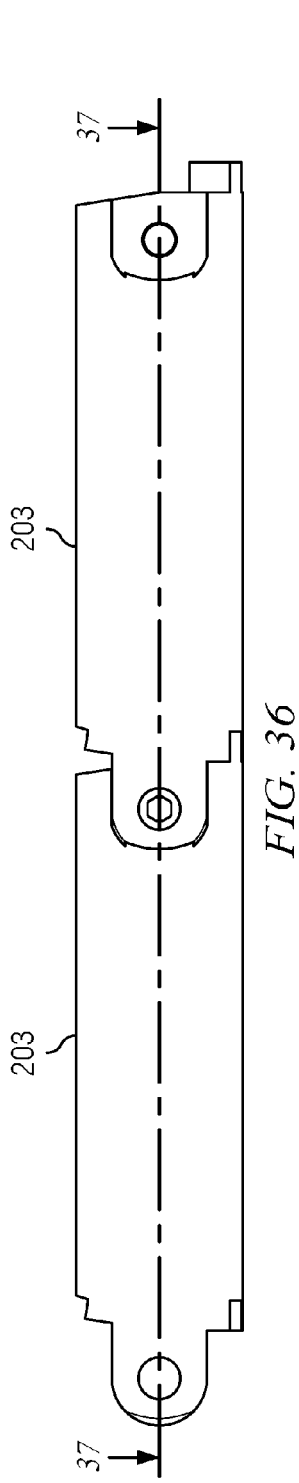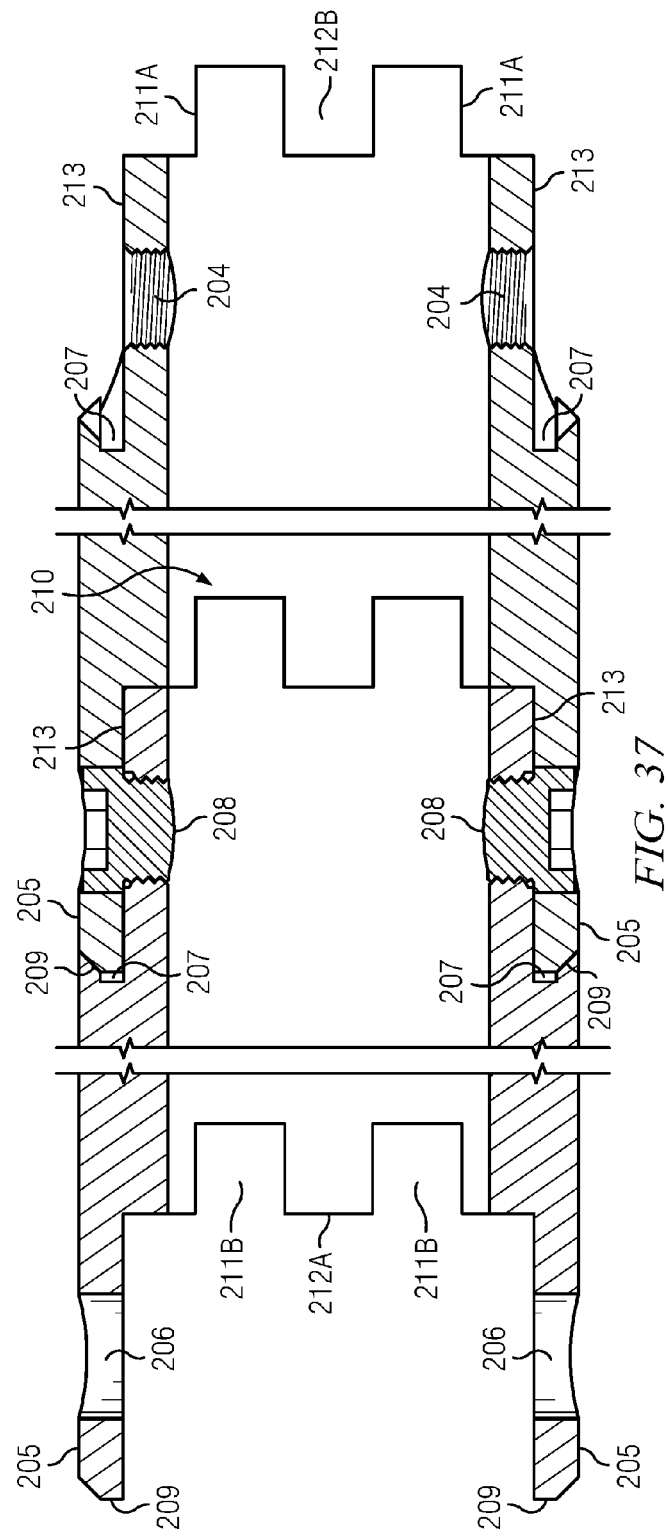
FIG. 36
FIG. 37

ENHANCED KNUCKLE-JOINTED LANCE USEFUL FOR INTERNAL CLEANING AND INSPECTION OF TUBULARS

RELATED APPLICATIONS

This application is a continuation-in-part of, and claims priority to, commonly-assigned U.S. patent application Ser. No. 13/833,108, filed Mar. 15, 2013 ("Parent Application"), which Parent Application in turn claims the benefit of, and priority to, commonly-assigned U.S. Provisional Application Serial No. 61/707,780, filed Sep. 28, 2012.

TECHNICAL FIELD

This disclosure is directed generally to technology useful, for example, in tubular cleaning and inspection operations in the oil and gas exploration field, and more specifically to an enhanced Knuckle Jointed Lance ("KJL"), in which the KJL is segmented in such a way to be spooled compactly onto and off a reel during extension and retraction thereof.

BACKGROUND

Throughout this disclosure, the term "Scorpion" or "Scorpion System" refers generally to the disclosed Thomas Services Scorpion brand proprietary tubular management system as a whole.

This Background section is directed to identifying technical problems in cleaning and inspecting, tubulars in the oil and gas exploration field, for which embodiments of the disclosed Knuckle-Jointed Lance ("KJL") are useful in addressing. However, it will be understood that deployments and applications for the disclosed KJL are not limited to cleaning and inspection of tubulars. This Background section (and the other disclosure herein) describes the KJL as used in cleaning and inspection of tubulars by way of an exemplary application only.

In conventional tubular cleaning operations, the cleaning apparatus is typically stationary, while the tubular is drawn longitudinally past the cleaning apparatus. The tubular is rotated at a relatively slow speed (in the range of 50 rpm, typically) while stationary, spring-loaded air motors drive spinning wire brushes and cutter heads on the inside diameter of the tubular as it is drawn past, via skewed drive rolls. These air brushes are colloquially called "cutters" although they perform abrasive cleaning operations on the internal surface of the tubular. Internal tubular cleaning operations typically also include hydroblasting in the prior art, although this is conventionally understood to be supplemental to the wire brush cleaning described above, rather than a primary cleaning process in and of itself. Typically this conventional hydroblasting is a low pressure water or steam pressure wash at pressures ranging from about 2,500 psi to 3,500 psi.

Good examples of conventional tubular cleaning apparatus are marketed by Knight Manufacturing, Inc. (formerly Hub City Iron Works, Inc.) of Lafayette, La. These products can be viewed on Knight's website.

One drawback of conventional tubular cleaning apparatus is that, with the cleaning apparatus stationary and the tubular drawn longitudinally across, the apparatus requires a large building. Range 3 drilling pipe is typically 40-47 feet long per joint, which means that in order to clean range 3 pipe, the building needs to be at least approximately 120 feet long.

In order to reduce footprint, the tubular may be held stationary and rotated, while cleaning and inspection tools (on the distal end of hoses, wires, etc.) may be inserted or "stabbed" into the interior of the stationary, rotating tubular. Advantageously the hoses, wires, etc. (including multiples thereof) may be inserted into the tubular inside a segmented lance. In addition to being a carrier of multiple hoses, wires, etc. a segmented lance may provide sufficient rigidity to deliver tools to a far end of a long rotating tubular in response to a "push force" inserting the lance at a near end. At the same time, a segmented lance may also provide flexure in at least one direction to enable the lance to be rolled up and unrolled onto and off a reel when extending and retracting the lance. Additionally, by absorbing such contact wear itself, a segmented lance protects the hoses, wires, etc. carried inside the lance from contact wear against the interior of the rotating tabular during operations.

U.S. Pat. No. 6,543,392 to Ashton et al. ("Ashton") discloses a segmented lance for cleaning and inspecting the interior of individual tubes in tube bundles in steam generators. One of the problems Ashton seeks to solve is to deliver remote cleaning tools and inspection devices initially through a horizontal portion of a steam generator tube, then round a 90-degree deviation in the tube, and then up a vertical portion of the tube. One embodiment disclosed in Ashton provides segmented lance for delivering remote tools and devices,. The segmented lance includes a hinged connection between lance segments, in which rotation about the hinges is limited to incremental deflection between neighboring segments. As a result, the lance retains rigidity in response to a "push force" while still having sufficient flexure (via cumulative relative rotation about consecutive pinned connections) to enable an eventual 90-degree turn.

FIG. 17 of Ashton discloses details of the hinged connection between neighboring lance segments. The Ashton segment design presents several drawbacks. FIG. 17 shows the hinge pins fixed rigidly on one end of the segment. Ashton provides no disclosure as to how the segments are assembled into a lance. FIG. 17 suggests that the ears on one end must be pried apart wide enough so that the ear holes may slide over the fixed pins. This is an inherently weak design, in which the ears must necessarily be made of weak, elastic material to slide over the pins. As a result, the overall segmented lance will also be weak and elastic. If the ears, are made of a harder material, such as metal, then prying them apart to slide over the pins will subject the ears to deformation, cracking or even failure. A much improved design would provide holes at each of the conjoined ends of neighboring segments, with a trunnion or other pin inserted through both sets of holes to faun a pinned connection. This design would permit assembly without stressing the ears, and would strengthen the hinged connection itself by putting the axis of rotation in a location surrounded by segment wall material.

A further weakness in the Ashton hinged connection design is that with the pin in its disclosed position on FIG. 17 near the very tip of a segment. the assembled lance allows sharp bends between neighboring segments. Hoses and cables to be carried inside the lance (see Ashton FIG. 18) may have minimum bend radius specifications for which sharp lance bends such as suggested on Ashton FIG. 17 might be non-compliant. An improved design would provide safeguards against sharp lance bends that might possibly damage internal hoses or cables.

The overall segmented lance disclosed by Ashton also presents several drawbacks. First, Ashton's segmented lance embodiment may not be properly designed to make a 90-degree turn as drawn up in Ashton. FIGS. 17 and 18 of Ashton illustrate lance segments that are permitted limited incremental relative rotation, whose cumulative relative rotation eventually allows a 90-degree turn. FIG. 21 of Ashton illustrates a drive mechanism for the segmented lance that causes the lance to make a sharp 90-degree turn that would be impossible in view of Ashton's FIGS. 17 and 18. Second, a segmented lance such as disclosed in Ashton is likely to encounter additional forces during operations. For example, a "push force" may cause the lance to twist as the lance moves along the tube. As a result, torsional forces will exert themselves on the hinged connections. In addition, inertia and friction forces, plus the dead weight of the lance, will all likely combine to exert compression forces on the hinged connections. In sum, the hinged connections are likely to come under considerable stresses during operations. The hinged connections are also the weakest points of the segmented lance. Ashton's pin enabling the hinged connection (as seen on Ashton's FIG. 17) is located at the very tip of each lance segment, and is thus particularly weak in its native state. Ashton further discloses no safeguards to mitigate against the additional forces and stressed likely to be encountered by Ashton's hinged connection during operations, as described above. It should be noted that failure of a hinged connection during operations as described by Ashton could be highly disadvantageous, potentially leaving, a portion of the lance stranded in a remote section of tube, and retrievable only with great difficulty.

Furthermore, Ashton makes no disclosure how the segmented lance is stored during extension and retraction of the lance during cleaning and inspection operations, much less during periods when not in use. Ashton further does not address measures that may be required to minimize and alleviate bending stresses exerted on hoses or wires carried inside the segmented lance when the lance turns through 90 degrees from horizontal to vertical, especially through the sharp 90-degree bend illustrated on Ashton's FIG. 21.

There is therefore a need in the art to improve the design (and ultimately, the performance) of segmented lances similar to those disclosed in Ashton. Ideally, such improved designs will strengthen the lance, particularly at the hinged or pinned connections, in order to make the lance less susceptible to failure during operations. Such improved designs will also address compact storage of the lance (advantageously on a reel), with the lance in an unstressed state during such storage, both during extension/retraction operations and during periods of non-use

SUMMARY AND TECHNICAL ADVANTAGES

Aspects of the Scorpion System disclosed and claimed in this disclosure address some of the above-described drawbacks of the prior art. In preferred embodiments, the Scorpion System rotates the tubular to be cleaned (hereafter, also called the "Work" in this disclosure) while keeping the Work stationary with respect to the cleaning apparatus. The Scorpion System then res the cleaning apparatus up and down the length of the Work while the Work rotates.

In currently preferred embodiments, the Work is typically rotated at speeds in a range of about 400-500 rpm, and potentially up to 1,750 rpm under certain criteria. By contrast, the Work may also be rotated as slowly as 0.01 rpm in such currently preferred embodiments, in order to facilitate high resolution local cleaning, inspection or data gathering/analysis. However, nothing in this disclosure should be interpreted to limit the Scorpion System to any particular rotational speed of the Work. Currently preferred embodiments of the Scorpion System further draw the cleaning apparatus up and down the length of the Work at speeds within a range of about 0.5 to 5.0 linear feet per second ("fps"), depending on the selected corresponding rotational speed for the Work. Again, nothing in this disclosure, should be interpreted to limit the Scorpion System to any particular speed at which the cleaning apparatus may move up or down the length of the Work.

The Scorpion System provides a multi-lance injector assembly (MLI) to clean the internal surface of the Work. The MLI provides a series, of extendable and retractable lances that move up and down the internal surface of the Work as it rotates. Each lance provides tool hardware to perform a desired lance function. Examples of lance functions may include, individually or in combinations thereof, and without limitation: hydroblasting, steam cleaning, washing and rinsing, high and low volume compressed air blowing, gas drying (such as nitrogen drying), rattling head cutters, abrasive cleaning, brushing. API drift checking, sensor or other data acquisition (including visual video inspection, thermal imaging, acoustic examination, magnetic resistivity examination and electromagnetic flux examination). Data acquisition may be in the form of static or streaming data acquisition. Lances may have amplifiers on board to boost sensed or generated signals, The MLI enables extension and retraction of individual lances, one at a time, in and out of the Work. The MLI further enables a user-selected sequence of internal surface cleaning and related operations by moving different lances, according to the sequence, into and out of position for extension and retraction in and out of the Work.

Currently preferred embodiments of the MLI provide one or more Knuckle-Jointed Lances ("KJLs") to deliver tool hardware back and forth along the interior of the Work as the Work rotates. In such embodiments, each KJL is a segmented lance with articulated joints (preferably, pinned connections) between neighboring segments. The segmented aspect of the KJL gives the lance sufficient rigidity to be able to be "pushed into" (i.e. extended into) and "pulled out of" (i.e. retracted from) the Work from outside one end of the Work as the Work rotates, in order to deliver tool hardware remotely to the entire interior, of the Work. At the same time, the segmented aspect of the KJL allows the lance to be rolled up onto a reel when not inside the Work. The partially-trapezoidal shape of the neighboring KJL segments enables limited incremental radial deflection at each pinned connection. This incremental radial deflection permitted at each pinned connection cumulatively allows the KJL, overall, to spool onto a reel (i.e., to "wrap" around the circular base drum or hub of a reel).

It will be understood that a reel is the currently preferred manner in which to store a KJL as described in this disclosure. Reel storage, and preferably, nested reel storage as described in this disclosure, enables compact and efficient storage of the KJL when not in use. Placement of a reel near the entrance to the interior or the Work allows the KJL to be extended into the Work by rolling the KJL off the reel. Conversely, the KJL may be retracted out of the work by rolling the KJL onto the reel. With particular reference to the nested reel storage described in this disclosure, such nested storage allows the KJL to be spooled onto and off the reel, and stored on the reel in a spooled state, with minimal stress to the KJL segments and their pinned connections.

"Nest", "nesting" or "nested", as used in this disclosure means that responsive to user assignment of a predetermined length to each KJL segment according to the KJL segment's corresponding pre-ordained position in the KJL, the KJL is disposed to spool onto a reel in nested fashion, such that for each spooling revolution made by the KJL onto the reel, (a)

KJL segments stack in circumferential registered layers around the reel and (b) pinned connections between KJL segments substantially coincide in radial vectors from a center of the reel. It will be appreciated that notwithstanding the limited radial deflection provided at each pinned connection between neighboring KJL segments, the KJL segments are nonetheless rigid straight lengths spooled onto a circular reel, and thus the KJL segments may experience bending and tensions stresses as they are spooled onto the reel. Nesting the KJL segments as they are spooled onto the reel, as described in this disclosure, minimizes those tension, bending and other stresses.

It will also be appreciated that although currently preferred embodiments of the KJL are described in this disclosure in association with a reel, the scope of this disclosure is not limited to such reel storage of KJLs. Moreover, the scope of the KJL described in this disclosure is not limited to the Scorpion System application of cleaning and inspecting tubulars. Embodiments of the KJL described in this disclosure have wide ranging industrial applications as discussed further below.

Returning now to discussion of the MLI more generally, tool hardware on any particular lance may provide for single or shared operations on the lance. For example, in some exemplary embodiments, data acquisition regarding the condition of the internal surface of the Work may be via sensors provided on tool hardware shared with cleaning operations. In other embodiments, the MLI may provide a lance dedicated to data acquisition.

Similarly, in some exemplary embodiments, API drift checking may be advantageously combined with other operations on a single lance. Running an API-standard drift on a lance in and out of the Work is useful not only to check for dimensional compliance of the Work with API standards, but also to locate and hold other operational tool hardware in a desired position relative to the Work as the lance extends and retracts. Especially on larger diameter Work, it may be advantageous (although not required within the scope of this disclosure) to attach a drift-like assembly to other lance tooling in order to accomplish several advantages. A drift or drift-like assembly: (1) protects more fragile internal parts of the lance and drift mechanisms; (2) minimizes friction, especially in view of the rotational speed of the Work; and (3) keeps the lance stabilized and positioned correctly inside the Work.

In a currently preferred embodiment, the MLI provides four (4) separate lances for internal surface cleaning and related operations. Nothing in this disclosure, however, should be interpreted to limit the MLI to any particular number of lances. In the currently preferred embodiment, the four lances are provided with tooling to accomplish the following exemplary operations:

Lance 1: High pressure water blast for concrete removal and general hydroblasting operations, or steam cleaning, especially on severely rusted or scaled interior surfaces of the Work.

Lance 2: Low pressure/high temperature wash, for general tubular cleaning operations, including salt wash and rust inhibitor coating.

Lance 3: Steel Wire Brushes and/or rattling/cutter head abrasive treatment.

Lance 4: Data probes, sensors, thermal imaging devices or specialized still/video camera probes.

Referring to Lance 3 in more detail, rotating steel wire brushes and/or steel rattling heads are provided for further internal surface cleaning after high pressure and/or low pressure washing phases. In another embodiment, data sensors may be deployed instead to share Lance 2 with the above described low pressure/hot wash function. In another alternative embodiment, high or low volume compressed air or nitrogen may be deployed to Lance 3 for drying and/or expelling debris. The compressed air may also supply pneumatic tools deployed on the lance.

Yet further alternative embodiments may deploy a variety of inspection hardware on various of the lances. For example, acoustic sensors may be deployed for sonic inspection. Magnetic resistivity sensors and magnetic flux sensors (such as a hall effect sensor) may be deployed for magnetic flux inspection. Amplifiers may be deployed to boost signals.

The range of inspection options envisioned in various embodiments of the MLI is varied. For example, visual inspection via video or still cameras may identify and analyze lodged objects in the wall of the Work in real time. Geometry and circularity of the Work may be measured and tagged in real time. Visual inspection video or still cameras may also be used to examine areas of interest on the internal wall of the Work more closely. Such areas of interest may be identified and tagged by visual examination, or by other examination (earlier or at the same time) by, for example, thermal imaging, acoustic analysis or magnetic flux/resistivity analysis. Such areas of interest may include loss in tubular wall thickness, or other conditions such as pitting, cracking, porosity and other tubular wall damage.

It will be further appreciated that inspection and examination data acquired during MLI operations may also be coordinated (either in real time or later) with other data acquired regarding the Work at any other time. In particular, without limitation, inspection and examination data may be, for example, (1) coordinated with earlier data regarding the Work to provide a history on the Work, or (2) coordinated in real time with comparable data obtained concurrently regarding the exterior surface of the Work to provide a yet more detailed and high resolution analysis of the state of the Work. The scope of this disclosure is not limited in this regard.

Again, nothing in this disclosure should be interpreted to limit the MLI lances to be assigned any specific tooling to perform any specific operations. Any lance may perform any operation(s) per user selection, and may deploy any tooling suitable to perform such user-selected operation(s).

In currently preferred embodiments of the Scorpion System, the lances provided by the MLI are not self-propelling up and down within the interior of the Work. The lances are moved up and down the interior of the Work as further described in this disclosure. However, nothing in this disclosure should be interpreted to limit the lances to a non-self-propelling embodiment. Other embodiments within the scope of this disclosure may have full or partial lance propulsion functionality, including propulsion apparatus that gains fraction on. the interior surface of the Work.

Focusing again now on currently preferred embodiments of the MLI in which one or more Knuckle-Jointed Lances ("KJLs") are deployed, each KJL is preferably configured to enable nested storage on a reel as described generally above in this Summary section. Each KJL further preferably provides features to strengthen the KJL overall, and particularly at the pinned connections between KJL segments, in order to make the KJL less susceptible to failure during operations (including operations inside the Work, or during spooling/unspooling into or out of the Work, or during reel storage while not in use).

Nested Reel Storage: Spooling Profile Feature (Including Transitional Feature)

As described in this disclosure, currently preferred embodiments of the KJL include a concatenated string of rigid tube KJL segments wherein neighboring segments have a pivoting connection. The pivoting connection is preferably a pinned connection enabled via a pair of trunnions rotatably connecting trunnion holes on a first end of a KJL segment with ear holes in ears on the second end of a neighboring KJL segment. The partially-trapezoidal shape of the neighboring KJL segments enables limited incremental radial deflection at each pinned connection. This incremental radial deflection, permitted at each pinned connection cumulatively allows the KJL overall, to spool onto a reel.

As noted above in this disclosure, preferred embodiments of the KJL described in this disclosure are configured to spool around a base drum (or hub) of a reel in nested fashion. Successive KJL "layers" stack in register onto the reel as the KJL spools multiple times around the reel. Properly nested, the pinned connections in successive layers of KJL segments on the reel trace generally radial vectors pointing away from the center of the reel. To enable such nesting, the lengths of individual KJL segments are we-ordained according each KJL segment's position in the KJL relative to other KJL segments. The lengths of KJL segments that stack further out on the reel are longer than the lengths of corresponding KJL segments that stack further in. Transitional KJL segments are also placed in pre-ordained positions in the KJL. The transitional KJL segments have transitional lengths that enable one stacked layer to transition smoothly onto the next, thus allowing compact nesting of multiple stacked layers.

As a result, the sequence of conjoined KJL segments in the KJL, each with its pre-ordained length according to its position on the KJL, is according to a predetermined stacking profile that defines the way in which the KJL will stack up on the reel. Stacking profiles are individually derived and calculated with reference to multiple parameters, according user specification. The parameters contributing to a user-selected stacking profile include, but are not limited to (1) the diameter of the base drum or hub of the reel, (2) the lengths and diameters of KJL segments, (3) the maximum incremental radial deflection permitted at each pinned connection between KJL segments, (4) the number of stacked layers desired, and (5) the linear length of KJL desired.

Referring now to the transitional KJL segments in the stacking, profile, preferably 3 of the 4 quadrants/portions of the reel's base drum are symmetrical arcs and the 4th quadrant is a transitional quadrant. In currently preferred embodiments, two transitional KJL segments in each spooled layer enable the KJL to stack up in compact nested layers. One transitional KJL segment is vertically extended to meet the, increased spooled radius of the next outer stacked layer of KJL segments. The second transitional KJL segment is horizontally extended to meet the increased spooled circumference of the next outer stacked KJL layer. These two transitional KJL segments allow multiple nested stacking of KJL layers on the reel where the radial deflection of neighboring KJL segments as spooled on the reel is within the limited incremental radial deflection permitted by each pinned connection between KJL segments. As a result, other than the transitional KJL segments, all other KJL segments on each layer may have the same lengths (simplifying manufacturing and assembly).

As noted above, a primary advantage of nesting KJL segments onto a reel according to a KJL spooling profile is the reduction in overall footprint of the KJL assembly, either in operational use or in storage. Another advantage is to minimize stresses on the KJL as spooled onto the reel, in contrast to stresses that might be encountered if the KJL was spooled onto a reel in un-nested fashion. Nesting avoids bending or tension stresses on individual KJL segments that might be associated with un-nested stacking.

Interlocking Torque Teeth Feature

As noted above, currently preferred embodiments of the KJL include a pinned connection between neighboring KJL segments, enabled via a pair of trunnions rotatably connecting trunnion holes on a first end of a KJL segment with ear holes in ears on the second end of a neighboring KJL segment. Currently preferred embodiments of the pinned connection also include interlocking torque teeth between the first end of one KJL neighboring segment and the second end of the other KJL segment. Enmeshment of two sets of teeth, one set on the first end of a one neighboring KJL segment and a second set on the second end of the other KJL segment, forms an interlocking toothed connection. Preferably the teeth are square or rectangular in shape, although the scope of this disclosure is not limited in this regard. The interlocking toothed connection is configured such that it is fully engaged (i.e. the teeth are in substantially full interlocking enmeshment) when the neighboring KJL segments are in straight line alignment about the pinned connection. Further, in preferred embodiments, the teeth within the interlocking toothed connection are long enough to remain partially engaged (i.e. partially interlocked) when the KJL segments are in full angular displacement about the pinned connection.

It will be appreciated that in many applications of the KJL portions of the KJL will configured to be straight, such that neighboring KJL segments will be in straight line alignment about their pinned connections ("straight line mode"). In such applications, other portions of the KJL will be configured to curved (such as when deployed on a reel), such that neighboring KJL segments will be in angular displacement about the pinned connection ("curved mode"). Focusing on the KJL portions in straight line mode, neighboring KJL segments are preferably shaped such that portions of the segments abut one another when in straight line mode (with interlocking toothed connection also fully engaged). When compression is applied to the KJL in straight line mode (such as when extending the KJL while spooling off a reel), the abutting portions of neighboring KJL segments and the interlocking teeth combine to create contact surfaces that add lateral and torsional stability in the presence of the compressive load, thereby increasing the axial compressive load capacity of the overall KJL. In addition, the interlocking toothed connection enhances the elasticity, rigidity and straightness of the KJL.

The interlocking toothed connection is advantageous in many applications for the disclosed KJL. However, the interlocking toothed connection is especially beneficial in exemplary applications described in this disclosure, in which the KJL is extended into a rotating tubular. The interlocking toothed connection helps restrain the torsional twisting load exerted on the KJL by the rotating tubular when the KJL contacts the interior surface of the rotating tubular. The interlocking aspect of the connection further helps to transfer torque throughout the KJL, thus distributing torsional stresses among many KJL segment connections and thereby significantly increasing the KJL's overall torque load capacity. The interlocking toothed connection further mitigates torsional twisting loads from damaging, bending or even shearing off pinned connections between neighboring KJL segments. The useful service life of a KJL is therefore enhanced and extended.

Mitigation of torsional loads by the interlocking toothed connections, as described above, is not limited to portions of the KJL in straight line mode. As noted above, the teeth within the interlocking toothed are preferably long enough to remain partially engaged when the KJL segments are in curved mode (such as when spooled onto a reel). Torsional loads may be encountered by the KJL when being spooled onto or off a reel, or otherwise displaced into curved mode. Again, the interlocking toothed connections mitigate against torsional and compressive stresses encountered by the KJL in curved mode.

Spooling Notch Feature (Helping KJL Segments to Stack on a Reel)

Preferred embodiments of the KJL provide a spooling notch feature to ensure compact KJL nesting onto a reel (refer spooling profile feature above) when the interlocking torque teeth feature is also provided (refer immediately above). As described with reference to the interlocking torque teeth feature above, the teeth within the interlocking toothed connection are long enough to remain partially engaged when the KJL segments are curved mode. However, the teeth either side of the interlocking toothed connection will be angularly displaced in such partial engagement in curved mode. Teeth will thus protrude out and potentially limit compact nesting of stacked layers of KJL segments when spooled onto a reel in such curved mode.

The spooling notch feature comprises a portion of material cut out and removed from the exterior wall of KJL segments. The notch is preferably located at the ears/ear holes end of each KJL segment (referred to as the "second end" of each KJL segment by convention throughout this disclosure). In embodiments where successive layers of KJL segments are spooled onto a reel, the spooling, notch location in KJL segments in one layer coincides with the location of protruding teeth from the interlocking tooth feature on KJL segments on the next innermost layer.

A primary advantage of the spooling notch feature is to facilitate the most compact spooled KJL assembly possible. Further, the spooling notch feature facilitates provision of the interlocking torque teeth feature on the KJL which adds its own advantages as described immediately above.

Ear Ledge Feature (Slip-Critical Failure Mitigation Feature)

As noted above, currently preferred embodiments of the KJL include a pinned connection between neighboring KJL segments, enabled via a pair of trunnions rotatably connecting trunnion holes on a first end of a KJL segment with ear holes in ears on the second end of a neighboring KJL segment. The second end of one KJL segment provides two opposing ears, one on each side, each of which is received over a corresponding ear cutout on the first end of the neighboring KJL segment. One trunnion hole is provided in each ear cutout, over which an ear hole is positioned when the one of the ears is received over the ear cutout. On each side, a trunnion passes through the ear hole and threadably engages the trunnion hole, thus providing the pinned connection.

Each ear provides an ear ledge on its end, and each ear ledge is configured to be slidably retained within a corresponding ear ledge recess provided in the ear cutout when the pinned connection is fully assembled. Each ear ledge recess is configured and shaped to slidably receive a corresponding ear ledge when the trunnions are received through the ear holes and fixed into the trunnion holes. The ear ledges and ear ledge recesses cooperate to restrain displacement of the ears with respect to the ear cutouts except for relative rotation between the ears and the ear cutouts about the pinned connection. The ear ledge feature is preferably an angular chamfer or bevel along the outer edge of approximately one half of the end tip of the ear. The ear ledge recess is shaped to receive the ear ledge feature, and to constantly retain the ear ledge within the ear ledge recess notwithstanding any permitted rotation of the KJL segments about the pinned connection. While a slidable retention, the depth of the ear ledge recess is selected such that the ear ledge preferably does not make contact with the deepest portions of ear ledge recess during rotation of the pinned connection, or even when the pinned connection is placed under expected operational compression loads.

A primary technical advantage provided by the ear ledge feature is that it adds strength, stability, consistency, and longevity to the useful life of the KJL. In particular, as noted, the ear ledge recesses prevent the tips of the KJL ears (i.e. the ear ledges) from contacting the bottom of the ear ledge recess. This prevents axial compressive forces from stressing the tips of the KJL ears when the KJL is being driven axially forward (e.g. extended into the Work). This in turn mitigates cyclic fatigue on the KJL ears and the pinned connection due to repetitive compressive forces.

Moreover, in embodiments in which the ear ledge includes an angular chamfer or bevel, the chamfer directs contacting forces inward. The overall axial strength and stability of the KJL is enhanced and increased significantly by mitigating against "slip critical" failure at lower-than-expected axial tensile and compressive loads. Examples of the types of slip critical failures the ear ledge feature as described will mitigate include: (1) slip critical failure as ears spread apart beyond the limits of the heads of the trunnions; (2) slip, critical failure of ears spreading apart and bending outward to the point of ears breaking off at the connection points to the KJL segment; and/or (3) slip critical failure of the trunnion pried and pulled out of the trunnion holes (stripping the threaded connections between trunnions and trunnion holes).

Hose Bend Radius Wall Taper Feature

It will be appreciated from discussion further on in this disclosure that a primary purpose of the KJL in the exemplary tubular cleaning/inspection embodiments described herein is to carry hoses and/or cables to inside the KJL to a supply a tools or instruments at a distal end of the KJL. It will be further appreciated that in such exemplary embodiments, it is highly advantageous to protect the integrity of these supply hoses and cables from incidental damage caused by the interior of the KJL. In particular, the supply hoses and cables should preferably be protected from sharp bends in the interior of the KJL at the pinned connections between KJL segments when the KJL is in curved mode. Such sharp bends may transfer into the hoses and cables and cause bending damage. Further, sharp edges on the interior of the KJL may cause cuts or gouges on the hoses or cables.

Preferred KJL embodiments provide an interior wall thickness taper at the KJL segment end generally leading the KJL as the KJL is extended from a reel, for example, into a tubular (such leading end referred by convention in this disclosure as the "first end"). For further reference, the wall thickness taper is preferably provided at the KJL segment end on which ear cutouts and trunnion holes are provided. The wall thickness taper is provided on a portion or the KJL segment interior wall opposing the interlocking toothed connection, such that when the KJL is in curved mode, the taper smooths out the pathway of the interior wall as the wall transitions from the first (leading) end of one KJL segment in a neighboring pair into the second (trailing) end of the other. As a result, sharp bends and edges inside the KJL interior are minimized. Further, the hoses and cables inside the KJL can bend more smoothly around portions of the KJL in curved mode, preferably staying within their individual safe minimum bend radius.

As just noted, a primary advantage of the hose bend wall taper feature is that it allows internal hose(s) and cable(s) provided inside the KJL to stay within their minimum inside bend radius specifications when the KJL is in curved mode. Referring specifically to exemplary applications of the KJL in tubular cleaning/inspection, all hoses used in API and other applications are required to stay within the specified safe operating parameters (including bend radius) for safety reasons. The hose bend wall taper feature thus maintains hose safety. Further, the hose bend wall taper reason maintains the hoses in a relatively unstressed state even when the KJL is in curved mode. Hose fatigue is therefore reduced, which increases the longevity of the hose and reduces the chance of expensive and potentially highly unsafe hose failure during cleaning or inspection operations.

Threaded Trunnion Connection (At Pinned Connection Between KJL Segments)

As described above, preferred embodiments of the pinned connection between two neighboring KJL segments provide a rotatable trunnion connection on either side. The trunnion preferably passes through the ear holes on the second end of one KJL segment and is retained by a threaded connection into the trunnion holes in the ear cutouts on the first end of the other KJL segment. Preferred trunnion embodiments provide a conventional hex recess for tightening (or removal) with an Allen wrench. The hex recess is provided in an outer dome whose diameter fits into the ear holes. The dome's curvature is preferably selected to approximate the curvature of the surrounding ears, and to minimize protrusion of the dome beyond the curvature of the surrounding ears. Contact surfaces between the trunnion dome and the ear holes are smooth, with an operational fit that promotes free rotation of the primed connection while at the same time minimizing friction and "slop". The threaded shank portion preferably is of a length such that the trunnion's threaded connection to the trunnion holes becomes tight before the trunnion protrudes through the inside wall of the KJL segment.

A primary advantage of the threaded trunnion connection is that its dome head shape preferably does not stand proud of the KJL segments when the trunnion is installed, or create a sharp edge. This in turn promotes smooth anti-snagging, low friction sliding by the KJL through tubulars during extension or retraction of the KJL, especially inside tubulars that may be rotating or stationary. The threaded trunnion connection design gives versatility in applications of KJL use beyond the exemplary tubular cleaning/inspection application described in this disclosure. The design is a safe, robust, and reliable connection. It is also a simple design such that the KJL requires no other parts beyond KJL segments and trunnions.

Focusing now on the disclosed Scorpion System as a whole, multiple high-level technical advantages are provided. For example:

Versatility. The Scorpion System as disclosed herein is described with respect to preferred embodiments thereof. However, it will be appreciated that such preferred embodiments are exemplary only, and many of the features, aspects and capabilities of the Scorpion System are customizable to user requirements. As a result the Scorpion System is operable on many diameters of tubular in numerous alternative configurations. Some embodiments may be deployed onto a U.S. Department of Transport standard semi-trailer for mobile service.

Substantially lower footprint of cleaning apparatus. As noted above, conventionally, the cleaning of range 3 drill pipe requires a building at Least 120 feet long. Certain configurations of the Scorpion System can, for example, clean range 3 pipe in a building of about half that length. Similar footprint savings are available for rig site deployments. As also noted above, a mobile embodiment of the Scorpion System is designed within U.S. Department of Transportation regulations to be mounted on an 18-wheel tractor-trailer unit, and be transported on public roads in everyday fashion, without requirements for any special permits.

Dramatically increased production rate in cleaning. An operational goal of the Scorpion System is to substantially reduce conventional cleaning time. Further, the integrated yet independently-controllable design of each phase of cleaning operations allows a very small operator staff (one person, if need be) to clean numerous tubulars consecutively in one session, with no other operator involvement needed unless parameters such as tubular size or cleaning requirements change. It will be further understood that in order to optimize productivity, consistency, safety and quality throughout all tubular operations, the systems enabling each phase or aspect of such operations are designed to run independently, and each in independently-selectable modes of automatic, semi-automatic or manual operation. When operator intervention is required, all adjustments to change, for example, modes of operation or tubular size being cleaned, such adjustments are advantageously enabled by hydraulically-powered actuators controlled by system software.

Improved quality of clean. It is anticipated that the Scorpion System will open up the pores of the metal tubular much better than in conventional cleaning, allowing for a more thorough clean. In addition, the high rotational speed of the tubular during cleaning operations allows for a thorough clean without a spiral effect even though cleaning may optionally be done in one pass.

Focusing now on the disclosed MLI as a whole, it is therefore a technical advantage of the disclosed MLI to clean the interior of pipe efficiently and effectively. By extending and retracting interchangeable tooling on multiple lances into and out of a stationary but rotating tubular, considerable improvement is available for speed and quality of internal cleaning of the tubular over conventional methods and structure.

A further technical advantage of the disclosed MLI is to reduce the footprint required for industrial tabular cleaning. By extending and retracting lances into and out of a stationary tubular, reduced footprint size is available over conventional cleaning systems that move a tubular over stationary cleaning apparatus. Some embodiments of the MLI may be deployed on mobile cleaning systems.

A further technical advantage of the disclosed MLI is to enhance the scope, quality and reliability of inspection of the interior of the tubular before, during or after cleaning operations. Data acquisition structure may be deployed on one or more of the extendable or retractable lances. Such data acquisition structure may scan or nondestructively examine the interior of the tubular, either while the tubular is rotating or otherwise. Such data acquisition structure may include sensors, specialized visual inspection probes (such as video cameras), and/or thermal imaging probes.

Focusing now on the disclosed KJL, technical advantages of features of the KJL as described in this disclosure are itemized above in association with the individual KJL feature(s) to which the technical advantages pertain. The KJL also provides technical advantages overall as an assembled lance. For example, the simplicity of the disclosed KJL design enables users to concatenate KJL segments with threaded trunnions quickly and easily in order to assemble a KJL of desired length. Simple assembly and disassembly facilitates maintenance and repair. The "modular" aspect of the KJL segment design allows damaged segments to be easily replaced. The KJL as a whole may be made from a variety of materials to suit the requirements of the application. Material choice may be made according to user requirements as to, for example, chemical compatibility, KJL assembly strength, KJL length, diameter, reel dimensions (if applicable), axial compression load capacity, user budget, etc.

A core advantage of the KJL described in this disclosure, however, is its design of a lance that is rigid in compression, allowing the lance to be driven or pushed forward when extended in both horizontal and vertical applications. At the same time, the disclosed KJL is flexible in a transverse direction, allowing the lance to be stored compactly on a reel, for example. The KJL features described in this disclosure enabling compressive/torsional strength in the extension and retraction direction, while at the same time providing unstressed spooled storage for both the KJL itself and the hoses/cables inside the KJL, together combine to provide a lance system having many industrial applications.

As a result, a fully-assembled KJL (with hoses and cables on board) may be a relatively heavy apparatus and yet may be extended using a compressive force only. Other known designs of flexible lances need have poor compressive performance, and need to be pulled forward to be extended. The disclosed KJL thus optimizes the power required to extend or retract the lance, freeing up onsite power for other operations such as cutting, drilling or cleaning.

Other lances that are rigid cannot coil/spool up and they do not have flexible capability. However, the KJL does have the unique ability to spool up with zero fatigue stresses, while at the same time can layout horizontally, vertically with rigidity in compression, tension, and torsional strength. This allows the KJL to be used in applications far beyond other lancing systems.

The flexible'aspect of the disclosed KJL has been discussed so far primarily in association with optional storage on a reel. However, the flexible aspect has other applications. A KJL as disclosed herein may be extended into a work environment requiring the KJL to pass through curves, bends drops, and rises, etc. Embodiments providing the KJL features described above ensure that hoses and cables inside the KJL are exposed to minimal compression, torsion or bending loads, making the system safer and longer-lasting without fatigue to the hoses and cables.

Discussion so far in this disclosure has focused on the KJL's performance in response to compression and torsion loads. The scope of the disclosed KJL is not limited in this regard. The disclosed KJL is also strong in response to tension (pulling) loads, in both straight and curved modes. The tension load capacity of a KJL will depend on user-selected parameters such its size/dimensions, material thickness and material properties. This high tension load pulling capacity allows for the use in applications such as downhole fishing and retrieval, for example.

Discussion in this disclosure so far has also focused on the torque capacity and torsional rigidity/strength of the disclosed KJL in applications in which the KJL is deployed in a rotating tubular, for example. However, the scope of the disclosed KJL is not limited in this regard. The disclosed KJL is also advantageous in applications in which the KJL provides a rotating/spinning head attachments at a distal end thereof, where such rotating/spinning head attachments also require the KJL to display good torque capacity and torsional strength.

Discussion in this disclosure so far has also focused on KJL embodiments in which the KJL segments are hollow, and may carry hoses or cables inside, for example, in order to supply tools or instruments provided on a distal end of the KJL. However, the scope of the disclosed KJL is not limited in this regard. Embodiments of the disclosed KJL may be solid, or partially solid, in applications where remote tool supply is not a requirement of the KJL. A solid or partially solid KJL will provide excellent compression, tension, torsion and bending strength, and is highly advantageous in applications where flexible lance with high rigidity is needed with such strengths.

As noted above in this Summary section, the KJL described in this disclosure has broad industrial applications, and the scope of this disclosure is not limited to the exemplary tubular cleaning/inspection embodiments described herein. Other applications include, just for example, down hole drilling, production, downhole fishing and retrieval, horizontal pipeline, sub-sea ROV and municipal pipeline/sewer applications.

Many KJL embodiments described in this disclosure are characterized for use in association with a reel. As noted above, preferred KJL embodiments may be spooled onto a reel to allow compact KJL storage with a corresponding long KJL reach. However, embodiments of the KJL may alternatively be attached to a drill string, for example, in shorter reach applications. In such shorter reach applications, the KJL may not need the use of a spooling reel. The KJL may be assembled/disassembled and attached to the drill string rather than coiled/spooled onto a reel. The KJL segments and trunnions may be shipped in compact containers and then assembled/disassembled onsite. The length or reach of a KJL according to the disclosed design is highly variable, and may be selected to be long or short per application requirements.

Some embodiments of the enhanced KJL described in this disclosure therefore comprise a segmented lance, the lance including a plurality of connected KJL segments in a concatenated string thereof; wherein each KJL segment is generally elongate and tubular, has a longitudinal axis, and has first and second ends; and wherein, for each neighboring pair of KJL segments in the concatenated string: (1) the first end of one KJL segment in the pair is rotatably connected to the second end of the other KJL segment in the pair via a pinned connection such that when the pair of KJL segments is substantially aligned along a common longitudinal axis, the KJL segments are restrained from relative rotation about the pinned connection except in a first rotational direction only; and (2) the first end of one KJL segment in the pair provides a first sloped portion, the first sloped portion facing a second sloped portion provided on the second end of the other KJL segment in the pair, such that contact between the first and second sloped portions limits relative rotation of the KJL segments about the pinned connection in the first rotational direction to a preselected combined angular deflection; and wherein, responsive to user assignment of a predetermined length to each KJL segment in the concatenated string according to the KJL segment's corresponding pre-ordained position in the concatenated string, the lance is disposed to spool onto a reel such that as the lance makes spooling revolutions onto the reel, (a) KJL segments stack in circumferential registered layers around the reel and (b) pinned connections trace substantially radial vectors from a center of the reel.

In other embodiments, the lance makes at least two spooling revolutions onto the reel before KJL segments increment a further stacked circumferential registered layer thereof.

In other embodiments, for at least one neighboring pair of KJL segments, the first end on one KJL segment and the second end on the other KJL segment together provide an interlocking toothed connection such that the interlocking toothed connection restrains relative torsional displacement between the pair of KJL segments about the longitudinal axes of the KJL segments. The interlocking toothed connection may preferably be in substantially full interlocking enmeshment when the pair of KJL segments is substantially aligned along a common longitudinal axis. The interlocking toothed connection may further preferably be in at least partial interlocking enmeshment when the first and second sloped surfaces make contact.

In other embodiments, first selected KJL segments each provide a spooling notch wherein, when inner and outer neighboring layers of KJL segments are stacked in register on the reel: (a) the interlocking toothed connection on each KJL on the inner layer provides at least one protruding tooth, and (b) protruding teeth on the inner layer are received into spooling notches on the outer layer.

In other embodiments, the pinned connections in second selected neighboring pairs of KJL segments further include: two opposing ears extending from the second end of one KJL segment, each ear providing one ear hole, each ear further providing an ear ledge at a distal end thereof; two opposing ear cutouts in the first end of the other KJL segment, each ear cutout providing one trunnion hole, each ear cutout further providing an ear ledge recess formed therein; a pair of trunnions, each trunnion received through a corresponding ear hole and fixed into a corresponding trunnion hole when the ears are received over the ear cutouts; wherein each ear ledge recess is configured and shaped to slidably receive a corresponding ear ledge when the trunnions are received through the ear holes and fixed into the trunnion holes; and wherein the ear ledges and ear ledge recesses cooperate to restrain displacement of the ears with respect to the ear cutouts except for relative rotation between the ears and the ear cutouts about the pinned connection. The ear ledges may preferably be retained by the ear ledge recesses at all times. The ear ledge recesses may further have a preselected depth, and in which the ear ledges are at all times received into the ear ledge recesses at depths that are less than the preselected depth.

In other embodiments, for third selected neighboring pairs of KJL segments, at least of one of (a) the first end on one KJL segment in each pair, and (b) the second end on the other KJL segment in each pair, provides a wall thickness taper.

The foregoing has outlined rather broadly some of the features and technical advantages of the disclosed technology in order that the detailed description that follows may be better understood. Additional features and advantages will be described hereinafter. It should be appreciated by those skilled in the art that the conception and the specific embodiments described herein may be readily utilized as a basis for modifying or designing other structures for carrying out the same purposes of the disclosed technology. It should be also be realized by those skilled in the art that such equivalent constructions do not depart from the spirit and scope of the disclosed technology as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which:

FIG. 1 is a functional cross-section view of aspects of one embodiment of the KJL;

FIG. 2 is a cross-section view as shown on FIG. 1;

FIGS. 8, 9, 10 and 11 illustrate aspects and features of embodiments of KJL assemblies 103;

FIGS. 14, 15, 16, 17, 18, 19, 20 and 21 illustrate aspects and features of embodiments of MLG assemblies 150;

FIGS. 26, 27 and 28 are views of aspects of an embodiment of MLR axle assembly $193_M$, in which FIG. 27 illustrates axle 161 on FIG. 26 in isolation, and in which FIG. 28 is a section view as shown on FIG. 26;

FIG. 29 is a general isometric view of two neighboring, conjoined KJL segments 203 included in an alternative embodiment KJL 200;

FIG. 30 is a section as shown on FIG. 29;

FIGS. 31A and 31B are elevation views of KJL segments 203 in curved and straight modes respectively;

FIG. 32 is a top view of FIG. 31B;

FIG. 33 is a section as shown on FIG. 32;

FIG. 34 is an isometric view of FIG. 29 from underneath;

FIG. 35 is an enlargement as shown on FIG. 34;

FIG. 36 is an elevation view similar to FIG. 31;

FIG. 37 is a section as shown on FIG. 36;

DETAILED DESCRIPTION

Figure 3:
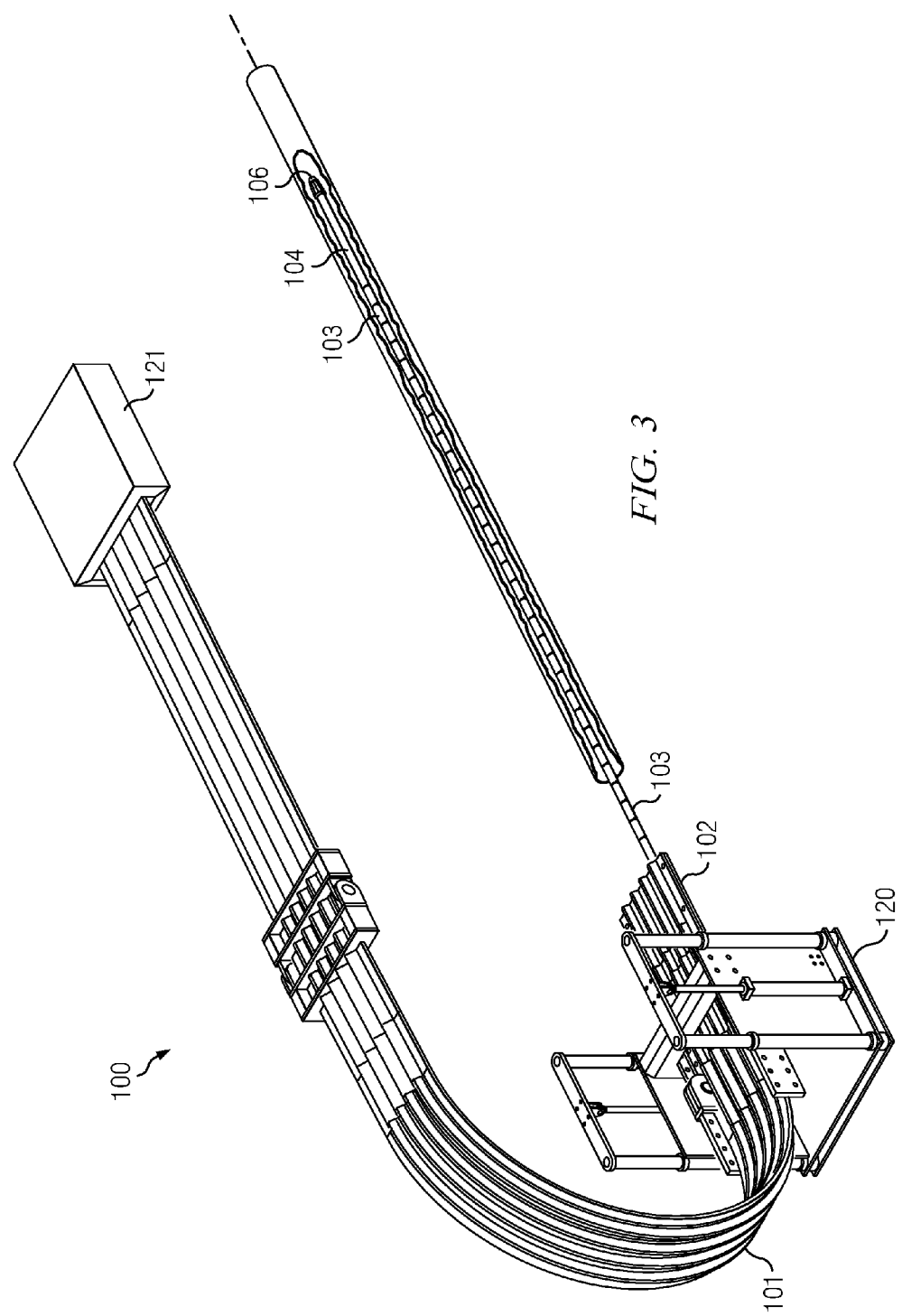
FIG. 3 is an isometric view of aspects of embodiments of the MLI.

Reference is now made to FIGS. 1 through 13 and FIGS. 8 through 11 in describing the currently preferred embodiment of the MLI.

It will be understood that the MLI, in a currently preferred embodiment, has a number of cooperating parts and mechanisms, including the Knuckle Jointed Lance (KJL). FIGS. 1 and 2 are a functional cross-sectional representation of some of the main components included in a currently preferred embodiment of the MLI, and depict bow such components cooperate in the MLI assembly. As functional representations, they will be understood not to be to scale even in a general sense. Rather, it will be appreciated that a primary purpose of FIGS. 1 and 2 is to illustrate cooperating aspects of the MLI in a conceptual sense (rather in a more structurally accurate sense), in order to facilitate better understanding of other, more structurally accurate illustrations of the MLI and KJL in this disclosure.

FIG. 1 illustrates MLI assembly 100 generally in cross-section, and depicts MLI assembly as generally comprising guide tube 101, stabbing guide tube 102, Knuckle-Jointed Lance (hereafter "KJL") 103, stinger 104, hose 105, tooling head 106 and stabbing wheels 107. In FIG. 1, MLI assembly is shown operable to clean the internal, surface of tubular W. Tubular W is shown on FIG. 1 as longitudinally stationary but rotating, per earlier material in this disclosure.

With further reference to FIG. 1, KJL 103 provides stinger and tooling head 106 at one end. KJL is operable to be "stabbed" into and out of rotating tubular W. It will be understood that by stabbing KJL 103 in and out of the entire internal length of rotating tubular W while tubular W rotates, MLI assembly 100 enables cleaning tools and other functional devices on tooling head 106 (such tools and devices not individually illustrated on FIG. 1) to clean, inspect, sense or otherwise perform work on the entire internal length of tubular W.

Stabbing wheels 107 on FIG. 1 enable KJL 103 to be stabbed in and out of tubular W. It will be appreciated from FIG. 1 that guide tube 101 and stabbing guide 102 generally encase KJL 103 up until the general area where stinger 104 and tooling head 106 lead the "stabbing" (that is, the extension and refraction) of KJL 103 into and out of tubular W. Stabbing guide 102 provides gaps G where the outside surface of KJL 103 is exposed. In one embodiment, gaps G are rectangular openings in stabbing guide 102, although this disclosure is not limited in this regard. Directional arrows 108A and 108B on FIG. 1 represent where stabbing wheels 107 are operable to be moved together and apart so that, via gaps G, the circumferences (or "treads") of stabbing wheels 107 can engage and disengage the outer surface of KJL 103 on opposing sides. Thus, when stabbing wheels 107 are engaged on the outer surface of KJL 103 and rotated, per directional arrows 109A and 109B on FIG. 1, they become operable to move KJL 103 per directional arrow 110.

With further reference to FIG. 1, KJL 103 and stinger 104 encase hose 105. Hose 105 on FIG. 1 is a functional representation of any type of flexible supply that tooling on tooling head 106 may require, such as, purely for example, steam hoses, water hoses, air hoses, nitrogen gas hoses, or conduits comprising electrical power supply cords, data transfer wiring, solid conductors, coils or antennae. Nothing in this disclosure shall be interpreted to limit hose 105 to any particular type of flexible supply or combination thereof.

Discussing hose 105 in more detail, in currently preferred embodiments, the hoses are designed and manufactured for extended life in high temperature and high pressure service, and further comprise a customized armor system for protection on the outside, including an outer co-flex, stainless steel wall with flexible steel armoring and rigidity packing. The rigidity packing uses heat-shrinking material to form a solid ID-OD fusion bond in the hoses, while also filling the void between the outer armor system and the specially-designed high temperature and high pressure hoses. It will be appreciated, however that these hose specifications are exemplary only, and that nothing in this disclosure should be interpreted to limit hose 105 on FIG. 1 to a particular specification.

It will be further understood that in embodiments where hoses 105 are specified per the example above for extended hose service life, the cost per unit length of the high-specification hose is significantly higher than the corresponding cost of conventional hose. In order to optimize this increased cost, hose 105 on FIG. 1 may, in some alternative embodiments, provide a connector separating a portion of conventional hose from a portion of higher specification hose. Advantageously, the portion of high-specification hose is positioned within KJL 103 and stinger 104 at the distal end thereof, connected to tooling head 106, and is long enough so that when KJL 103 is extended all the way to the very far (distal) end of tubular W, the entire length of tubular W is served by high-specification hose. The remaining portion of hose 105 will then be understood to be resident in the portion of KJL 103 that remains in guide tube 101 even when KJL 103 is extended all the way to the very far end of tubular W. This remaining portion of hose 105 may be deployed, as conventional hose since it is not subject to the rigors of service within tubular W.

Although FIG. 1 illustrates a single hose 105 deployed in KJL 103, it will be appreciated that this disclosure is not limited to any particular number of hoses 105 that may be deployed in a single KJL 103. Multiple hoses 105 may be deployed in a single KJL 103, according to user selection and within the capacity of a particular size of KJL 103 to carry such multiple hoses 105. This "multiple hose 105 per KJL 103" aspect of MLI 100 is described in greater detail further on in this disclosure, with reference to FIG. 14.

With reference now to graphical separator A-A on FIG. 1, it will be appreciated that the portion of KJL 103 to the right of A-A on FIG. 1 is in cross-section, while the portion to the left is not. FIG. 1, to the left of graphical separator A-A, thus illustrates that a portion of the length of KJL 103 comprises a concatenated and articulated series of hollow, generally trapezoidal KJL segments 111. KJL segments 111 (and their generally trapezoidal profile) will be described in detail further on in this disclosure. In particular, FIGS. 29 through 43 below illustrate advantageous features of the design of currently-preferred embodiments of an alternative embodiment KJL 200. The discussion of FIGS. 29 through 43 below highlights these advantageous features with reference to enhanced-design KJL segments 203 as shown on those Figures. However, with reference to FIG. 1, it will be seen that in general the concatenated, articulated nature and general trapezoidal profile of KJL segments 111 allow KJL 103, when the distal end thereof is being stabbed in and out of tubular W, to correspondingly slide around curved portions of guide tube 101 with reduced bending stress.

FIG. 2 is a cross-sectional view as shown on FIG. 1. Items depicted in both FIGS. 1 and 2 have the same numeral.

It will be immediately seen on FIG. 2 that, consistent with earlier material in this disclosure, a preferred embodiment of MLI assembly 100 provides 4 (four) separate and independent lances for cleaning, inspection, data acquisition and related operations (although as noted above, nothing in this disclosure should be construed to limit MLI assembly 100 to four lances). On FIG. 2, stabbing guide 102 includes upper and lower stabbing guide pieces 102U and 102L, which may be held together by conventional fasteners such as bolts and nuts. Stabbing guide 102 further encases 4 (four) separate KJL 103 assemblies. Each KJL 103 encases a hose 105. It will be understood that KJL 103, stinger 104 (not illustrated on FIG. 2), hose 105 and tooling head 106 (also not illustrated on FIG. 2) are functionally the same for each of the 4 (four) lance deployments illustrated on FIG. 2. It will be further appreciated that the disclosure above associated with FIG. 1 directed to extension and retraction of a single KJL 103 applies in analogous fashion to additional KJL assemblies 103 deployed on a particular embodiment of MLI assembly 100.

As also mentioned above with reference to FIG. 1, it will be appreciated that although FIG. 2 illustrates a single hose 105 deployed in each KJL 103, it will be appreciated that this disclosure is not limited to any particular number of hoses 105 that may be deployed in any single KJL 103. Multiple hoses 105 may be deployed in any single KJL 103, according to user selection and within the capacity of a particular size of KJL 103 to carry such multiple hoses 105. This multi-hose 105 and multi-size KJL 103 aspect of MLI 100 is described in greater detail further on in this disclosure, with reference to FIG. 14.

Although not illustrated on FIGS. 1 and 2, currently preferred embodiments of guide tubes 101 and stabbing guide 102 provide a low-friction coating on the internal surface thereof. This low-friction coating assists a sliding movement of KJL 103 through guide tubes 101 and stabbing guide 102 as KJL 103 is extended and retracted into and out of tubular W.

FIG. 2 also shows stabbing wheels 107. Consistent with FIG. 1, directional arrow 108A/B on FIG. 1 represents where stabbing wheels 107 are operable to be moved together and apart so that, via gap G (not shown on FIG. 2), the circumferences (or "treads") of stabbing wheels 107 can engage and disengage the outer surface of KJL 103 on opposing sides. Directional arrows 109A and 109B on FIG. 2 represent, consistent with FIG. 1, that rotation of stabbing wheels 107 when engaged on the outer surface of KJL 103 will cause KJL 103 to extend and retract.

Directional arrow 108C on FIG. 2 represents that when stabbing wheels 107 are disengaged, stabbing guide 102 (or, in other embodiments, stabbing wheels 107) is/are further operable to be moved laterally to bring any available KJL 103, according to user selection, between stabbing wheels 107. In this way, any available KJL 103, according to user selection, may be called up for engagement by stabbing wheels 107 and subsequent extension into and retraction out of tubular W.

Directional arrows H and V on FIG. 2 represent generally that the entire MLI assembly 100 as described on FIGS. 1 and 2 may be adjusted horizontally and vertically to suit size (diameter), wall thickness and relative position of tubular W into which KJL 103 assemblies are to be inserted. Such adjustment allows MLI assembly 100 to work on a wide range of different sizes and thicknesses of tubulars W.

With reference now to FIG. 3, a more scale-accurate representation of MLI assembly 100 is illustrated. Items depicted on FIG. 3 that are also depicted on FIGS. 1 and 1B have the same numeral. FIG. 3 depicts tubular W with a partial cutout, allowing KJL 103 (with stinger 104 and tooling head 106 on the distal end of KJL 103) to be seen extending into nearly the entire length of rotating tubular W. FIG. 3 further depicts guide tube 101 and stabbing guide 102.

Adjustment assembly 120 on FIG. 3 enables the positional adjustments described above with reference to FIGS. 1 and 2. More specifically, adjustment assembly 120 includes structure that enables (1) stabbing wheels 107 to move together and apart per directional arrows 108A and 108B on FIGS. 1 and 2, (2) stabbing guide 102 to move laterally per directional arrow 108C on FIGS. 2, and (3) MLI assembly 100 to move horizontally and vertically per directional arrows H and V on FIG. 2.

Although adjustment assembly 120 (and components thereof) are illustrated and describe generally in this disclosure, it will be appreciated that the specifics of adjustment assembly 120, and the control thereof, rely on conventional hydraulic, pneumatic or electrical apparatus, much of which has been omitted from this disclosure for clarity.

FIG. 3 further illustrates hose box 121. It will be appreciated that as KJL assemblies 103 are fully extended all the way to the distal end of tubular W, and then retracted all the way out of tubular W, corresponding hoses 105 deployed inside KJL assemblies 103 require surplus length to accommodate such extension and retraction. Hose box 121 is a containment box for such surplus lengths of hoses 105.

Figure 4:
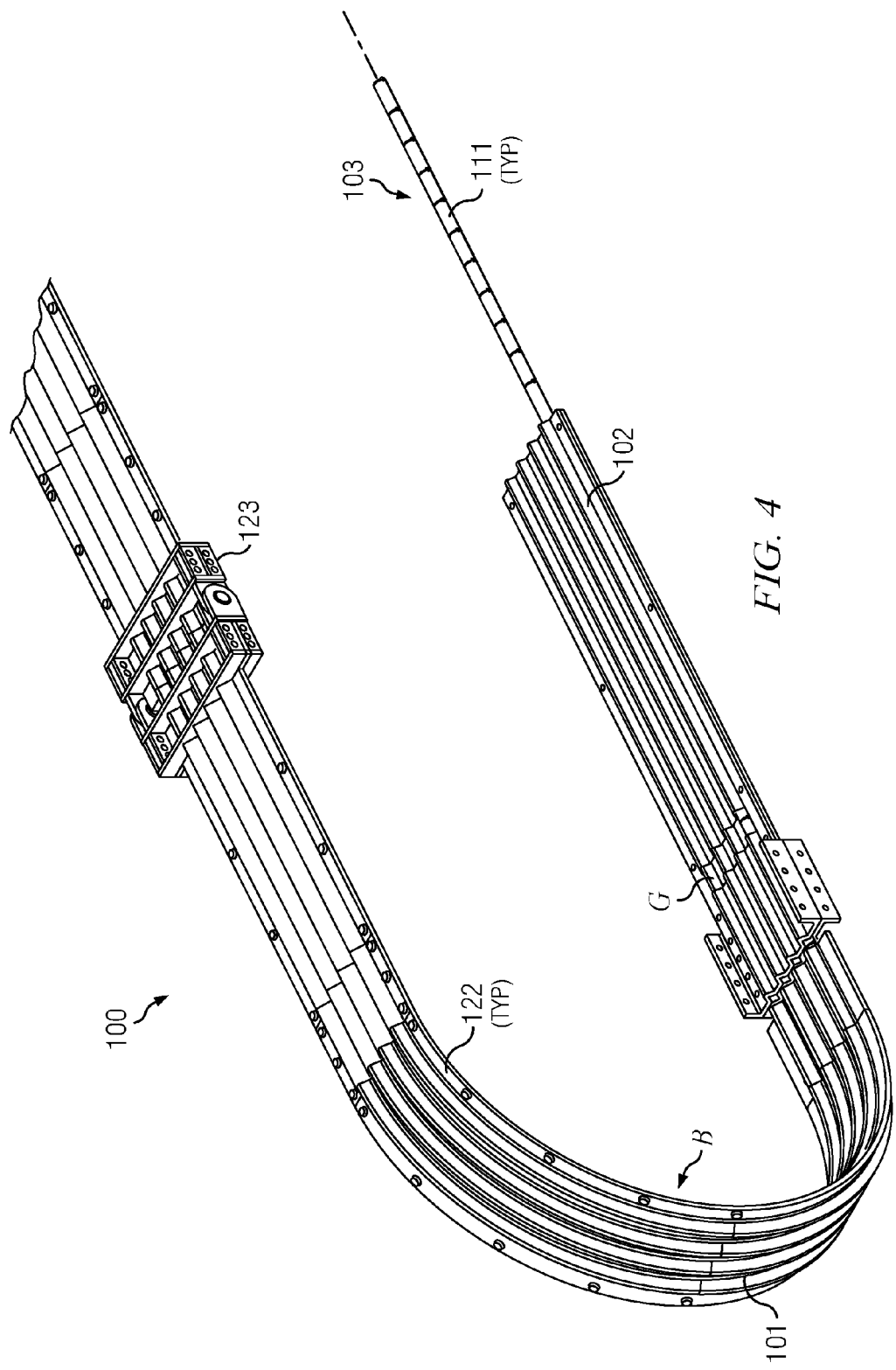
FIG. 4 is a general enlargement of MLI assembly 100 as illustrated on FIG. 3.

FIG. 4 is a general enlargement of MLI assembly 100 as illustrated on FIG. 3, particularly in the area around stabbing guide 102. Adjustment assembly 120 and tubular W FIG. 3 have been omitted on FIG. 4 for clarity. As in other illustrations in this disclosure depicting aspects of MLI assembly 100, items depicted on FIG. 4 that are also depicted on FIGS. 1, 2 and/or 3 have the same numeral.

FIG. 4 illustrates stabbing guide 102 with one exemplary KJL 103 extended. Gaps G from FIG. 1 can, also be seen on stabbing guide 102 on FIG. 4. It will be recalled from earlier disclosure describing FIG. 1 that the "treads" of stabbing wheels 107 (not shown on FIG. 4) contact the outer surface of KJL assemblies 103 through gaps G to enable, via rotation of stabbing wheels 107, extension and/or retraction of KJL assemblies 103.

FIG. 4 further illustrates guide tubes 101 as assemblies operable to be disassembled and reassembled. This aspect of guide tubes 101 enables, in part, MLI assembly 100 to be configured in either "curved" mode (as illustrated on FIG. 4) or "straight" mode (not illustrated) as further described below. It will be seen on FIG. 4 that in currently preferred embodiments, guide tubes 101 are separable along their travelling horizontal axis (or thereabouts) and are further operably held together during service with guide tube fasteners 122. Longitudinal sections of guide tubes 103 are further separable at guide tubes joints 123 (only one exemplary guide tube joint 123 fully illustrated on FIG. 4).

It will be seen from FIG. 4 that optimization of footprint of MLI assembly 100 may be assisted by deploying guide tubes 101 as illustrated in FIG. 4, with guide tubes 101 undergoing a u-turn of approximately 180 degrees at bend B during their travel. Although also not illustrated in FIG. 4, nothing in this disclosure should be construed to limit bend B to a u-turn of 180 degrees or thereabouts. Other angles of bend B are considered within the scope of this disclosure.

Other embodiments of the MLI assembly 100 (such other embodiments not illustrated) provide guide tubes 101 substantially straight extending substantially horizontally up to the entrance to tubular W, and substantially parallel to the longitudinal axis of tubular W. It will be appreciated that such straight mode embodiments will require additional footprint. Some of such straight mode embodiments may also substitute rigid pipes for KJL assemblies 103. With momentary reference to FIG. 1, rigid pipes in straight mode embodiments (not illustrated) will surround hoses 105 instead of KJL assemblies 103 and stingers 104, and will further connect directly to tooling heads 106. It will be appreciated that extension and retraction of the rigid pipes may then be enabled via stabbing wheels 107 operating on the exterior surfaces of rigid pipes through gaps G in stabbing guide 102, per FIG. 1).

Figure 5:
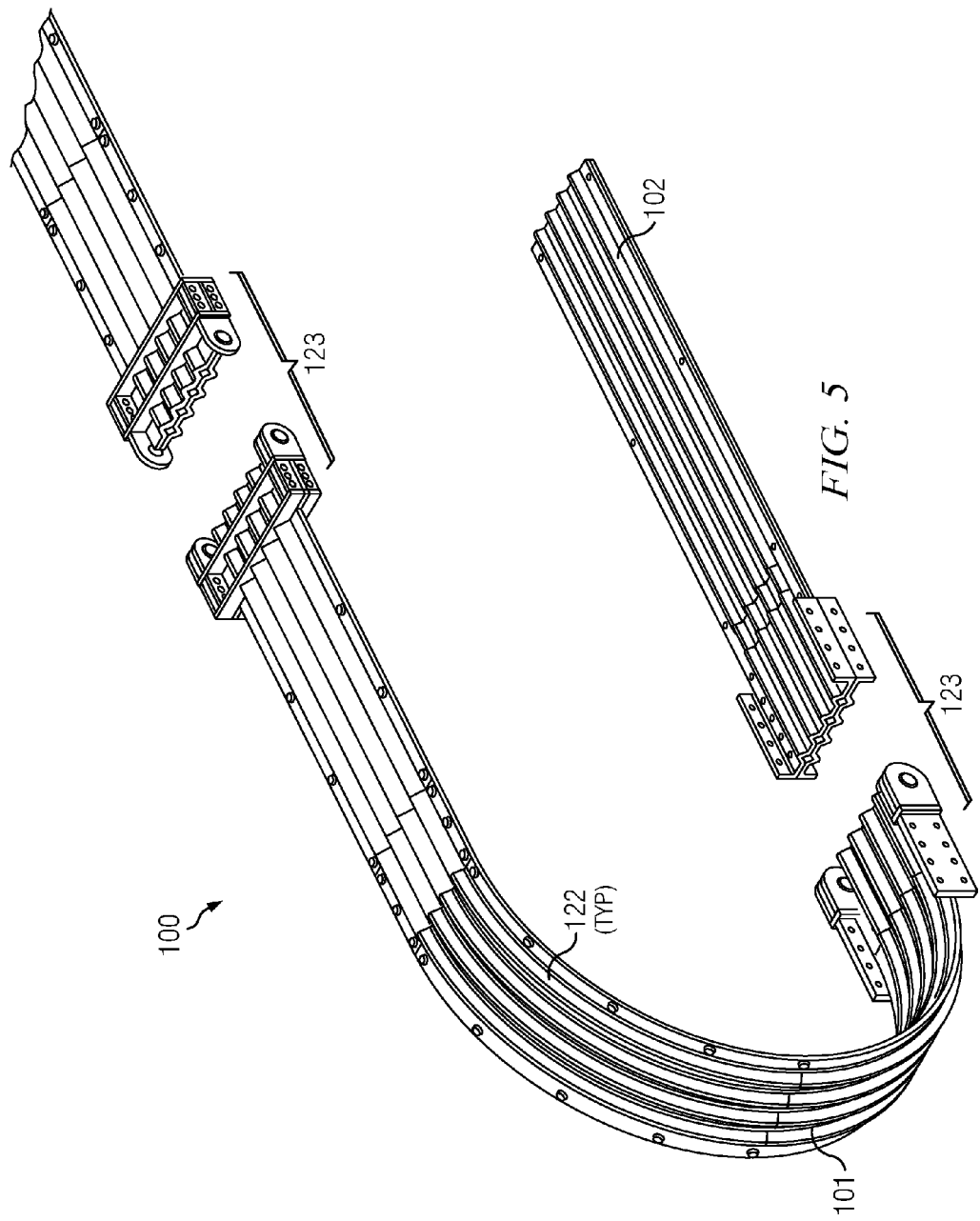
FIGS. 5 and 6 are exploded views of aspects also illustrated on FIG. 4.
Figure 6:
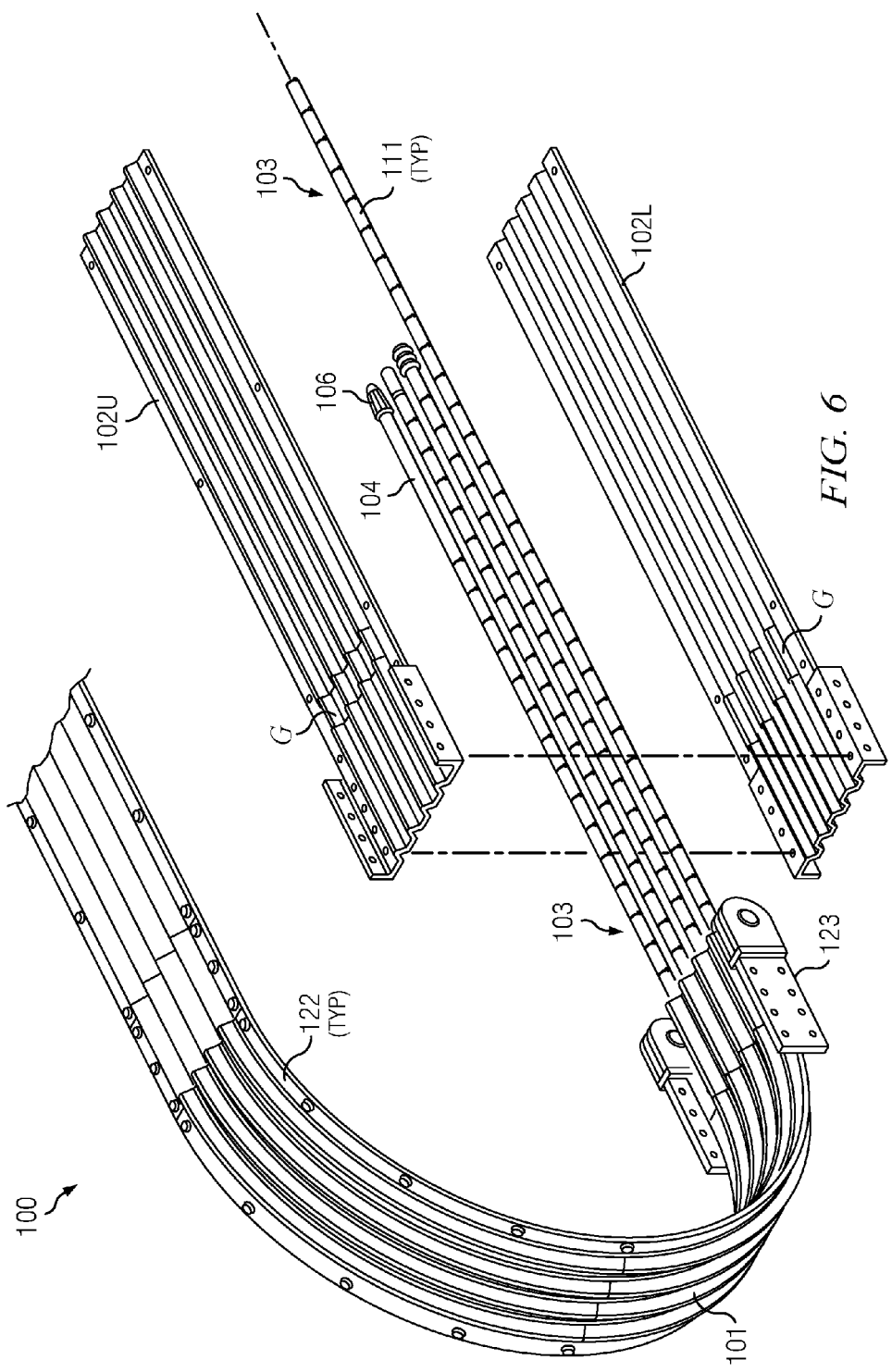

With reference now to FIGS. 5 and 6, guide tubes 101 and stabbing guide 102 are shown in partially "exploded" form in order to illustrate how certain embodiments of MLI assembly 100, now to be illustrated and described in more detail, may be "converted" back and forth, per user selection, between curved mode (as illustrated in FIG. 4), and straight mode as described above although not illustrated. As before, items depicted on FIGS. 5 and 6 that are also depicted on FIGS. 1 through 4 have the same numeral.

It will be recalled from earlier disclosure referring to FIG. 4 that "convertible" embodiments of MLI assembly 100 provide guide tubes 101 operable to be disassembled and reassembled in order to convert between curved and straight modes. FIG. 5 illustrates MLI assembly 100 in curved mode, with guide tube 101 and stabbing guide 102 disassembled at guide tube joints 123. It will be seen in the exemplary embodiment illustrated on FIG. 5 that two guide tube joints 123 are provided, one at the connection between guide tubes 101 and stabbing guide 102, and the other at a connection between pieces of guide tubes 101 above stabbing guide 102. It will be nonetheless understood that the number and location of guide tube joints 123 illustrated on FIG. 5 are exemplary only. Nothing in this disclosure should be interpreted to limit MLI assembly 101 to any particular number or location of guide tube joints 123.

FIG. 6 illustrates MLI assembly 100 in curved mode with upper and lower stabbing guide pieces 102U and 102L separated. As noted above with reference to FIG. 4, fasteners 122 may hold sections of guide tube 101 and stabbing guide 102 together at the traveling horizontal axis thereof. In such an embodiment, fasteners 122 may be unfastened in order enable disassembly. It will be appreciated with referenced to FIG. 6 that although not illustrated, sections of guide tubes 101 may also be separated at their traveling horizontal axis by unfastening fasteners 122 in analogous fashion to the manner in which FIG. 6 illustrates stabbing guide pieces 102U and 102L as separated.

By way of reference, with FIG. 6 illustrating stabbing guide pieces 102U and 102L as separated, FIG. 6 further illustrates KJL assemblies 103, stingers 104, tooling heads 106, KJL segments 111 and gaps G in more scale-accurate fashion than on FIGS. 1 and 1B, where they were illustrated in more of a functional form.

Visualizing FIGS. 5 and 6 together, therefore, it will be appreciated that by disassembling and separating guide tubes 101 at their traveling horizontal axes per FIG. 6, and by separating pieces thereof at guide tube joints 123 per FIG. 5, guide tubes 101 may be disassembled and removed from MLI assembly 100.

Figure 7:
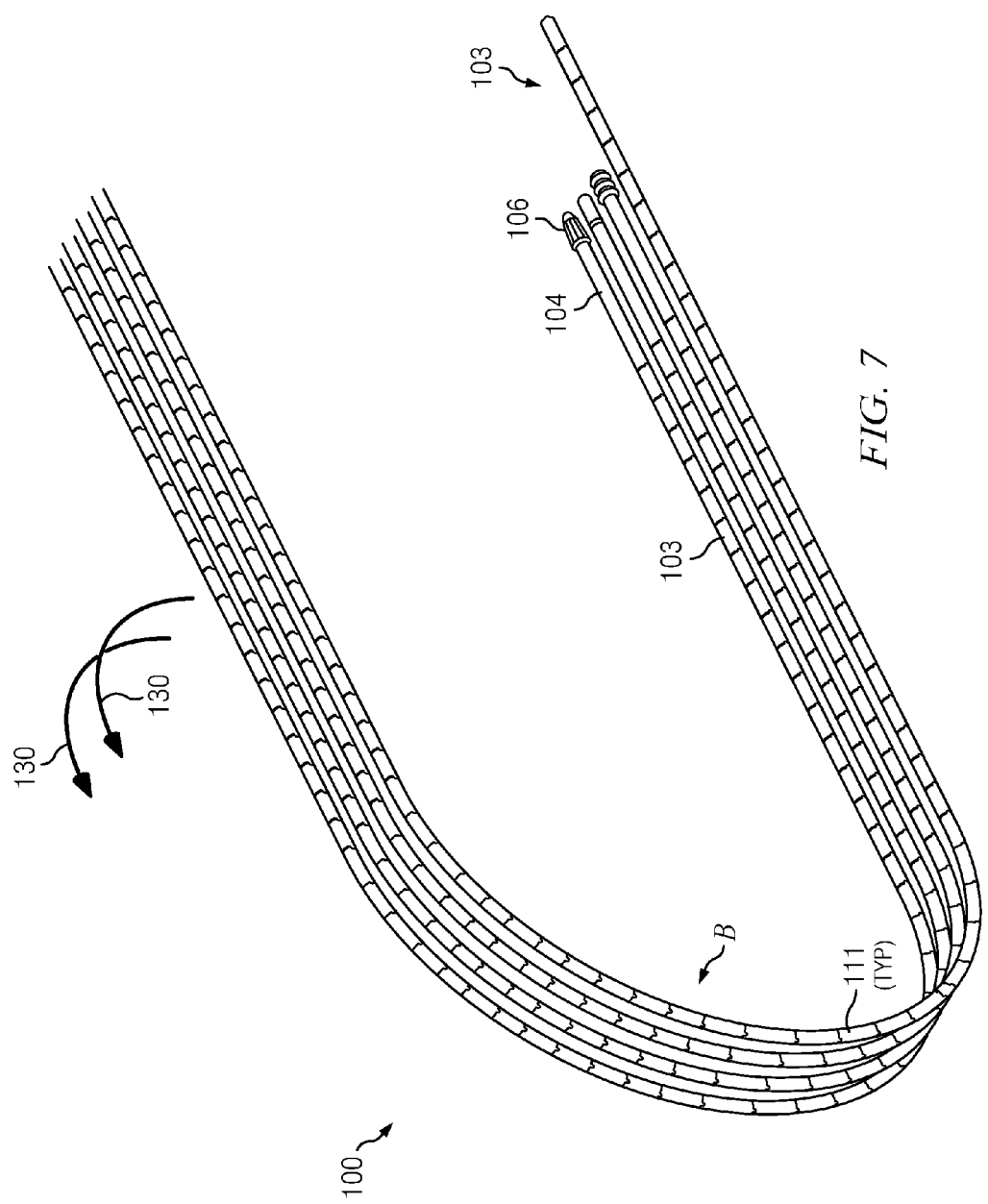
FIG. 7 is an isometric view of aspects of embodiments of KJL assemblies 103 in isolation.

Disassembly and removal of guide tubes 101 in turn exposes KJL assemblies 103 along their entire length, as illustrated on FIG. 7. As before, items depicted on FIG. 7 that are also depicted on FIGS. 1 through 6 have the same numeral. FIG. 7 further illustrates KJL assemblies 103 comprising KJL segments 111. In more detail, it will be recalled from earlier disclosure with reference to FIG. 1 that KJL assemblies 103 each comprise a concatenated and articulated series of hollow, generally trapezoidal KJL segments 111. FIGS. 29 through 43 below illustrate advantageous features on currently-preferred embodiments of KJL 200 (an alternative embodiment of KJL assembly 103 on FIG. 1), including with reference to enhanced-design KJL segments 203.

Referring back now to the general "conversion" procedure between curved and straight modes, it will be appreciated that FIG. 7 illustrates KJL assemblies 103 in curved mode. It will be further visualized from FIG. 7 that by following directional arrows 130, the articulated, generally trapezoidal nature of concatenated KJL segments 111 enables KJL assemblies 103 to be laid out horizontally straight from their previous curved mode configuration (per FIG. 7) once guide tubes 101 are disassembled and removed. It will be then understood that KJL assemblies 103 will be in straight mode configuration once laid out straight and horizontal. Rigid pipes (per earlier disclosure) or straight guide tubes in pieces (not illustrated) may then be installed around straight and horizontal KJL assemblies 103. MLI assembly 100 will then be in straight mode.

It will be appreciated that conversion back to curved mode requires generally the reverse process. KJL assemblies 103, in straight and horizontal configuration are exposed by removal of their surrounding rigid pipes or straight guide tubes. The articulated, generally trapezoidal nature of concatenated KJL segments 111 enables KJL assemblies 103 to be "rolled over" in the opposite direction of directional arrows 130 on FIG. 7. When "rolled over" to the user-desired bend B (per FIG. 7), KJL assemblies 103 will be in a curved mode configuration. Guide tubes 101 may be reassembled around KJL assemblies 103 per the reverse of the disassembly process described above with reference to FIGS. 5 and 6. MLI assembly 101 will then be curved mode again.

FIGS. 8 and 9 illustrate, in conceptual and functional form, the preceding two paragraphs' disclosure of the currently preferred embodiment of "conversion" back and forth, per user selection, of curved and straight modes. As before, items on FIGS. 8 and 9 also shown on FIGS. 1 through 7 have the same numeral. On FIG. 8, with further reference to FIG. 7, MLI assembly 100 is in curved mode with KJL 103 curved around bend B. Stinger 104 and tooling head 106 are shown conceptually on FIGS. 8 and 9 for reference. FIGS. 8 and 9 further show, again conceptually and functionally rather than to scale, that KJL 103 comprises a concatenated string of articulated, generally trapezoidal KJL segments 111.

By following directional arrow 130 on FIG. 8, KJL 103 may be laid out flat and horizontal as shown on FIG. 9. The concatenated string of articulated, generally trapezoidal KJL segments 111 enables KJL to be laid out flat and horizontal, in configuration for straight mode.

FIG. 9 further shows that by following directional arrow 130R (the reverse of directional arrow 130 on FIG. 8), KJL 103 may be "rolled up" again to form bend B, as shown on FIG. 8. The concatenated string of articulated, generally trapezoidal KJL segments 111 enables KJL 103 to be rolled up, in configuration for curved mode.

The articulated, generally trapezoidal nature of KJL segments 111 will now be discussed in greater detail. FIG. 10 illustrates one design of an individual segment 111. As before, items on FIG. 10 also shown on FIGS. 1 through 9 have the same numeral.

It will be understood that FIG. 10 illustrates just one example of a design of a KJL segment 111. Many types of individual design of KJL segments 111 are available within the scope of this disclosure, and the design of KJL segment 111 on FIG. 10 is exemplary only. Likewise, the size (diameter), number and length of individual KJL segments 111 in a particular KJL 103 may be per user design according to curvature and other geometric parameters of a particular MLI deployment. Nothing in this disclosure should be interpreted to limit the MLI to any particular length, size (diameter), number or even uniformity of KJL segments 111 that may be included in KJL 103. In particular, it should be noted that although the KJL segments 111 on KJL 103 described herein with reference to FIGS. 10 and 11 are serviceable, currently-preferred embodiments of KJL 200 (an alternative embodiment of KJL assembly 103) provide enhanced-design KJL segments 203 as described below with reference to FIGS. 29 through 43.

Referring now to FIG. 10, KJL segment 111 provides pins 139 at one end (one pin hidden from view) and lug holes 140 at the other end. By linking the pins 139 of one KJL segment 111 into the lug holes 140 of the next in line, a plurality of KJL segments 111 may be concatenated into an articulated string, as illustrated in FIGS. 8 and 9, and elsewhere in this disclosure. In other embodiments (not illustrated), trunnion holes may be substituted for pins 139. The plurality of KJL segments 111 may then be concatenated into an articulated string by securing a trunnion pin through the trunnion hole of one KJL segment 111 and the corresponding lug hole 140 of a neighboring KJL segment 111.

KJL segment 111 on FIG. 10 also has opposing longitudinal outer surfaces $111_I$ and $111_O$ which, when a plurality of KJL segments 111 are articulated together into a string thereof, will form the inner and outer surfaces of curvature respectively of the rolled-up articulated string. KJL segment 111 on FIG. 10 further provides opposing faces $111_F$. Opposing faces $111_F$ are configured to slope towards one another. This sloping is illustrated on FIG. 10 at items 141A and 141B, where the planes of faces $111_F$ are illustrated to have angular deviation from a theoretical face plane that would be normal to the longitudinal axis of the KJL segment 111. In this way, the length of KJL segment 111 is less along longitudinal surface $111_I$ than it is along longitudinal surface $111_O$. Accordingly, when a plurality of KJL segments 111 are articulated into a string such that longitudinal surfaces $111_I$ and $111_O$ line up along the string, the shorter lengths of surfaces $111_I$ permit "rolling up" where surfaces $111_I$ form the innermost surface of curvature, and surfaces $111_O$ form the outermost surfaces of curvature.

FIG. 11 illustrates KJL 103 comprising a concatenation of articulated KJL segments 111 designed per the example of FIG. 10. As before items on FIGS. 11 that are also shown on FIGS. 1 through 10 have the same numeral.

As described above with reference to FIG. 10, FIG. 11 shows that by linking the pins 139 of one KJL segment 111 into the lug holes 140 of the next in line, a plurality of KJL segments 111 may be concatenated into an articulated string. Further, the shorter lengths of longitudinal surfaces $111_I$ over longitudinal surfaces $111_O$ enable curvature when KJL 103 is "rolled up" so that surfaces $111_I$ form the innermost surface of curvature and surfaces $111_O$ form the outermost surfaces of curvature.

Figure 12:
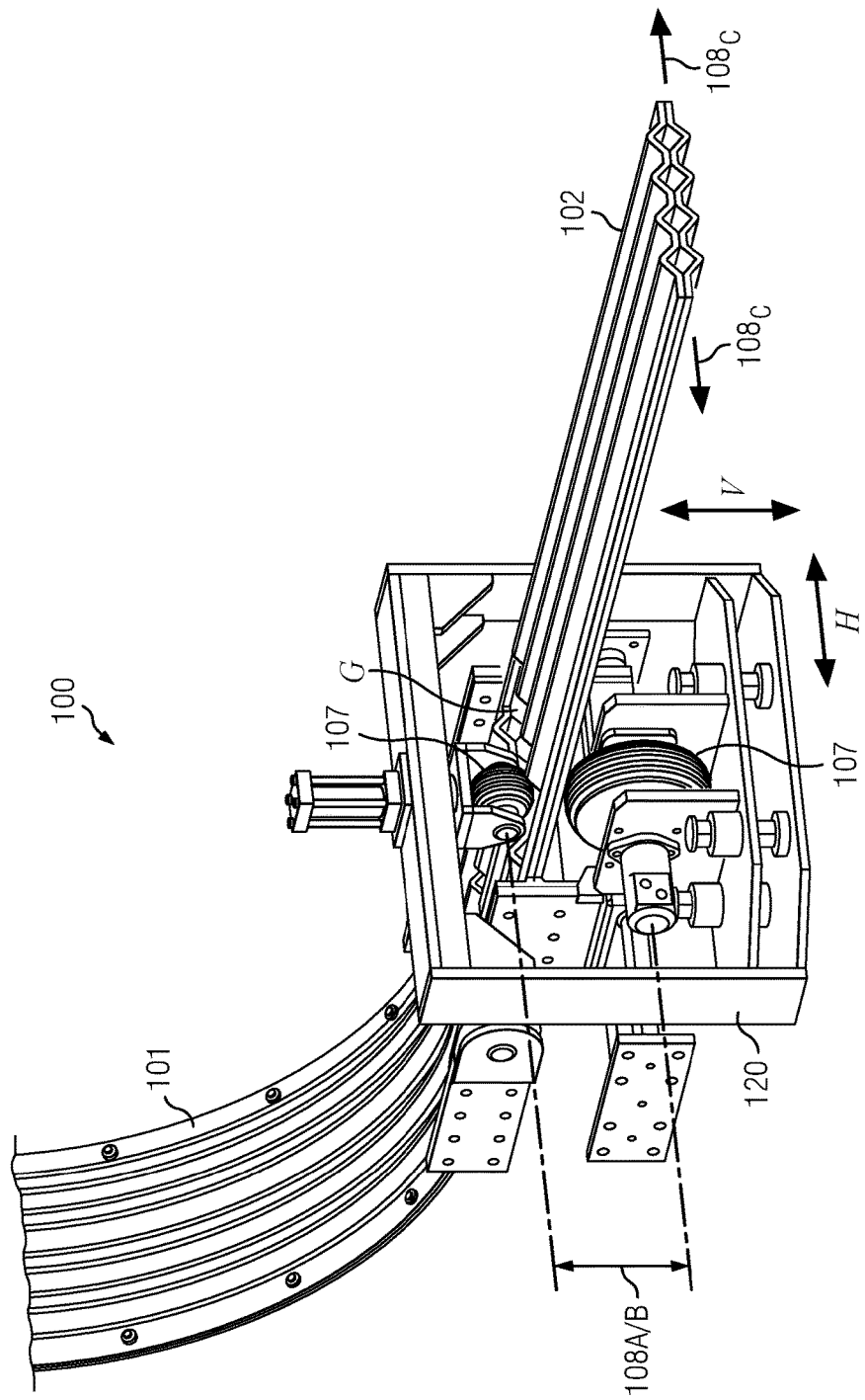
FIGS. 12 and 13 are isometric views illustrating aspects of embodiments of MLI assembly 100 and embodiments of adjustment assembly 120 in more detail.
Figure 13:
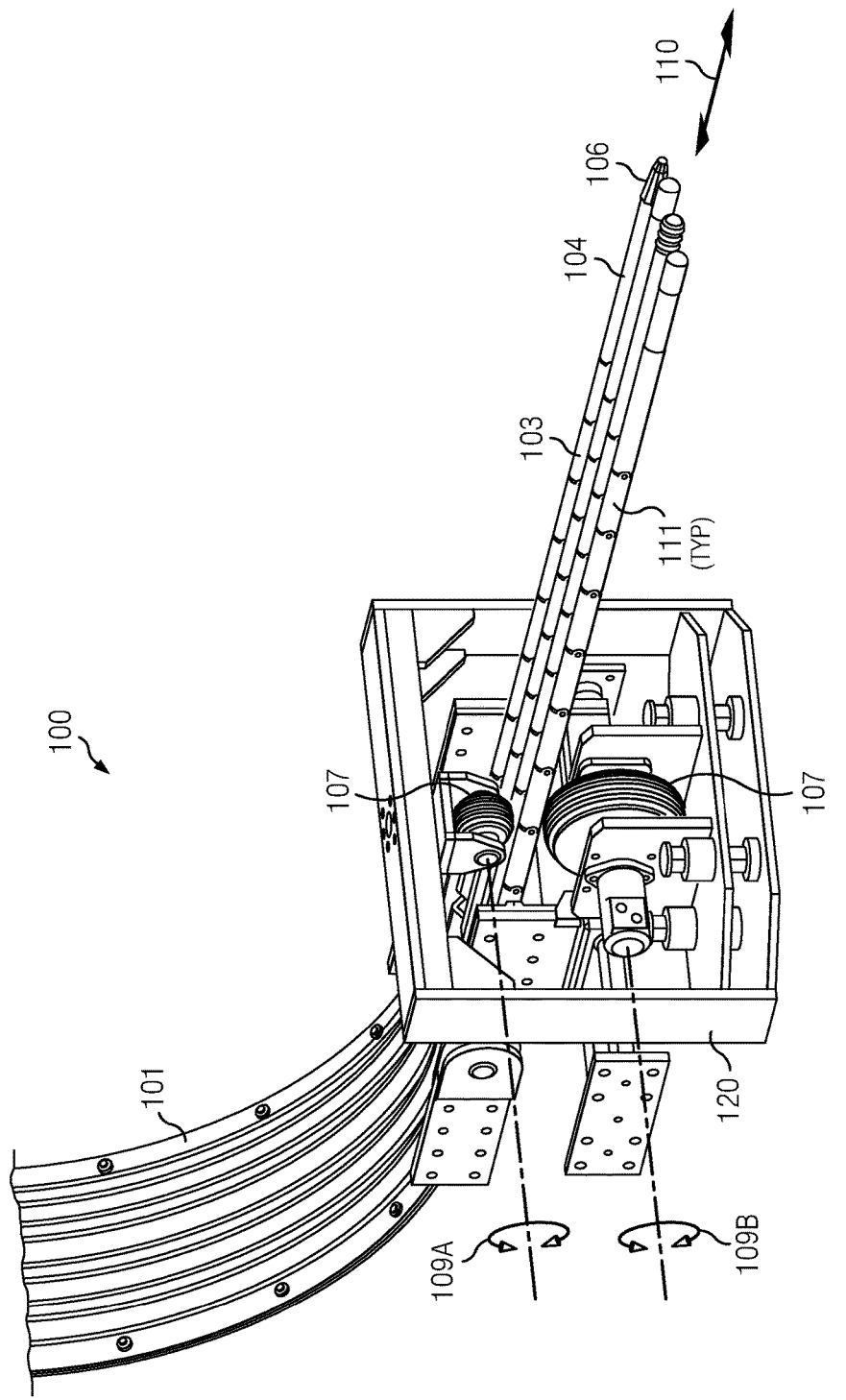

FIGS. 12 and 13 illustrate adjustment assembly 120 (also shown on FIG. 3) in more detail. As before, items shown on FIGS. 12 and 13 that are also shown on any other MLI-series or KJL-series illustration in this disclosure have the same numeral.

The primary difference between FIGS. 12 and 13 is that in FIG. 12, stabbing guide 102 is present, whereas in FIG. 13, it is removed. FIGS. 12 and 13 should be viewed in conjunction with FIGS. 1 and 2.

It will be recalled from earlier disclosure that FIGS. 1 and 2 illustrate, in a functional representation rather that a more scale-accurate representation, the operation of stabbing wheels 107 to enable extension and retraction of KJL 103 into and out of tubular W. FIGS. 1 and 2 further illustrate (again more in a functional sense than in a scale-accurate sense), by means of directional arrows 108A, 108B, 108C, 109A, 109B, 110, H and V, the manner in which stabbing wheels 107 may extend and retract KJL 103, and further, the manner in which MLI 100 may be adjusted positionally (1) to select a particular KJL 103 to be extended and retracted into and out of tubular W, and (2) to set a horizontal and vertical positions of the selected KJL 103 to suit location, diameter and wall thickness of tubular W. FIGS. 12 and 13 illustrate similar disclosure, except in a more scale-accurate representation, and further with reference to adjustment assembly 120.

Looking first at FIG. 12, it will be seen that adjustment assembly 120 comprises stabbing wheels 107. The "treads" of each stabbing wheel 107 will be understood to be engaged, through gaps G in stabbing guide 102, on the outside surface of KJL 103 (hidden from view by stabbing guide 102). Adjustment assembly 120 may move stabbing wheels 107 together and apart in the direction of arrows 108A/B as shown on FIG. 12 in order to engage/disengage KJL 103 through gaps G. Once stabbing wheels 107 are disengaged, adjustment assembly 120 may also move stabbing guide 102 (and connected guide tubes 101) laterally in the direction of arrow 108C in order to bring a selected KJL 103 into position between stabbing wheels 107 for further extension and retraction operations. Further, adjustment assembly 120 may move the entire MLI assembly 100 in this area in the direction of arrows H and V in order to suit location, diameter and wall thickness of a particular tubular W (not illustrated).

The immediately preceding paragraph disclosed that, in accordance with currently preferred embodiments of adjustment assembly 120, lateral movement of stabbing guide 102 enables a selected KJL 103 to be brought into position between stabbing wheels 107. This disclosure is not limited in this regard, however. Other embodiments of adjustment assembly 120 (not illustrated) may move stabbing wheels 107 laterally, or move both stabbing guide 102 and stabbing wheels 107 laterally, in order to bring a selected KJL 103 into position between stabbing wheels 107.

Turning now to FIG. 13, the "treads" of stabbing wheels 107 may now be seen engaged on the outer surface of KJL 103. Adjustment assembly 120 may cause stabbing wheels 107 to rotate in the direction of arrows 109A and 109B in order to extend and retract KJL 103.

It will be appreciated that, with reference to FIGS. 12 and 13, adjustment assembly 120 may be configured to extend or retract KJL assemblies 103 in a range of sizes. In fact, nothing in this disclosure should be interpreted to limit KJL assemblies 103 (and corresponding KJL segments 111) to any particular size or length. While FIGS. 1 and 2 above illustrate a single hose 105 deployed in each KJL 103, it will be appreciated that this disclosure is not limited to any particular number of hoses 105 that may be deployed in a single KJL 103. Multiple hoses 105 may be deployed in any KJL 103, according to user selection and within the capacity of a particular size of KJL 103 to carry such multiple hoses 105.

FIG. 14 illustrates an exemplary suite of 4 (four) KJL segments 111A through 111D in a range of sizes (diameters) and corresponding lengths. Each of KJL segments 111A through 111D conform to the general geometry and general concatenation concepts described above with reference to FIGS. 10 and 11. Although FIG. 14 illustrates individual, single KJL segments 111A-D, it will be appreciated that multiples of each of KJL segments 111A-D may be concatenated into KJL strings that are functionally and operationally equivalent to the KJL assemblies 103 illustrated and described elsewhere in this disclosure.

Earlier disclosure with reference to FIGS. 1 and 2 described generally the concept that multiple hoses 105 may be deployed in a single KJL 103. FIG. 14 shows that as the size (diameter) of KJL segments 111A-D increases, the corresponding internal capacity thereof increases, making a concatenated string thereof increasingly suitable to carry more than one hose 105 (hoses 105 omitted for clarity on FIG. 14).

The Scorpion System MLI contemplates a wide variety of hoses (and corresponding tooling at the distal end thereof) being available to MLI 100 for internal cleaning, inspection, data acquisition and other operations. Exemplary lances in a preferred embodiment are described above. Hoses suitable to serve such lances include (by way of example only, and without limitation): high volume air hoses for pneumatic tooling; high pressure water; steam; high temperature water; and conduits (e.g. PVC plastic) for data lines, electrical power lines, solid conductors, coils or antennae.

KJL 111A on FIG. 14 is illustrated as having the largest size (diameter) of the suite of KJL segments 111A-D. In some embodiments, KJL 111A is about 4 inches in diameter. This 4-inch diameter allows for an internal diameter with capacity to carry several hoses. The precise number capable of being carried will depend on the user's selection of diameter of hoses.

KJL segments 111B, 111C and 111D are illustrated as progressively smaller in size (diameter) than KJL segment 111A, and will, again dependent on user selection, be capable of carrying correspondingly fewer hoses each.

Generally, users are likely to select KJL size (diameter) according to the tooling intended to be deployed at the distal end of the KJL. Multiple hoses carried by a particular KJL will enable deployment of a multi-tool head at the distal end. Alternatively, multiple hoses carried in a particular KJL may be connected and disconnected to suit tooling at the distal end of the KJL as needed.

In addition to number of hoses, users are further generally likely to select KJL size (diameter) according to the size (diameter) of hose(s) intended to be carried Larger size (diameter) hoses may be preferable in long KJL assemblies in order to mitigate pressure loss and/or flow rate loss over the length of the hose. Similarly, larger size (diameter) conduits may be preferable in long KJL assemblies in order to carry larger diameter cables, which are less susceptible to voltage drop, current losses, or signal losses over greater length.

Further reference to FIG. 14 shows that in preferred embodiments, the length of KJL segments 111A-D changes inversely with respect to the size (diameter). A primary reason, again in preferred embodiments, is manufacturing economy. With reference now to FIG. 7, it will be appreciated that the manufacturing costs of a concatenated 101, assembly 103 for a particular size (diameter) will increase with the number of articulated KJL segments 111 that are deployed in the concatenated string. It is preferable, for manufacturing economy, to make the length of individual KJL segments 111 as long as possible in order to reduce the lumber of KJL segments 111 that will require concatenation. However, the concatenated string must still be able to be extended and retracted around bend B without undue bending stress.

Referring now to FIG. 14 again, it will be appreciated that the smaller the size (diameter) of KJL segments 111A-D, the more receptive to bending an individual KJL segment is likely to be when a concatenation thereof is extended and retracted around bend B (from FIG. 7). Thus, again in preferred embodiments, such smaller-sized (smaller-diameter) KJL segments may be manufactured with a longer distance between the articulations in a concatenation thereof. Hence such smaller-sized (smaller diameter) KJL segments may be manufactured to be greater in length.

As previously noted, FIG. 14 illustrates an exemplary suite of 4 (four) KJL segments 111A through 111D, in which KJL segments 111A-D decrease in size (diameter) moving from 111A though to 111D, and correspondingly increase in length. Nothing in this disclosure should be interpreted, however, to limit the Scorpion System MLI to such an arrangement. According to user selection and design, a particular deployment of the Scorpion System MLI may have any number of KJL assemblies, in any arrangement of size (diameter) and associated length. In particular, refer below to discussion accompanying FIGS. 29 through 43, in which currently preferred embodiments of KJL 200 (an alternative embodiment to KJL 103) are described with reference to enhanced-design KJL segments 203.

It will be appreciated that when the Scorpion System MLI is configured with a suite of KJL assemblies of differing size (diameter) and corresponding differing KJL segment length, guide tubes 101 and stabbing guide 102 (as illustrated on FIGS. 5 and 6, for example) may become more complex to manufacture, assemble and disassemble. Accordingly, the Scorpion System MLI provides the Multi-Lance Guide (MLG) as an optional, alternative embodiment for such deployments of multi-size KJL assemblies. In such embodiments, the MLG generally substitutes for guide tubes 101 and stabbing guide 102.

FIG. 14 illustrates Multi-Lance Guide (MLG) 150, comprising MLG tube 151 and MLG interior 152. MLG interior 152 provides MLG apertures 153 in corresponding size and number to match concatenated strings of KJL segments 111A through 111D. The diameters of each of MLG apertures 153 are pre-selected to slidably receive their corresponding concatenated string of KJL segments 111A-D, as applicable.

FIG. 15 illustrates MLG 150 where, by comparison to FIGS. 5 and 6, for example, MLG 150 will be seen to be suitable to generally substitute for guide tubes 101 and stabbing guide 102 to hold and guide KJL assemblies 103 (not illustrated on FIG. 15) during extraction and retraction operations. Nothing in this disclosure, however, should be interpreted to require (or favor) an embodiment comprising MLG 150 over an embodiment comprising guide tubes 101 and stabbing guide 102, or vice versa. This disclosure is not limiting in this regard.

As shown on FIG. 15, MLG 150 comprises MLG straight sections $150_S$, MLG curved sections $150_C$ and MLG stabbing guide $150_{SG}$. Each of $150_S$, $150_C$ and $150_{SG}$ further comprise MLG tube 151 and MLG interior 152 (or, more precisely, sections thereof). As noted immediately above with reference to FIG. 14. and as now can be seen further on FIG. 15, MLG interior 152 provides MLG apertures 153 throughout in size and number to slideably receive a corresponding suite of user-selected KJL assemblies 103 (not illustrated on FIG. 15).

FIG. 15 further shows that a plurality of MLG straight sections $150_S$ and MLG curved sections $150_C$ may be concatenated and then joined to MLG stabbing guide $150_{SG}$ to create MLG 150 per user selection and design. Concatenation of straight sections $150_S$ and curved sections $150_C$ (and then to MLG stabbing guide $150_{SG}$) may be by conventional methods, such as (for example) fastening with bolts. Such exemplary concatenation fastening apparatus has been omitted for clarity on FIG. 15 (and on other illustrations in this disclosure) for MLG straight sections $150_S$ and MLG stabbing guide $150_{SG}$, but may be seen on FIG. 15 for MLG curved sections $150_C$.

FIG. 15 further depicts gap G in MLG stabbing guide $150_{SG}$. Referring back momentarily to disclosure associated with FIG. 12, gaps G on top of and underneath MLG stabbing guide $150_{SG}$ (gap G underneath hidden from view on FIG. 15) are operable to allow stabbing wheels 107 (as shown on FIG. 12) to engage KJL assemblies 103 deployed inside MLG stabbing guide $150_{SG}$.

FIG. 15 also illustrates MLG feet 154, whose function is to enable the entire MLG 150 assembly to slide unrestrained over supporting structural steel (omitted for clarity) during Scorpion System MLI operations. It will be recalled from earlier disclosure that preferred embodiments of the Scorpion System MLI enable users to select from among two or more (and preferably four) KJL assemblies in deciding which KJL assembly to extend and retract into a tubular. It will be further recalled from disclosure associated with FIG. 12 that adjustment assembly 120 enables movement in the direction of arrows H, V and 108C in order to position a particular KJL assembly with respect to a tubular. Referring now to FIG. 15 again, it will be appreciated that sliding movement of MLG feet 154 over supporting structural steel (omitted for clarity) enables overall displacement of MLG 150 to accommodate corresponding movement and displacement when a user selects a particular KJL assembly to be positioned for extension/retraction into and out of a tubular (per FIGS. 12 and 13 and associated disclosure). MLG feet 154 may be of any conventional construction, such as (for example) ball bearings or ball races enclosed in metal or plastic housings.

FIGS. 16 and 17 illustrate MLG straight, section $150_S$ (from FIG. 15) in greater detail. As also noted above with reference to FIG. 15, conventional structure (such as bolts or other fasteners) disposed to enable concatenation of multiple MLG straight sections $150_S$ has been omitted from FIGS. 16 and 17 for clarity. FIG. 16 illustrates MLG straight section $150_S$ comprising MLG tube 151 encasing MLG interior pieces 152A and 152B (which together comprise MLG interior 152 as illustrated on FIGS. 14 and 15). FIG. 16 also depicts MLG apertures 153, which have been described in greater detail above with reference to FIGS. 14 and 15.

Referring now to FIGS. 16 and 17 together, it will be seen that in currently preferred embodiments, MLG interior pieces $152_A$ and $152_B$ are two mirror-image halves disposed to be joined horizontally to form MLG interior 152. This currently preferred embodiment simplifies the manufacture of MLG interior 152, enabling the fabrication of long, straight sections of MLG interior pieces $152_A$ and $152_B$ that include substantially precise semi-circular cutouts for MLG apertures 153 over the entire length. The need for precise drilling of MLG apertures 153 over the entire length of MLG interior 152 is thus obviated.

In currently preferred embodiments, MLG interior 152 is made of Ultra-High Molecular Weight ((UHMW) plastic throughout MLG 150 (including MLG straight sections $150_S$, MLG curved sections $150_C$ and MLG stabbing guide $150_{SG}$). This UHMW plastic material is hard and robust, yet suitable for machining and related operations to create. MLG apertures 153 in fully assembled MLG interiors 152. The UHMW plastic material is further low-friction and self-lubricating, and also relatively hard-wearing, enabling KJL assemblies received in MLG apertures 153 to slide operably therethrough during extension and retraction operations.

With further reference to FIGS. 16 and 17, it will be understood that MLG straight sections $150_S$ are assembled by receiving MLG interior pieces $152_A$ and $152_B$ into MLG tube 151. MLG interior pieces $152_A$ and $152_B$ may be secured in MLG tube 151 by conventional methods, such as (for example) bolts, screws or other fasteners. All of such securing structure has been omitted for clarity on FIGS. 16 and 17. However, it will be appreciated that by using fasteners for such securing structure, MLG interior pieces $152_A$ and $152_B$ are interchangeable within MLG tubes 151. MLG interior pieces $152_A$ and $152_B$ may thus be changed out in individual MLG straight sections $150_S$ if they become damaged or worn. Similarly, if the user desires to change the configuration of KJL sizes (diameters) deployed within MLG 150, then MLG interior pieces $152_A$ and $152_B$ may be changed out throughout to provide corresponding receiving MLG apertures 153.

FIGS. 18 and 19 illustrate MLG curved section $150_C$ (from FIG. 15) in more detail. FIG. 19 depicts MLG curved section $150_C$ viewed from the direction of arrow 170 as shown on FIG. 18. The component parts of MLG curved section $150_C$ depicted on FIG. 18 are also depicted on FIG. 19 from this alternative view. It will be seen immediately from FIGS. 18 and 19 that conceptually, with its generally trapezoidal profile, MLG curved section $150_C$ is analogous in form and function to KJL segment 111 as illustrated on FIG. 10. For this reason, it may be helpful to read the following disclosure making reference to FIGS. 18 and 19 in association with earlier disclosure making reference to FIG. 10.

As with KJL segments 111 on FIG. 10, the intent of the generally trapezoidal profile of MLG curved section $150_C$ on FIGS. 18 and 19 is to enable a concatenated string of MLG curved sections $150_C$ to follow a curved path, as illustrated on FIG. 15. Accordingly, with reference to FIG. 18, MLG curved section $150_C$ comprises MLG tube 151 with opposing MLG tube sides $151_I$ and $151_O$. MLG tube side $151_I$ is shorter in longitudinal length than tube side $151_O$ in order to give MLG curved section $150_C$ its generally trapezoidal profile. It will be appreciated that when multiple MLG curved sections $150_C$ are concatenated such that MLG tube sides $151_I$ mate together and tube sides $151_O$ mate together, a generally curved string thereof will result, as illustrated on FIG. 15.

Concatenation of MLG curved sections $150_C$ may be enabled by any suitable conventional structure. In currently preferred embodiments, as illustrated on FIGS. 18 and 19, each MLG curved section $150_C$ provides MLG concatenation bolts 155, MLG concatenation holes 156 and MLG concatenation, lugs 157. Concatenation is enabled in such embodiments by fastening the MLG concatenation bolts 155 through the MLG concatenation lugs 157 of a first MLG curved section 150$_C$ and into the MLG concatenation holes 156 of a second, neighboring MLG curved section 150$_C$. Nothing in this disclosure should be construed, however, as limiting the concatenation of MLG curved sections 150$_C$ to the use of concatenation bolts, lugs and holes as illustrated on FIGS. 18 and 19.

The actual overall size and trapezoidal profile dimensions of MLG curved sections 150$_C$ (and, indeed, the corresponding dimensions of MLG straight sections 150$_S$ and MLG stabbing guide 150$_{SG}$) are all per user selection and design, according to the needs of a particular Scorpion System MLI (and associated MLG) deployment. Nothing herein should be construed to limit the Scorpion System to (or favor) a particular dimensional MLG design.

FIGS. 18 and 19 also illustrate currently preferred embodiments, of MLG interior 152 for MLG curved section 150$_C$. As with MLG straight section 150$_S$ (described above with reference to FIGS. 16 and 17), MLG tube 151 for MLG curved section 150$_C$ on FIG. 18 encases MLG interior 152. MLG interior 152 on FIG. 18 thus, shares the general trapezoidal profile of MLG curved section 150$_C$ and associated MLG tube 151. In distinction to MLG straight section 150$_S$ (described above with reference to FIGS. 16 and 17), however, FIGS. 18 and 19 show that currently preferred embodiments call for the manufacture of MLG interior 152 for MLG curved section 150$_C$ from one solid piece of UHMW plastic, and further call for MLG apertures 153 provided in MLG interior 152 to be oblate or slotted rather than substantially circular.

By momentary reference to FIG. 15, it will be, appreciated that the shorter overall longitudinal length of a typical MLG curved section 150$_C$ enables MLG interior 152 to be manufactured from one UHMW plastic piece, since MLG apertures 153 may be more precisely drilled, reamed and otherwise machined through such a shorter length of UHMW plastic. It will be further appreciated by reference to FIGS. 18 and 19 that MLG apertures 153 are oblate or slotted in MLG curved section 150$_C$ in order to accommodate the articulated series of straight edges that occurs when KJL assemblies deployed within MLG apertures 153 are in "curved tube" mode, per earlier disclosure making reference to FIGS. 8 and 11.

It will be further recalled from FIG. 14 and associated disclosure that in some embodiments, smaller diameter KJL assemblies are preferably manufactured with longer longitudinal length in order to optimize manufacturing costs. It will thus be appreciated that when such smaller-diameter, longer-longitudinal-length KJL assemblies are in curved mode (per FIGS. 8 and 11 and associated disclosure), the resulting, articulated series of straight edges is more pronouncedly "straight" (i.e. more a series of straight edges and less of a "curve"). This "more pronounced straight edge" effect in turn requires a correspondingly greater "slotting" of the MLG apertures 153 in MLG curved sections 150$_C$, in order to slidably accommodate the straight edges of a KJL assembly in "curved tube" mode without undue bending.

It will be again understood that actual oblate or slotted dimensions of MLG apertures 153 in MLG curved sections 150$_C$ are all per user selection and design, according to the needs of a particular deployment of KJL assemblies therein, in combination with the overall dimensional design of the MLG. Nothing herein should be construed to limit the MLG in this regard.

It will be further understood that MLG interior 152 may be secured in MLG tube 151 on MLG curved sections 150C by conventional methods, such as (for example) bolts, screws or other fasteners. All of such seeming structure has been omitted for clarity on FIGS. 18 and 19. However, it will be appreciated that by using fasteners for such securing structure, MLG interiors 152 are interchangeable within MLG tubes 151. MLG interiors 152 may thus be changed out in individual MLG curved sections 150$_C$ if they become damaged or worn. Similarly, if the user desires to change the configuration of KJL sizes (diameters) deployed within MLG 150, then MLG interiors 152 may be changed out throughout to provide corresponding receiving MLG apertures 153.

Figure 21:
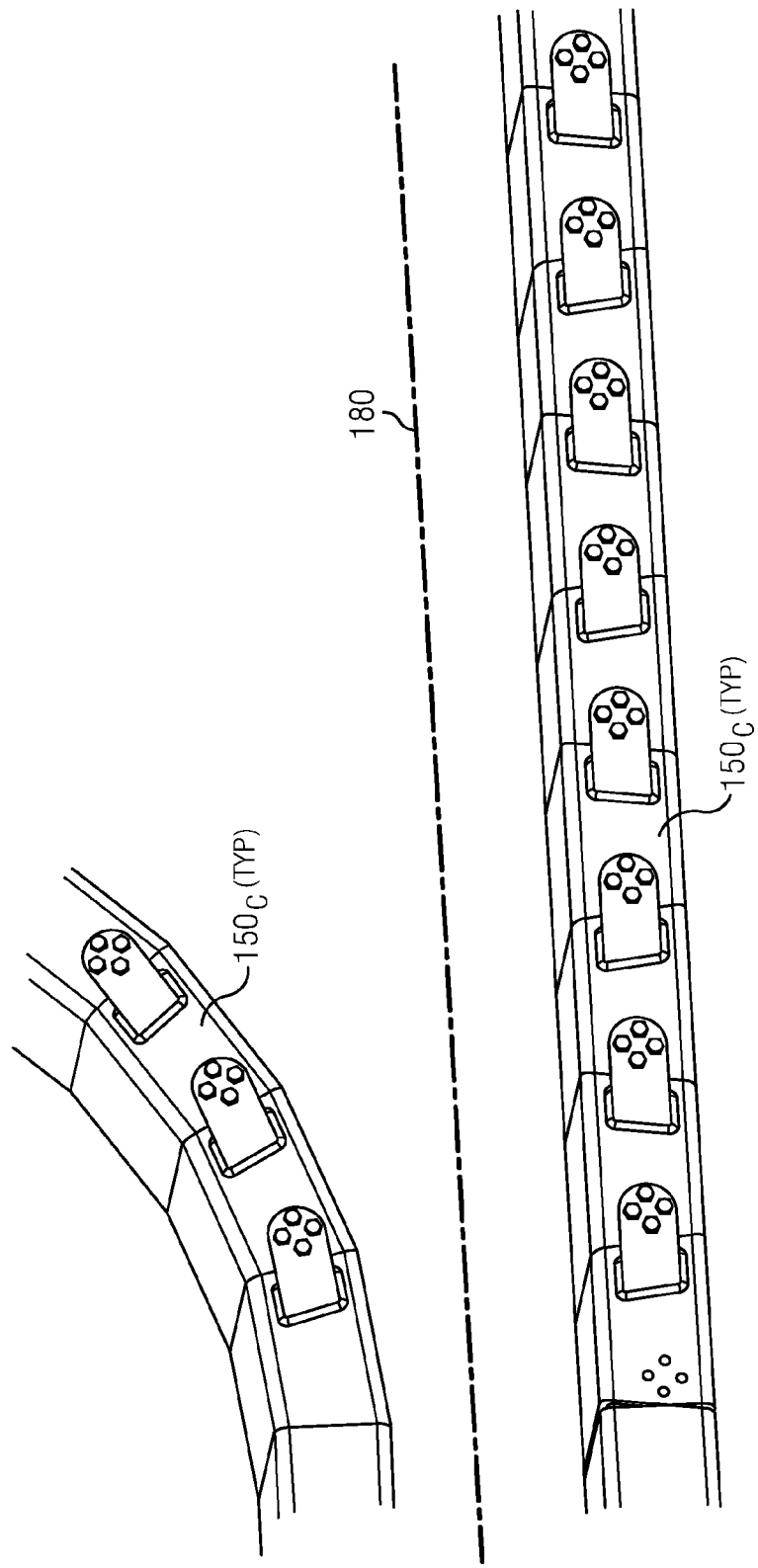

FIGS. 20 and 21 are side-by-side comparisons of MLG 150 in curved and straight modes. Earlier material in this disclosure (for example, with reference to FIGS. 7 through 11) describes embodiments of the Scorpion System MLI in curved or straight modes, according to user selection Such material further describes embodiments in which KJL assemblies may be "converted" back and forth between curved and straight modes. FIGS. 20 and 21 illustrate curved and straight embodiments of MLG 150, which may also be converted back and forth between modes in order to support, the corresponding mode that the user selects for KJL assemblies deployed therein.

FIG. 21 is an enlargement of a portion of FIG. 20 as shown on FIG. 20. Chained line 180 appears in both FIGS. 20 and 21, and serves to divide the illustrations functionally between curved mode (above chained line 180) and straight mode (below chained line 180).

Referring first to FIG. 20, MLG 150 is illustrated in "curved tube" mode (above chained line 180) substantially as illustrated in FIG. 15. In this "curved tube" mode, MLG 150 comprises MLG straight sections 150$_S$, MLG curved sections 150$_C$ and MLG stabbing guide MLG$_{SG}$, as previously illustrated. Further, MLG curved sections 150$_C$ have been concatenated as described above with reference to FIGS. 18 and 19, wherein the general trapezoidal profiles of MLG curved sections 150$_C$ are aggregated into an overall generally curved concatenation thereof.

FIG. 20 also illustrates MLG 150 in straight mode (below chained line 180). Again, MLG 150 comprises MLG straight sections 150$_S$, MLG curved sections 150$_C$ and MLG stabbing guide MLG$_{SG}$ in this straight mode. However, in this straight mode, MLG curved sections 150$_C$ have been concatenated such that their general trapezoidal profiles have been arranged to "cancel each other out" rather aggregate into an overall general curve.

This "canceling out" aspect of a straight mode embodiment of MLG 150 is best viewed on FIG. 21. Above chained line 180, FIG. 21 illustrates the general trapezoidal profiles of MLG curved sections 150$_C$ arranged to aggregate into an overall general curve. Below chained line 180, FIG. 21 illustrates the general trapezoidal profiles of MLG curved sections 150$_C$ arranged to oppose, or to "cancel each other out", so that the concatenation of MLG curved sections 150$_C$ is in a straight line.

It thus will be appreciated that a concatenation of MLG curved sections 150$_C$ may be "converted" back and forth between curved and straight modes by unfastening the concatenated sections, reversing the general trapezoidal aspect of every other section (i.e. "flipping it over"), and re-fastening. In such "convertible" embodiments, fastening structure should preferably be provided symmetrically to enable similar fastening whether in curved or straight modes. Also, with additional reference to FIGS. 18 and 19, before MLG curved sections 150$_C$ are re-fastened, MLG interiors 152 of MLG curved sections 150$_C$ that are reversed (or "flipped over") may also need to be reversed (or "flipped over") themselves in order to preserve continuity of MLG apertures 153 from one MLG curved section $150_C$ to the next. It will be seen from FIGS. 18 and 19 that reversal of MLG interiors 152 may be accomplished by unfastening and removing them from their MLG tubes 151, reversing their orientation, and then re-fastening them into MLG tubes 151.

Although not illustrated in any detail, it will be understood from FIG. 15 that MLG stabbing guide $150_{SG}$ is, in currently preferred embodiments, substantially a MLG straight section $150_S$ as illustrated and described in detail with reference to FIGS. 16 and 17. MLG stabbing guide $150_{SG}$ differs primarily from MLG straight section $150_S$ in that MLG stabbing guide $150_{SG}$ also provides gaps G (as described with reference to FIG. 15).

Figure 24:
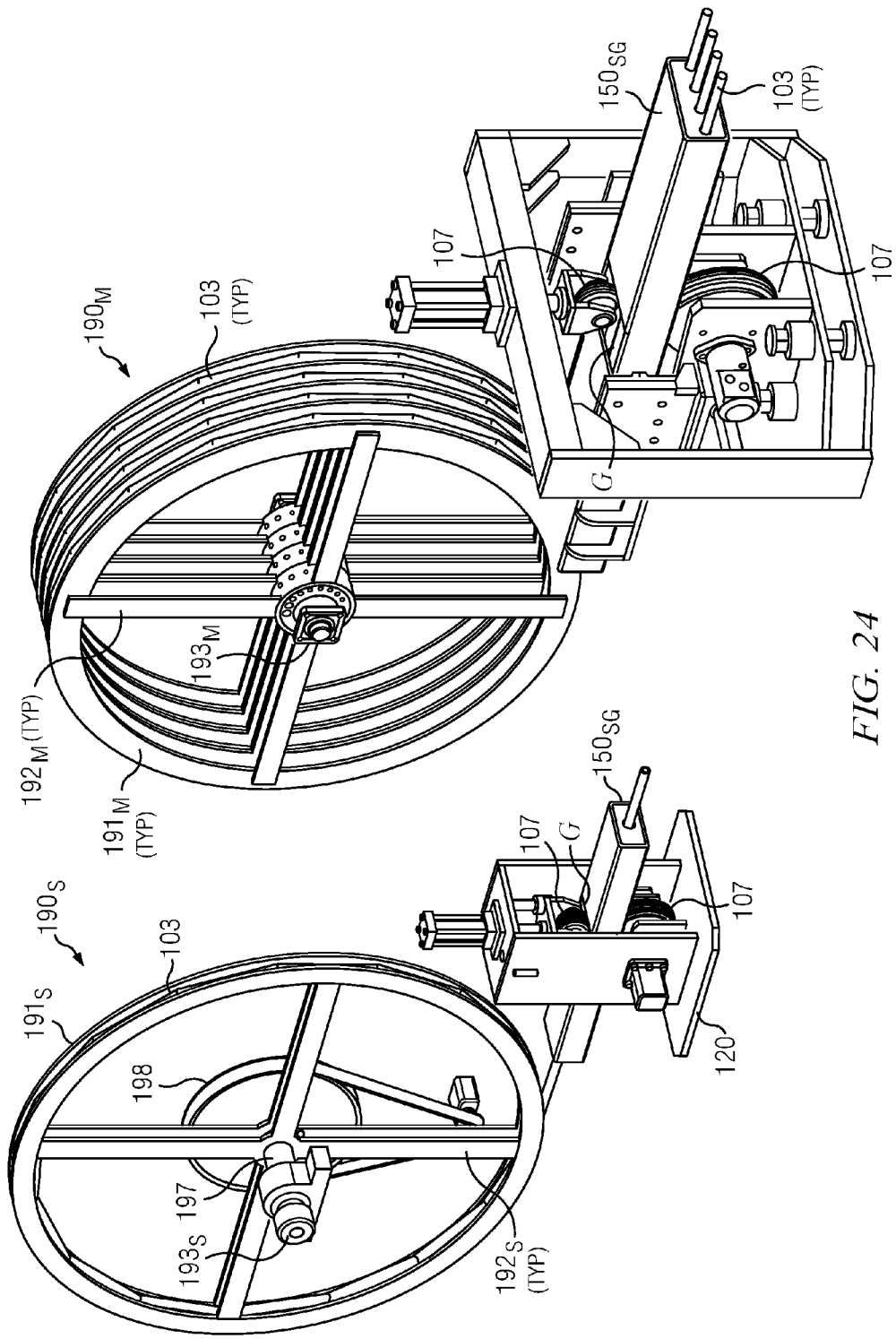
Figure 25:
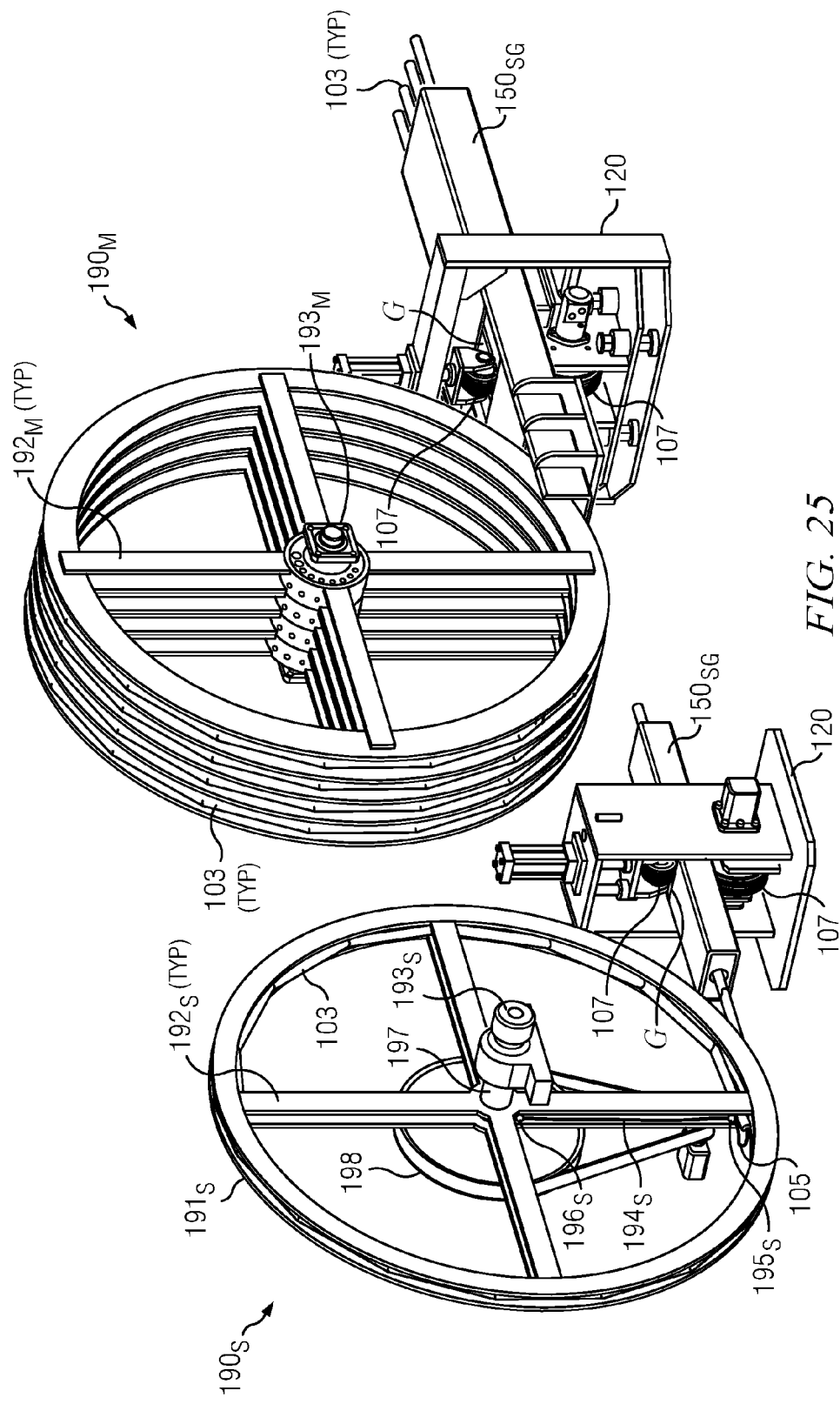
Figure 26:
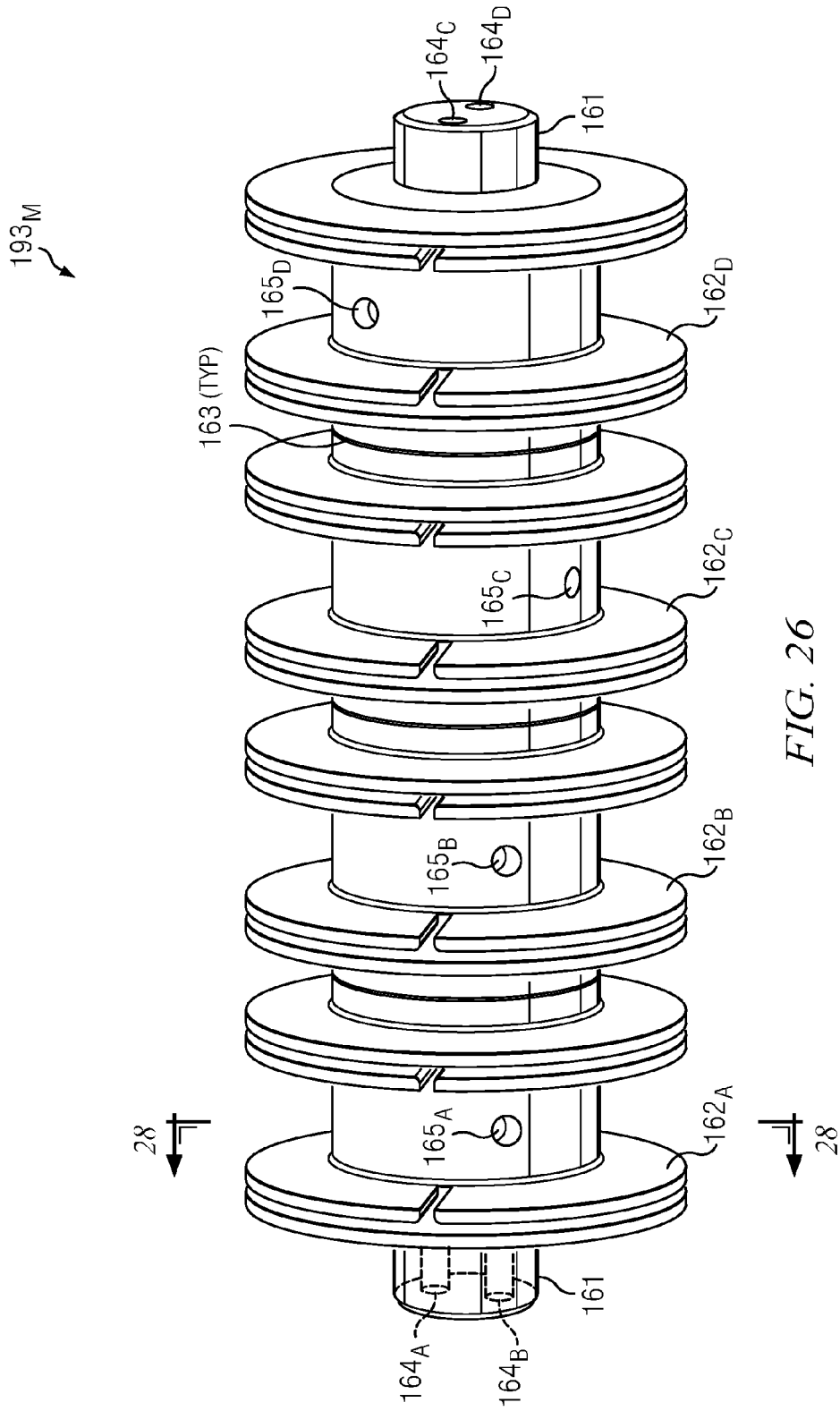

FIGS. 22 through 25 illustrate various views of Single Lance Reel (SLR) assembly $190_S$ and Multi-Lance Reel (MLR) assembly $190_M$. FIG. 26 illustrates aspects and features of MLR axle assembly $193_M$ on MLR assembly $190_M$ in more detail. As throughout this disclosure, items depicted on FIGS. 22 through 26 that are also depicted on other FIGURES in this disclosure have the same numeral.

Embodiments of the Scorpion System deploying either SLR assembly $190_S$ or MLR assembly $190_M$ on FIGS. 22 through 25 enable concatenated strings of KJL assemblies 103 to be rolled and unrolled, as required, onto or off a rotary "reel"-like assembly as such KJL assemblies 103 are selectably retracted or extended in and out of tubular W. It will be appreciated the primary difference between SLR assembly $190_S$ and MLR assembly $190_M$ is that SLR assembly $190_S$ provides "reel"-like structure for rolling up and unrolling a single KJL assembly 103, while MLR assembly $190_M$ provides "reel"-like structure for rolling up and unrolling multiple KJL assemblies 103 (each KJL assembly 103 capable of being rolled up or unrolled independently per user selection). FIGS. 22 through 26 illustrate embodiments of MLR assembly $190_M$ in which an example of four (4) KJL assemblies 103 are available to be independently rolled up or unrolled. Nothing in this disclosure should be interpreted, however, to limit MLR assembly $190_M$ to handling any particular number (two or more) of KJL assemblies 103.

SLR assembly $190_S$ and MLR assembly $190_M$ are thus alternative embodiments to the earlier described functionality provided by MLG 150 (as illustrated on FIGS. 14 through 21), or guide tubes 101 (as illustrated on FIGS. 1 through 13). Instead of holding and positioning concatenated strings of KJL assemblies 103 in an encased structure (as in MLG 150 or guide tubes 101), SLR assembly $190_S$ and MLR assembly $190_M$ hold and position concatenated strings of KJL assemblies 103 by rolling them up onto a "reel"-like structure. As will be appreciated from FIGS. 22 through 25, therefore, embodiments deploying either SLR assembly $190_S$ or MLR assembly $190_M$ obviate any need for curved or straight modes (such as were described, above with reference to MLG 150 or guide tubes 101), although KJL assembly itself may be in curved mode or straight mode, depending on whether it is spooled onto SLR assembly $190_S$ or MLR assembly $190_M$ (curved mode), or operationally extending or retracting (straight mode). In this way, embodiments deploying either SLR assembly $190_S$ or MLR assembly $190_M$ potentially permit substantial savings in footprint. Such SLR and MLR embodiments further simplify overall deployment of the Scorpion System by obviating the structural steel and other conventional infrastructure that, as described above (although not illustrated for clarity), is required to support and serve either MLG 150 or guide tubes 101.

Figure 22:
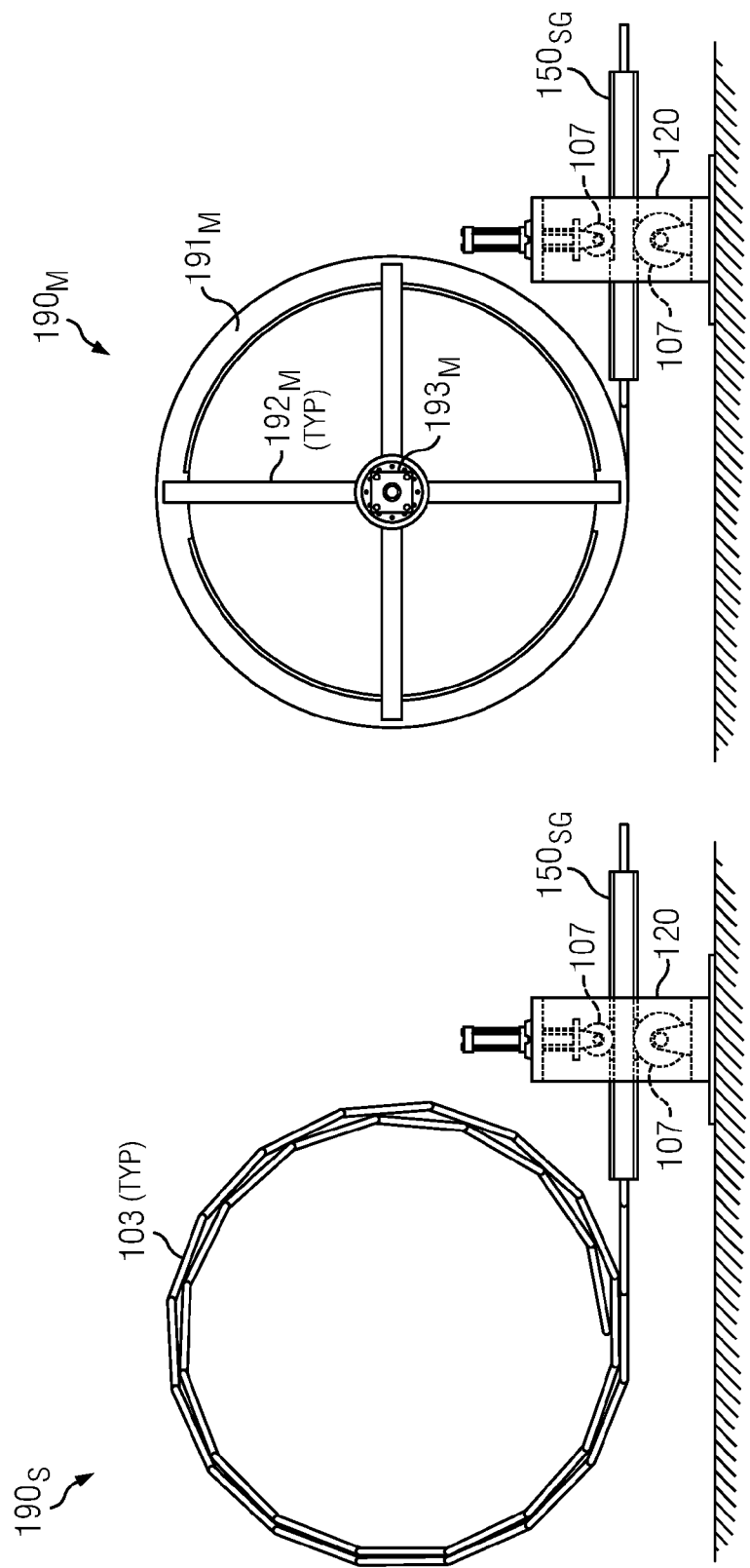
FIG. 22 is an elevation view of embodiments of SLR assembly $190_S$ and MLR assembly $190_M$.

Before describing SLR assembly $190_S$ and MLR assembly $190_M$ on FIGS. 22 through 28 in detail, it should be noted that FIG. 22, for example, depicts KJL assembly 103 rolled up onto MLR assembly $190_M$ in an "un-nested" state. Refer also to disclosure below association with FIGS. 29 through 43, and particularly FIGS. 40 through 42, in which currently preferred embodiments of KJL 200 (an alternative embodiment to KJL assembly 103) are configured to be deployed on a reel in a nested state. Although the un-nested state as depicted in FIG. 22 is serviceable, embodiments of KJL 200 configured, to deploy on a reel in a nested state (such as depicted on FIGS. 40 and 41) bring additional advantages by enabling compact storage on the reel while also allowing KJL segments 203 to reside on the reel in a comparatively unstressed state.

Turning now to FIG. 22, SLR assembly $190_S$ is illustrated with a concatenated string of KJL assemblies 103 substantially fully "rolled up" ready for extension thereof during internal cleaning, inspection or other operations. Substantially all of the structure of SLR assembly $190_S$ has been removed for clarity on FIG. 22 in order to enable better appreciation of the functional operation of SLR assembly $190_S$ (and, by association, MLR assembly $190_M$). The embodiment of SLR assembly $190_S$ illustrated on FIG. 22 further shows depicts an embodiment of MLG stabbing guide $150_{SG}$ (refer FIG. 15) and an embodiment of adjustment assembly 120 (including stabbing wheels 107, hidden from view, refer FIGS. 12 and 13) positioned and disposed, per earlier, disclosure, to extend and retract the concatenated string of KJL assemblies 103. It will be understood from the embodiment of SLR assembly $190_S$ illustrated on FIG. 22 that as stabbing wheels 107 on adjustment assembly 120 rotate and extend/retract KJL assemblies 103, the "reel"-like structure provided by SLR assembly $190_S$ (omitted for clarity on FIG. 22 but depicted, for example, on FIG. 23) unrolls and rolls up in corresponding fashion to "pay out" and "take up" the concatenated string of KJL assemblies 103.

FIG. 22 further illustrates MLR assembly $190_M$, which, as noted, operates in conceptually and functionally the same manner as SLR assembly 190S to "pay out" and "take up" any one of multiple concatenated strings of KJL assemblies 103 deployed thereon as such KJL assemblies 103 are extended/retracted independently per user selection. The embodiment of MLR assembly $190_M$ depicted on FIG. 22 is biding the KJL assemblies 103 deployed thereon, but these KJL assemblies 103 may be seen by momentary reference to, for example, the view on FIG. 24. The embodiment of MLR assembly $190_M$ depicted on FIG. 22 illustrates MLR rim $191_M$, MLR spokes $192_M$ and MLR axle assembly $193_M$ in elevation view and in general form.

Figure 23:
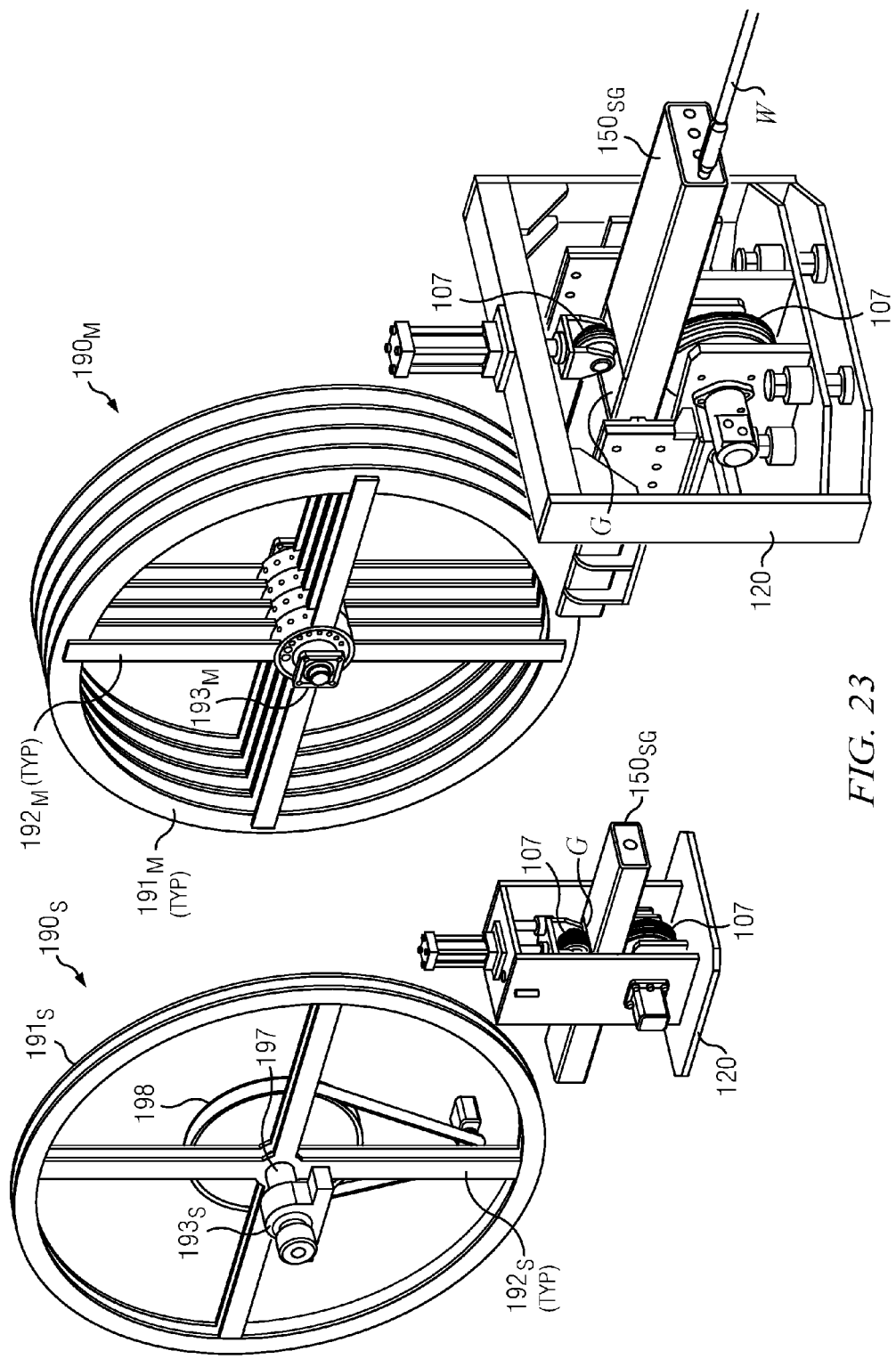
FIGS. 23, 24 and 25 are isometric views of embodiments of SLR assembly $190_S$ and MLR assembly $190_M$.

Reference is now made to FIG. 23, depicting SLR assembly $190_S$ and MLR assembly $190_M$ in a perspective view. KJL assemblies 103 (shown on 24 and 22, for example) have been omitted from SLR assembly $190_S$ and MLR assembly $190_M$ on FIG. 23 for clarity. Among, other features, FIG. 23 contrasts the multiple independent reel structure of MLR assembly $190_M$ with the single reel structure of SLR assembly $190_S$. FIG. 23 also illustrates each of MLR assembly $190_M$ and SLR assembly $190_S$ having rims $191_M$ and $191_S$, spokes $192_M$ and $192_S$, and axle assemblies $193_M$ and $193_S$ (which features will be described in more detail further on in this disclosure).

In both MLR assembly $190_M$ and SLR assembly $190_S$ embodiments illustrated on FIG. 23, wheels 107 engage on KJL assemblies 103 via gap G in embodiments of MLG stabbing guide $150_{SG}$ (KJL assemblies 103 omitted on FIG. 23 for clarity, as noted above). Consistent with earlier disclosure associated with, for example, FIG. 1, rotation of wheels 107 causes KJL assemblies 103 to extend and retract into and out of tubular W. It will be understood from FIG. 22 and now FIG. 23 that as KJL assemblies 103 extend and retract into and out of tubular W, MLR and SLR assemblies $190_M$ and $190_S$ "pay out" and "take up" the concatenated string of KJL assemblies 103 using "reel"-like structure on which KJL assemblies 103 are unrolled and rolled up.

It will be further appreciated with reference to FIG. 23 that on MLR assembly $190_M$, any selected one of the multiple strings of KJL assemblies 103 deployed thereon may be "paid out" and "taken up" independently of the other strings of KJL assemblies 103 also deployed thereon (such non-selected strings of KJL assemblies 103 remaining motionless while the selected one is "paid out" and/or "taken up"). MLR axle assembly $193_M$, in conjunction with MLR rims $191_M$ and MLR spokes $192_M$, provides structure to enable independent "paying out" or "taking up" of any string of KJL assemblies 103 deployed, and will be described in greater detail further on with reference to FIG. 26, This structure on MLR assembly $190_M$ enabling independent "paying out" or "taking up" of any string of KJL assemblies 103 deployed thereon enables MLR assembly $190_M$ to be compatible with earlier disclosure (see FIGS. 1, 2, 12 and 13 and associated disclosure including stabbing wheels 107 and adjustment assembly 120, for example) in which any one of multiple strings of KJL assemblies 103 may be user-selected at any particular time for extension into and retraction out of tubular W. It will be further understood that particularly with regard to MLR assembly $190_M$, as adjustment assembly 120 moves concatenated strings of KJL assemblies 103 from side to side to bring a selected string thereof between stabbing wheels 107, MLR assembly $190_M$ may be disposed to make corresponding lateral movements.

FIG. 24 illustrates MLR and SLR assemblies $190_M$ and $190_S$ in similar fashion to FIG. 23, except FIG. 24 also shows concatenated strings of KJL assemblies 103 deployed on MLR and SLR assemblies $190_M$ and $190_S$ (such strings of KJL assemblies 103 omitted for clarity on FIG. 23). Disclosure above referring to FIGS. 22 and 23 applies equally with reference to FIG. 24, FIG. 25 illustrates MLR and SLR assemblies $190_M$ and $190_S$ in similar fashion to FIG. 24, except shown from a different perspective angle. FIG. 25 further shows SLR assembly $190_S$ with parts of SLR rim $191_S$ removed so that KJL assemblies 103 can be seen more clearly deployed thereon.

The following disclosure regarding deployment of KJL assemblies 103 on SLR rim $191_S$ is also illustrative of corresponding deployment of each of the multiple KJL assemblies 103 acting independently on MLR rims $191_M$, although such structure on MLR rims $191_M$ is hidden from view on FIG. 25. It will be seen on FIG. 25 that the first KJL assembly 103 in the concatenated string thereof is anchored to SLR rim $191_S$ with the distal end of the first KJL assembly 103 near any one of SLR spokes $192_S$. Anchoring may be by any conventional removable anchoring structure, such as threaded bolts, for example, wherein KJL assemblies 103 may be periodically removed from SLR rim $191_S$ for maintenance. In some embodiments, SLR rim $191_S$ provides sidewalls whose spacing is selected to be wide enough to enable a string of KJL assemblies 103 to roll up and unroll comfortably between the sidewalls to permit a helical spooling. In this way, unwanted bending, twisting or shear stresses on the couplings between individual KJL assemblies 103 are minimized as strings thereof are rolled up and unrolled. Other embodiments may provide SLR rim $191_S$ to be narrow enough for successive rolls of KJL assemblies 103 to stack vertically on top of each other rather than "sliding down" partially or completely side by side. Refer also to FIGS. 29 through 43 and associated disclosure, and particularly to FIGS. 40 and 41, for discussion of embodiments of KJL 200 (an alternative embodiment of KJL assembly 103) configured to nest when spooled onto a reel.

Some embodiments of SLR assembly $190_S$ and MLR assembly $190_M$ as illustrated on FIG. 25 are advantageously sized so that approximately two (2) revolutions thereof will extend a string of KJL assemblies 103 from "fully rolled up" to "fully paid out" (and vice versa). Nothing in this disclosure should be interpreted, however, to limit the choice of size of SLR assembly $190_S$ and/or MLR assembly $190_M$ in this regard.

As noted above, it will be understood that, although not fully depicted on FIG. 25 (because MLR rims $191_M$ on MLR assembly $190_M$ are not partially removed on FIG. 25), the preceding disclosure regarding KJL assemblies 103 deployed on SLR assembly $190_S$ as shown on FIG. 25 is illustrative of each of the KJL assemblies 103 deployed on MLR assembly $190_M$.

It will be further recalled from earlier disclosure that in some embodiments, KJL assemblies 103 encase at least one hose 105 that serves tooling head 106 on a distal end of each string of KJL assemblies 103. Refer back, for example, to FIGS. 1 and 14 with associated disclosure herein. Referring now to FIG. 25 again, it will be appreciated that in the illustrated embodiment, hose(s) 105 within it assemblies on SLR assembly $190_S$ terminate at SLR rim $191_S$. SLR spoke hose(s) $194_S$ connect to hose(s) 105 at SLR rim hose connection $195_S$ and extend along a selected SLR spoke $192_S$ to SLR axle hose correction $196_S$ near or on SLR axle assembly $193_S$.

It will be further appreciated that some embodiments of SLR assembly $190_S$ provide connection structure as described above and illustrated on FIG. 25 (including SLR rim hose connection $195_S$, SLR spoke hose(s) $194_S$ and SLR axle hose connection $196_S$) in order to facilitate, maintenance and replacement of hose(s) 105 in KJL assemblies 103. Nothing in this disclosure should be interpreted to limit the type, location or manner of connection of hose(s) 105 across SLR assembly $190_S$ in other embodiments thereof.

With continuing reference to FIG. 25, SLR axle assembly $193_S$ comprises a conventional rotary union 197. A remote source or reservoir of fluids or other material to be carried and ultimately delivered by hose(s) 105 within KJL assemblies 103 may thus be connected to rotary union 197 on SLR axle assembly $193_S$ (such remote source/reservoir and connection omitted on FIG. 25 for clarity). The fluids or other material flow through rotary union 197 and into hose(s) 105 within KJL assemblies 103 via SLR axle hose connection $196_S$, SLR spoke hose(s) $194_S$ and SLR rim hose connection $195_S$.

FIG. 25 further illustrates SLR drive 198 on SLR assembly $190_S$. SLR drive 198 may be any conventional drive mechanism, and this disclosure is not limited in this regard. In some embodiments of SLR assembly $190_S$, SLR drive 198 is a direct drive.

SLR drive 198 is provided on SLR assembly $190_S$ to cooperate with stabbing wheels 107 in extending and retracting strings of KJL assemblies 103. In some embodiments, stabbing wheels 107 are the primary extending and retraction mechanism (see, for example, FIG. 1 and associated disclosure above). In embodiments deploying SLR assembly $190_S$, however, SLR drive 198 assists stabbing wheels 107 to keep mild tension in strings of KJL assemblies 103 as they are "rolled up" and "paid out". SLR drive 198 may also provide additional power to assist stabbing wheels 107 with extension and retraction of KJL assemblies 103 when required.

It will be recalled from earlier disclosure that FIG. 25 shows SLR assembly 190$_S$ with parts of SLR rim 191$_S$ removed so that KJL assemblies 103, hose(s) 105 and associated structure can be seen more clearly deployed thereon. The preceding disclosure regarding deployment of KJL assemblies 103 on SLR rim 191$_S$ and the structure connecting hose(s) 105 to SLR axle assembly 193$_S$ is also illustrative of corresponding deployment of each of the multiple KJL assemblies 103 and associated hoses 105 acting independently on MLR rims 191$_M$, although such structure on MLR rims 191$_M$ is hidden from view on FIG. 25. In some embodiments of MLR assembly 190$_M$, although not specifically illustrated, each string of KJL assemblies 103 terminates near a selected MLR spoke 192$_M$. Although again hidden from view, it will be understood that hose(s) 105 deployed within each string of KJL assemblies 103 are advantageously connected to MLR axle assembly 193$_M$ via MLR rim hose connections, MLR spoke hoses and MLR axle hose connection, It will be further appreciated that, consistent with similar disclosure with respect to SLR assembly 190$_S$ above, some embodiments of MLR assembly 190$_M$ provide connection structure as described immediately above including MLR rim hose connections, MLR spoke hoses and MLR axle hose connection identified above but hidden from view on FIG. 25) in order to facilitate maintenance and replacement of hose(s) 105 in KJL assemblies 103. Nothing in this disclosure should be interpreted to limit the type, location or manner of connection of hose(s) 105 across MLR assembly 190$_M$ in other embodiments thereof.

FIG. 26 illustrates features and components of an embodiment of MLR axle assembly 193$_M$ in more detail. By way of background, it will be appreciated from earlier disclosure that on MLR assembly 190$_M$, each string of KJL assemblies 103 deployed thereon is free to be "paid out" or "taken up" independently according to user selection. It will be further recalled that in preferred embodiments (as illustrated on FIG. 25, for example) four (4) independent stings of KJL assemblies 103 are deployed on a single MLR assembly 190$_M$. A conventional rotary union, such as rotary union 197 disclosed above on SLR axle assembly 193$_S$, is thus not operable for analogous deployment on MLR axle assembly 193$_M$, since up to four (4) independent supplies of fluids or other materials need to be carried independently and separately from their respective remote sources or reservoirs via MLR axle assembly 193$_M$ to a corresponding hose 105 within one of the independently extensible/retractable strings of KJL assemblies 103 deployed on MLR assembly 190$_M$. A conventional rotary union will typically provide structure for only a single supply of fluid through the union.

FIG. 26 illustrates aspects of MLR axle assembly 193$_M$ in which, consistent with preferred embodiments illustrated elsewhere in this disclosure, four (4) separate and independent supplies of fluids or other materials may be carried through MLR axle assembly 193$_M$. As noted earlier, this disclosure's example to illustrate and describe MLR assembly 190$_M$ (and associated MLR axle assembly 193$_M$) as providing four (4) separate and independent supplies of fluids or other materials to each of four (4) independently-operable strings of KJL assemblies 103 is an exemplary embodiment only. Nothing in this disclosure should, be interpreted to limit MLR assembly 190$_M$ (and MLR axle assembly 193$_M$) to provide for more or fewer than four (4) separate and independently-operable strings of KJL assemblies 103.

With continuing reference to FIG. 26. MLR axle assembly 193$_M$ comprises stationary axle 161, on which four (4) axle spools 162$_A$, 162$_B$, 162$_C$ and 162$_D$ are separated by spool seals 163. Spool seals 163 may be any suitable seal between independently rotating parts, such as conventional swivel seals, and this disclosure is not limited in this regard. Axle spools 162$_A$, 162$_B$, 162$_C$ and 162$_D$ are each free to rotate separately and independently on axle 161. Viewing FIGS. 22 and 26 together, it will be appreciated that MLR spokes 192$_M$ on FIG. 22 advantageously attach to MLR axle assembly 193$_M$ via bolting or other similar conventional means to axle spools 162$_A$, 162$_B$, 162$_C$ and 162$_D$, as illustrated on FIG. 26.

Figure 27:
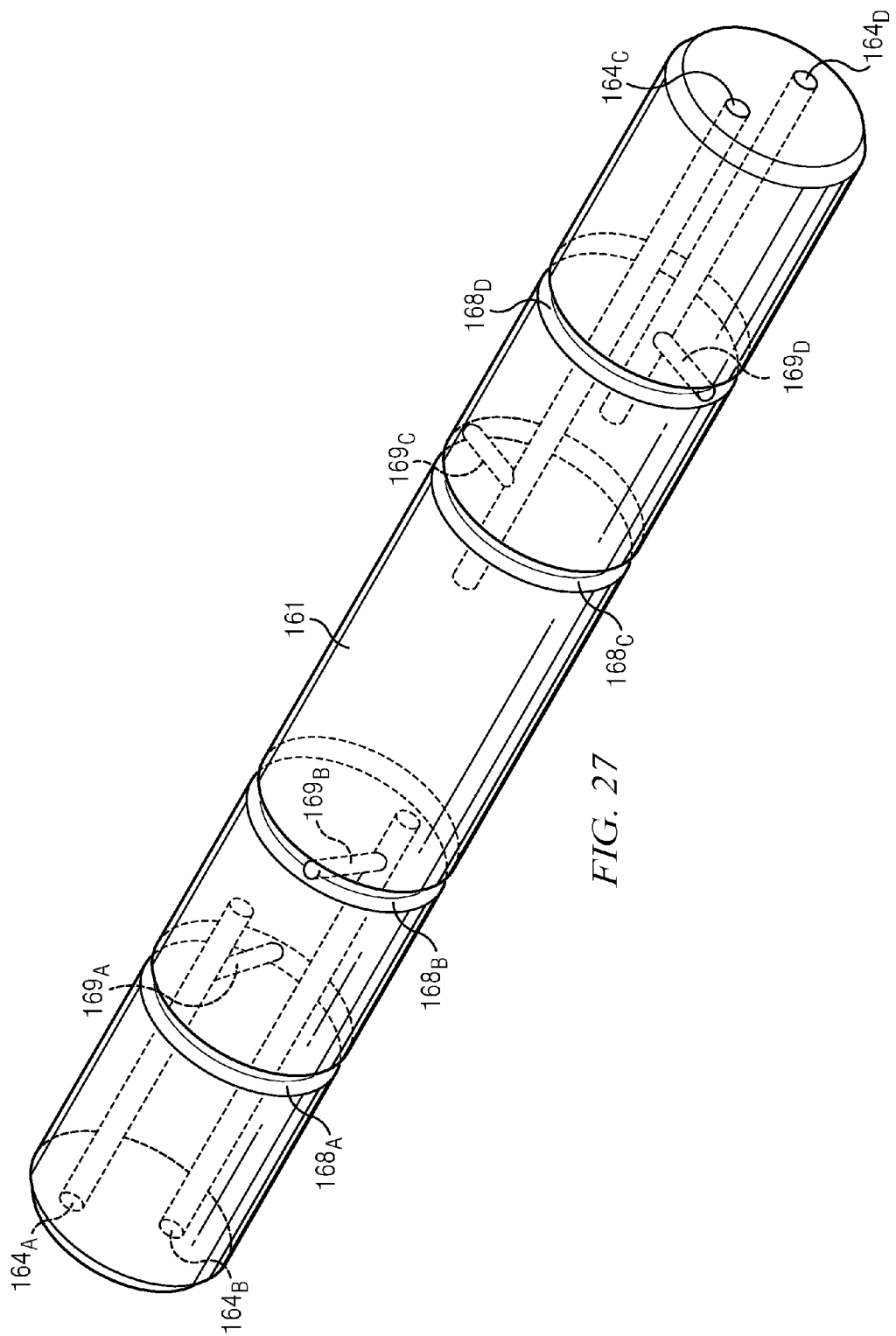

FIG. 27 illustrates axle 161 on FIG. 26 in isolation. FIG. 28 is a section view as shown on FIG. 26. The section view of FIG. 28 is a cross-section through outlet port 165$_A$, and is typical of the views that would also be seen in corresponding cross-sections through outlet ports 165$_B$ through 165$_D$. Referring first to FIG. 26 again, axle 161 further comprises inlet ports 164$_A$ and 164$_B$ at one end, and inlet ports 164$_C$ and 164$_D$ at the other end. Axle spools 162$_A$, 162$_B$, 162$_C$ and 162$_D$ each provide a corresponding outlet port 165$_A$, 165$_B$, 165$_C$ and 165$_D$. Inlet ports 164$_A$ through 164$_D$ each connect to a corresponding one of outlet ports 165$_A$ through 165$_D$ via individual and separate pathways through the interior of axle 161 and axle spools 162$_A$ through 162$_D$, respectively (embodiments of such pathways illustrated on FIGS. 27 and 28). Such pathways may be of any convenient conventional design, such as, with reference to FIG. 27, drilling out each pathway in the core of axle 161 beginning at an inlet port 164$_A$ through 164$_D$, and emerging in a radial direction via axle port passageways 169$_A$ through 169$_D$ into axle grooves 168$_A$ through 168$_D$ at the circumference of axle 161 in line with the circumference of rotation above of the corresponding outlet port 165A through 165$_D$ on axle spools 162$_A$ through 162$_D$. Referring now to FIG. 28, each axle spool 162$_A$ through 162$_D$ may then provide a semi-circular (or other shaped profile) axle spool groove 167$_A$ through 167$_D$ on its internal circumference in line with its corresponding outlet port 165$_A$ through 165$_D$, and to which axle spool groove 167$_A$ through 167$_D$ each corresponding outlet port 165$_A$ through 165$_D$ is connected via spool port passageways 166$_A$ through 166$_D$. In such embodiments, the grooves on each surface (axle grooves 168$_A$ through 168$_D$ on the outer surface of axle 161 and axle spool grooves 167$_A$ through 167$_D$ on the internal surface of axle spools 162$_A$ through 162$_D$) may combine to form a ring groove RG as part of the, flow passageway between inlet ports 164$_A$ through 164$_D$ and corresponding outlet ports 165$_A$ through 165$_D$. Rotary seals (not illustrated) may be provided between axle 161 and axle spools 162$_A$ through 162$_D$ either side of ring groove RG. In this way, as shown in exemplary form on FIG. 28, fluids or other material may enter, into a selected one of inlet ports 164$_A$ through 164$_D$ and exit out of a corresponding one of outlet ports 165$_A$ through 165$_D$, via its drilled pathway in axle 161 and the sealed rotating ring groove RG under the corresponding one of axle spools 162$_A$ through 162$_D$. Embodiments may advantageously hold and pass fluids or other materials in and through the immediately foregoing pathway structure at pressures up to 20 kpsi.

With reference now to FIGS. 22 and 25 and associated disclosure above, and with continuing reference to FIG. 26, it will be appreciated that outlet ports 165$_A$ through 165$_D$ may be connected to hose(s) 105 deployed within each string of KJL assemblies 103 deployed on MLR assembly 190$_M$ via MLR axle hose connections, MLR spoke hoses and MLR rim hose connections (such connection structure hidden from view on FIGS. 22 and 25, but analogous to SLR axle hose connection 196$_S$, SLR spoke hose 194$_S$ and SLR rim hose connection 195$_S$ illustrated and described above with respect to SLR assembly 190$_S$ on FIG. 25). It will the therefore understood from the foregoing disclosure that each hose 105 deployed within each independently extendable and retractable string of KJL assemblies 103 deployed on MLR assembly 190$_M$ may be addressed and supplied with fluid (or other materials) via a corresponding designated stationary inlet port 164$_A$ through 164$_D$ located on axle 161.

In exemplary embodiments, the drive structure on MLR assembly 190$_M$ provides separate and independently operable drives, such as conventional chain and sprocket drives or belt and pulley drives, to rotate each MLR rim 191$_M$ independently, in order to enable each corresponding string of KJL assemblies 103 to be extended or retracted independently, per user selection. It will be appreciated from the structure of MLR axle assembly 193$_M$ as illustrated on FIG. 26 that direct drive structure (such as suggested above for SLR drive 198 in some embodiments of SLR assembly 190$_S$ as illustrated on FIG. 25) is not optimal to provide independent drive structure to at least interior spools 162$_B$ and 162$_C$. Conventional belt or chain drives more suitable to drive at least interior spools 162$_B$ and 162$_C$. Some embodiments of MLR 190$_M$ may provide direct drive structure to drive end spools 162$_A$ and 162$_D$ on MLR axle assembly 193$_M$, while other embodiment may provide other conventional drives, such as belt or chain drives, on end spools 162$_A$ and 162$_D$.

FIGS. 29 through 43 will now be described. FIGS. 29 through 43 should be viewed together. Any part, item, or feature that is identified by part number on one of FIGS. 29 through 43 will have the same part number when illustrated on another of FIGS. 29 through 43. It will be understood that the embodiments as illustrated and described with respect to FIGS. 29 through 43 are exemplary, and the scope of this disclosure is not limited to such illustrated and described embodiments.

FIGS. 29 through 43 illustrate features and aspects of a Knuckle Jointed Lance ("KJL") 200. KJL 200 is an alternative embodiment of KJL assembly 103 depicted and described elsewhere in this disclosure, for example with reference to FIGS. 8 through 11 above. It will be understood that, similar to embodiments of KJL assembly 103 described elsewhere in this disclosure, the embodiments of KJL 200 encase one or more hoses or other types of flexible supply that tooling on a distal end of KJL 200 may require, such as, for example, steam hoses, water hoses, air hoses, nitrogen gas hoses, or conduits comprising electrical power supply cords, data transfer wiring, solid conductors, coils or antennae. The scope of this disclosure is not limited to any particular type of flexible supply (or combination thereof) that may be provided inside KJL 200.

Figure 39:
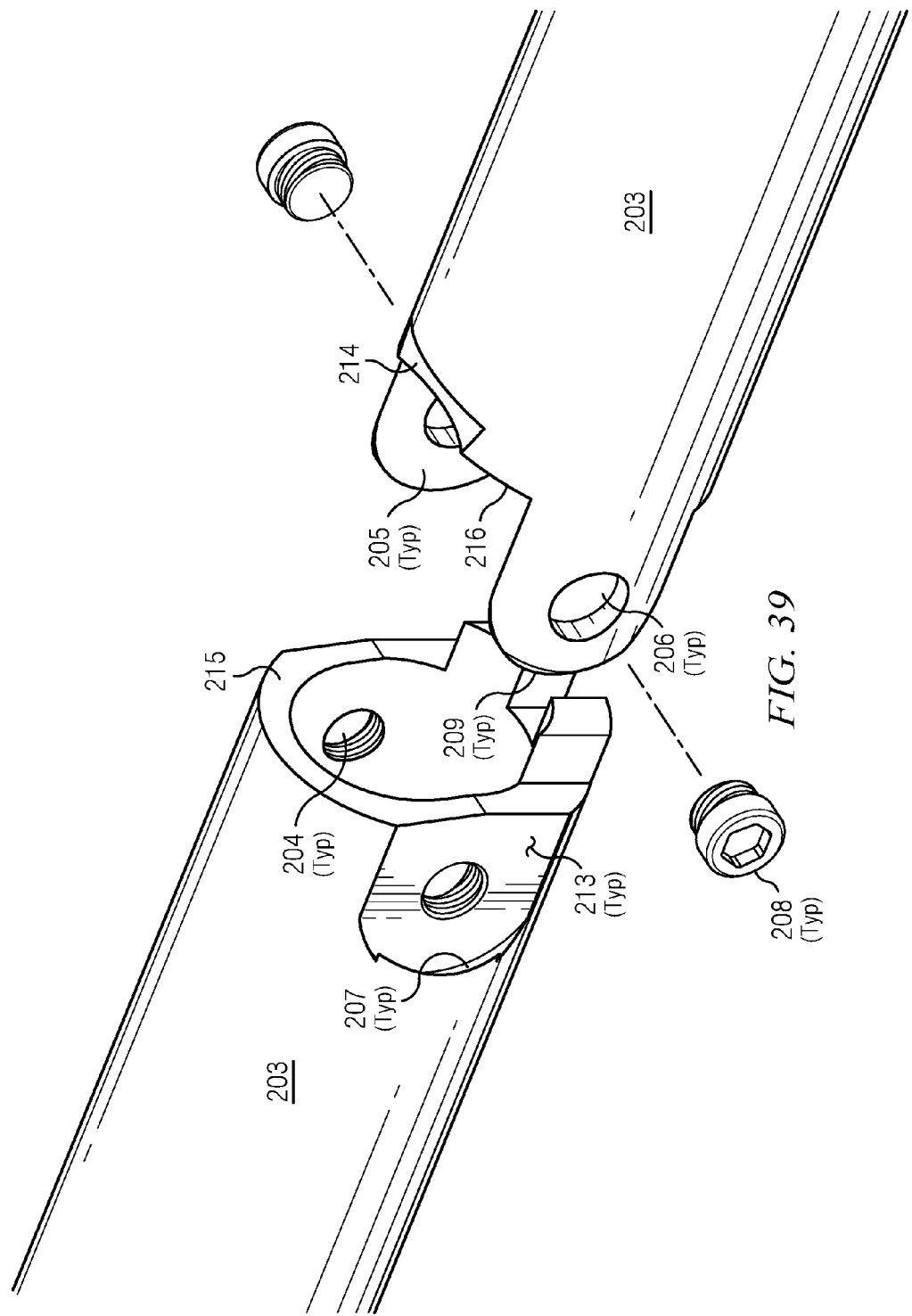
FIG. 39 is an exploded isometric view of the pinned connection between neighboring KJL segments 203 shown assembled on FIG. 29.
Figure 41:
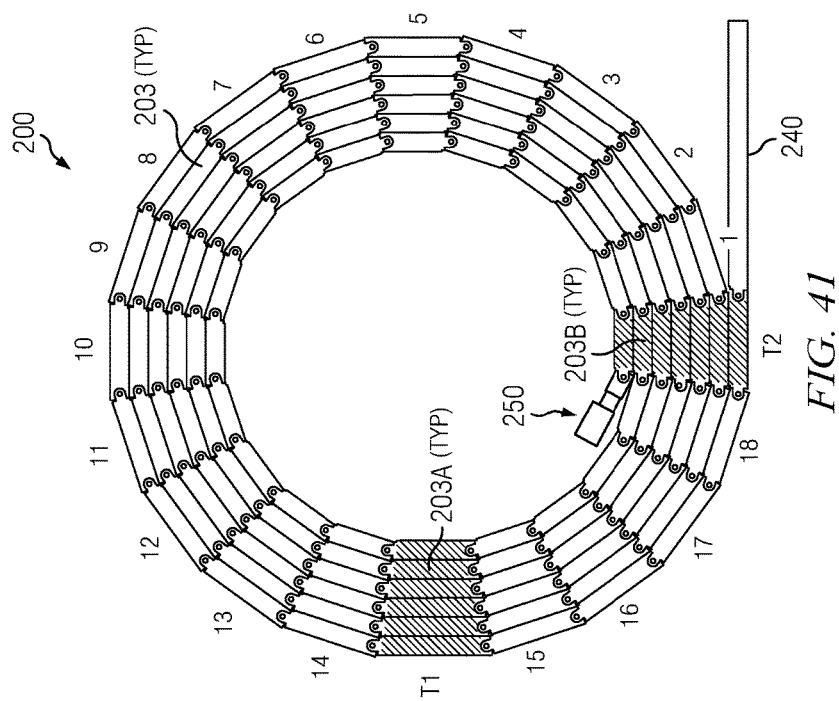
FIG. 41 depicts KJL 200 from FIG. 40 in isolation.
Figure 40:
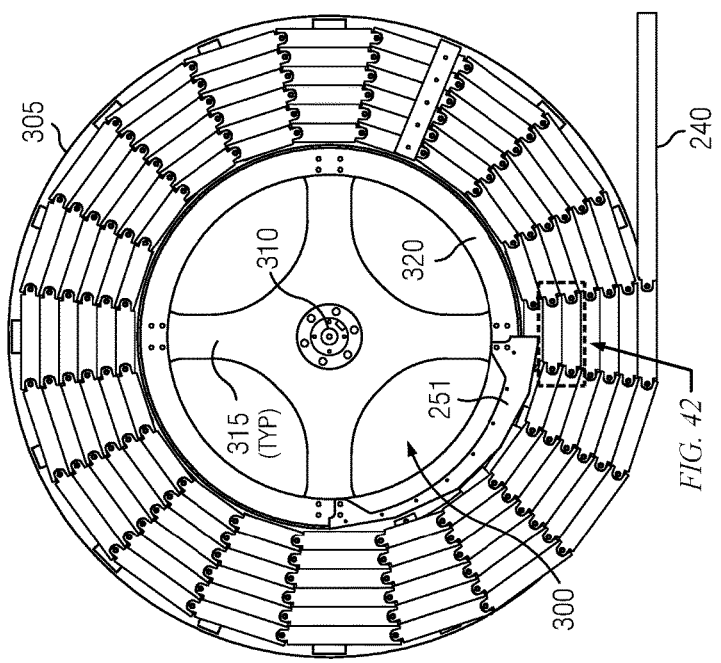
FIG. 40 illustrates one embodiment of alternative embodiment 200 spooled onto reel 300, which may be, for example, an alternative embodiment of SLR 190$_S$ (shown more, generally on FIG. 23)
Figure 42:
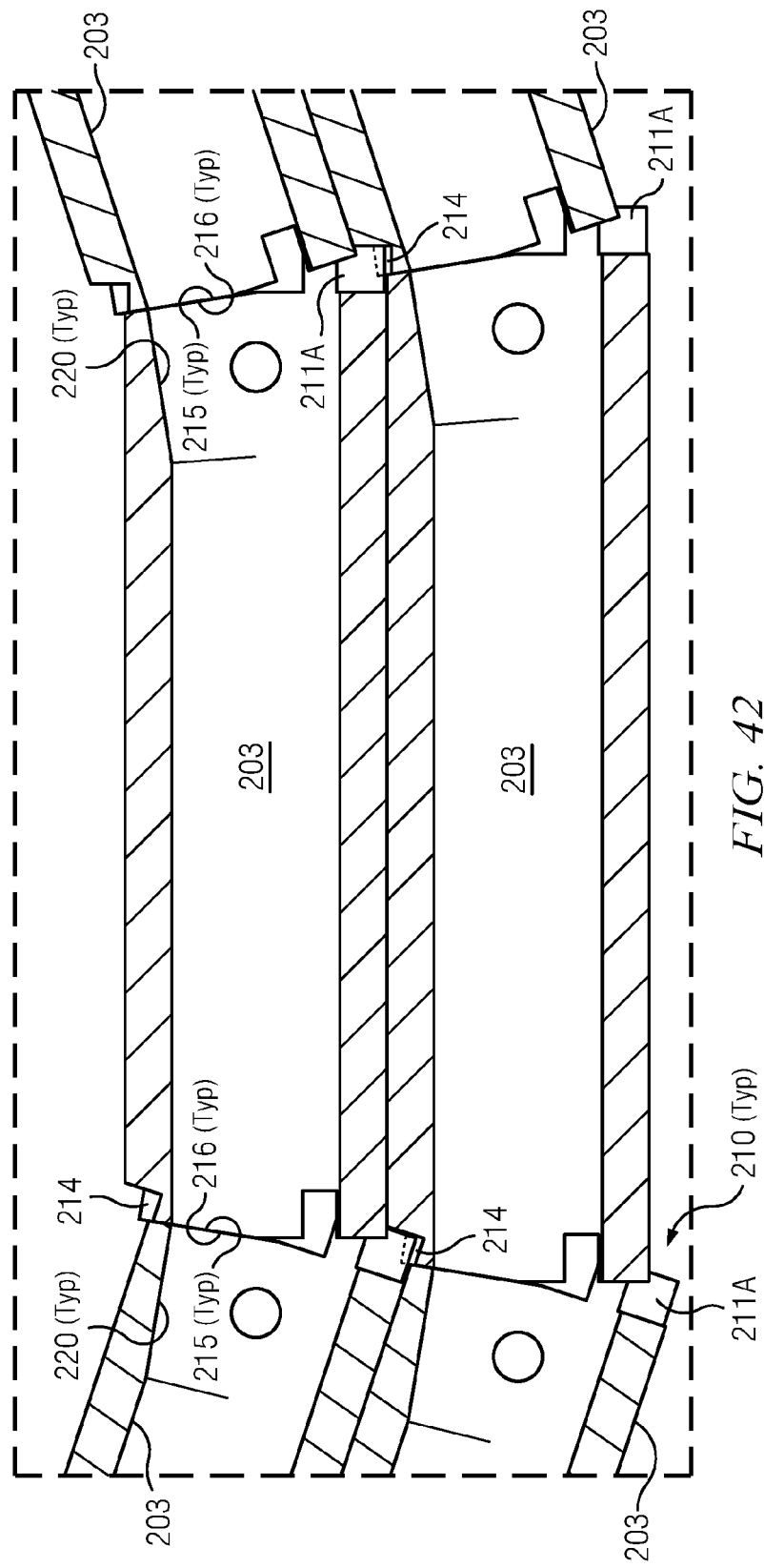
FIG. 42 is a vertical section as shown on FIG. 40.

Referring first to FIGS. 40 through 42, it will be seen that KJL 200 is a concatenated string of KJL segments 203. Physical parameters of the KJL segments 203, including (without limitation) their lengths and respective positions in KJL 200, are preselected so as to allow KJL 200 to be nested onto reel 300. Features and aspects of KJL 200's nesting capability onto reel 300 will be described in greater detail below. In some KJL deployments, reel 300 may be an alternative embodiment of SLR 190$_S$, as shown and described in detail above with reference to FIG. 23. FIGS. 29 through 39 depict one exemplary neighboring pair of KJL segments 203 within KJL 200. The neighboring pair of KJL segments illustrated on FIGS. 20 through 39 is used in this disclosure as an example to illustrate features and aspects generally relating to the pinned connection by which KJL segments 203 are conjoined substantially throughout KJL 200.

The description below associated with FIGS. 29 through 43 further adopts a labeling convention throughout, for ease of reference and understanding. Each KJL segment 203 has a "first end" and a "second end", specifically identified as such on FIG. 29. Referring momentarily to FIGS. 40 and 41, the first end of each KJL segment 203 is defined as a "leading end", such that the first end, is oriented towards the direction in which the KJL 200 is extended when KJL 200 is spooled off the reel 300 (i.e., the end to which KJL stinger 240 is attached on FIGS. 40 and 41). By contrast, the second end of each KJL segment 203 is defined as a "trailing end", such that the second end is oriented away from the direction in which KJL 200 is extended when KJL 200 is spooled off the reel 300 (i.e. the end to which KJL hub adapter 250 is attached on FIGS. 40 and 41). FIG. 29 shows that for each neighboring pair of KJL segments 203, the first end of one KJL segment 203 is joined to the second end of the other KJL segment 203 at the pinned connection conjoining the neighboring KJL segment pair.

FIGS. 29, 30 and 39 illustrate aspects of the pinned connection between neighboring KJL segments 203 in detail. FIG. 30 is a section as shown on FIG. 29. FIG. 39 is an exploded isometric view of the pinned connection between neighboring KJL segments 203 shown assembled on FIG. 29. Referring first to FIG. 29, the second end of KJL segment 203 provides opposing ears 205. Each ear 205 provides an ear hole 206, such that ear holes 206 are also preferably opposing. Each ear 205 also provides an ear ledge 209 at a distal end thereof. FIG. 29 also shows that the first end of KJL segment 203 provides opposing ear cutouts 213. Each ear cutout 213 provides a trunnion hole 204, such that trunnion holes 204 are also preferably opposing. Each ear cutout 213 also provides an ear ledge recess 207. Ear ledge recesses 207 are shaped and configured for receiving ear ledges 209 on ears 205. The interoperation of ear ledge recesses 207 and ear ledges 209 will be described in greater detail below with reference to other Figures.

FIGS. 29, 30 and 39 illustrate that trunnions 208 secure a pinned connection between neighboring KJL segments 203, through insertion of trunnions 208 through ear holes 206 and fixation into trunnion holes 204. Ears 205 on the second end of one KJL segment 203 are received over corresponding ear cutouts 213 on the first end of the neighboring KJL segment, such that ear holes 206 and trunnion holes 204 are collocated. Trunnions 208 (one for each collocated ear hole 206 and trunnion hole 204) are inserted through ear holes 206 and, preferably, are fixed into trunnion holes 204 by a threaded connection. FIG. 30 illustrates this assembly. Preferred embodiments of trunnions 208 provide a conventional hex recess for tightening (or removal) with an Allen wrench. As further shown on FIGS. 29, 37 and 39, the hex recess is provided in an outer dome whose diameter fits into ear holes 206. The dome's curvature is preferably selected to approximate the curvature of the surrounding ears 205, and to minimize protrusion of the dome beyond the curvature of the surrounding ears 205. Contact surfaces between the domes on trunnion 208 and ear holes 206 are preferably smooth, with an operational fit that promotes free rotation of the pinned connection while at the same time minimizing friction and "slop". The threaded shank portion of trunnions 208 preferably is of a length such that the threaded connection between trunnions 208 and trunnion holes 204 becomes tight before a trunnion 208 protrudes through the inside wall of a KJL segment 203.

Figure 38A:
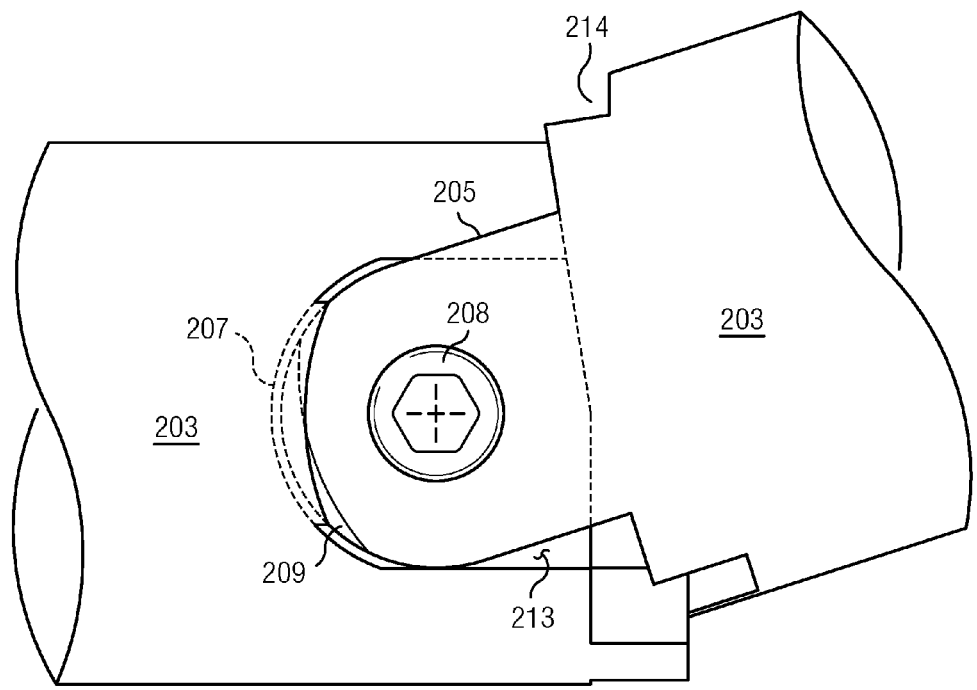
FIGS. 38A and 38B are enlargements as shown on FIGS. 31A and 31B.
Figure 38B:
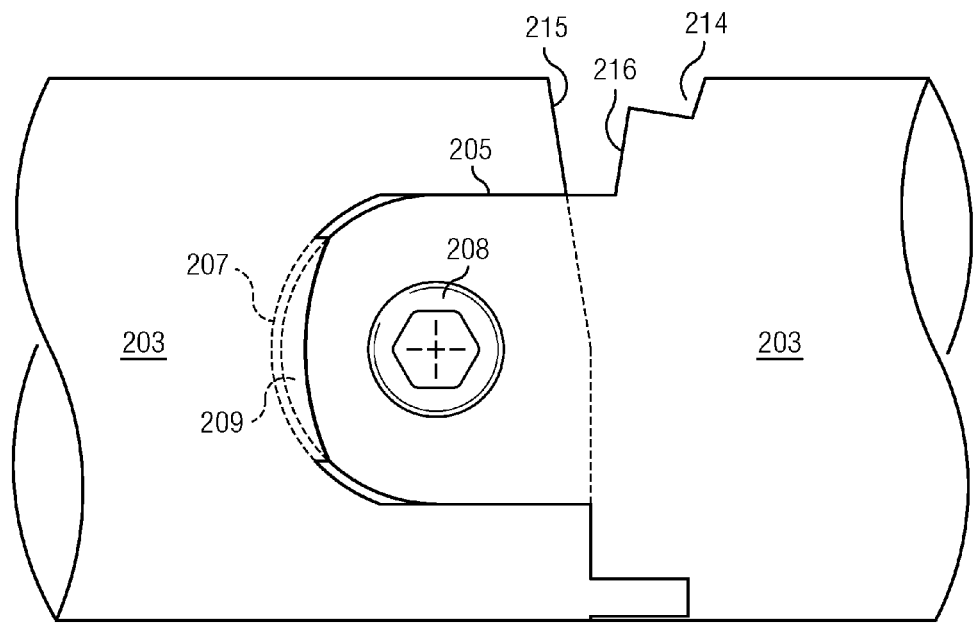

FIGS. 31A, 31B, 37, 38A, 38B and 39 all illustrate aspects of the interoperation of ear ledges 209 (on ears 205) as received into ear ledge recesses 207 (on ear cutouts 213) between neighboring KJL segments 203. FIG. 37 is a section as shown on FIG. 36. FIG. 39 is an exploded isometric view of the pinned connection between neighboring KJL segments 203, including ear ledges 209 disassembled from ear ledge recesses 207. FIGS. 38A and 38B are enlargements as shown on FIGS. 31A and 31B. As shown on FIGS. 37, 38A and 38B, for example, each ear ledge 209 is configured to be slidably retained within a corresponding ear ledge recess 207 when trunnion 208 enables the pinned connection between neighboring KJL segments 203. Each ear ledge recess 207 is configured and shaped to slidably receive a corresponding ear ledge 209 when trunnions 208 are received through ear holes 206 and fixed into the trunnion holes 204. Ear ledges 209 and ear ledge recesses 207 cooperate to restrain displacement of ears 206 with respect to ear cutouts 213 except for relative rotation between ears 206 and ear cutouts 213 about the pinned connection. FIGS. 37, 38A and 38B depict ear ledge 209 as preferably an angular chamfer or bevel along the outer edge of approximately one half of the distal end tip of ear 205. Ear ledge recess 207 is shaped to receive a corresponding ear ledge 209, and to constantly retain ear ledge 209 within ear ledge recess 207 notwithstanding any permitted rotation of neighboring KJL segments 203 about their pinned connection. FIG. 37 shows that while the interoperation of ear ledge 209 within ear ledge recess 207 is a slidable retention, the depth of ear ledge recess 207 is selected such that ear ledge 209 preferably does not make contact with the deepest portions of ear ledge recess 207 during rotation of the pinned connection, or even when the pinned connection is placed under expected operational compression loads.

FIGS. 34, 35 and 37 depict toothed connection 210. Generally, and with reference to FIGS. 34 and 35, toothed connection 210 is an interlocking enmeshment of teeth activated by rotation of neighboring KJL segments 203 about the pinned connection. Referring generally to FIGS. 34 and 35, toothed connection 210 includes first teeth 211A and a second tooth recess 212B on the first end of one neighboring KJL segment 203, and second tooth 212A and first tooth recesses 211B on the second end of the other neighboring KJL segment 203. Enmeshment of first teeth 211A in first tooth recesses 211B, and second tooth 212A in second tooth recess 212B, forms interlocking toothed connection 210. Preferably teeth 211A, 212A and tooth recesses 211B, 212B are square or rectangular in shape, although the scope of this disclosure is not limited in this regard. Similarly the scope of this disclosure is not limited to the number of interlocking teeth 211A, 212A and tooth recesses 211B, 212B that may be provided. FIG. 37 shows that toothed connection 210 is configured such that it is fully engaged (i.e. teeth 211A, 212A and tooth recesses 211B, 212B are in substantially full interlocking enmeshment) when neighboring KJL segments 203 are in straight line alignment ("straight mode") about the pinned connection. FIGS. 34 and 35 illustrate that, in preferred embodiments, teeth 211A, 212A are long enough for toothed connection 210 to remain partially engaged (i.e. teeth 211A, 212A are partially interlocked in tooth recesses 211B, 212B) when neighboring KJL segments 203 are in full angular displacement ("curved mode") about the pinned connection.

FIGS. 29, 31B, 33 and 36 illustrate that KJL segments 203 have a partially-trapezoidal shape/profile when viewed in a direction along or parallel to the axis of rotation of neighboring KJL segments 203 about the pinned connection provided by trunnions 208. FIG. 33 also depicts this partially-trapezoidal shape/profile of neighboring KJL segments 203 in more detail. First sloped surface 215 at first end of KJL segment 203 and second sloped surface 216 at second end of KJL segment 203 combine to create a partially-trapezoidal shape/profile of neighboring KJL segments 203. It will be understood that this partially-trapezoidal shape/profile enables limited incremental radial deflection at each pinned connection. FIG. 33 further shows that first sloped portion 215 provides a first angular displacement 217 at the first end of KJL segment 203, and second sloped portion 216 provides a second angular displacement 218 at the second end of KJL segment 203. When first and second sloped portions 215, 216 oppose each other at a pinned connection, between neighboring KJL segments 203 (as shown on FIG. 33), first and second angular displacements 217, 218 form a combined angular displacement 219. Referring now to FIGS. 40 and 41 in addition to FIG. 33, it will be appreciated that combined angular displacement 219 allows a predesigned and limited incremental radial deflection at each pinned connection in KJL 200. Such incremental radial deflection is limited by contact between first and second sloped portions 215, 216 on neighboring KJL segments 203, as illustrated on FIG. 42. Such limited incremental deflection at each pinned connection between neighboring KJL segments 203 in turn allows KJL 200, overall, to spool onto reel 300 in nested fashion at a predesigned radius of curvature. It will be further understood that first and second sloped portions 215, 216 (and therefore first and second angular displacements 217, 218 leading to combined angular displacement 219) may be selected according to user design for different embodiments of KJL 200.

FIGS. 40 and 41 illustrate the nesting aspect of preferred embodiments of KJL 200 described in this disclosure. On FIGS. 40 and 41, KJL 200 comprises a concatenated string of KJL segments 203, each neighboring pair of KJL segments 203 rotatably connected via a pinned connection. Features and aspects of the pinned connection are described elsewhere in this disclosure with reference to FIGS. 29 through 39. KJL 200 on FIG. 40 is spooled onto reel 300. FIG. 41 illustrates KJL 200 as spooled onto reel 300, per FIG. 40, except with reel 300 omitted for clarity. Reel 300 on FIG. 40 may be conventional, including rim 305, axle 310, spokes 315 and hub 320.

Figure 43:
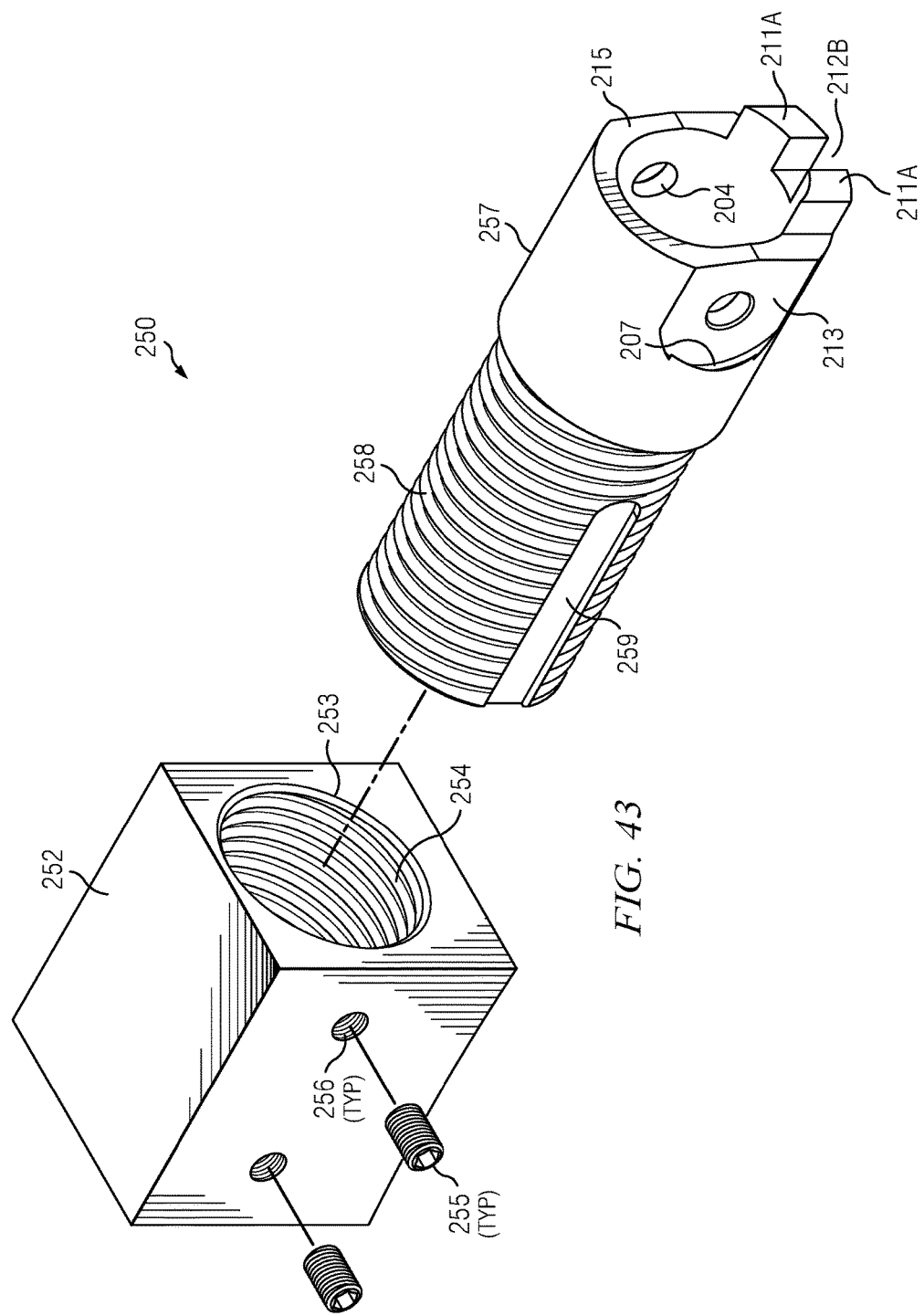
FIG. 43 is an exploded isometric view of KJL hub adapter 250 as shown assembled on FIG. 41.

FIGS. 40 and 41 illustrate that KJL 200 is configured at one end to attach to hub 320 via KJL hub adapter 250 (KJL hub adapter 250 is hidden from view on FIG. 40 by KJL hub adapter cover 251), and at the other end to KJL stinger 240 via a pinned connection. FIG. 43 illustrates features and aspects of KJL hub adapter 250 in more detail, and is described in more detail further below in this disclosure. KJL stinger 240 is preferably similar in design and function to stinger 104 as illustrated and described above with reference to FIG. 1, for example.

Referring again to FIGS. 40 and 41, KJL 200 is shown configured to spool around hub 320 in nested fashion all the way out to rim 305. Generally stated with reference to FIGS. 40 and 41, responsive to user assignment of a predetermined length to each KJL segment 203 according to the KJL segment 203's corresponding pre-ordained position in KJL 200, KJL 200 is disposed to spool onto reel 300 in nested fashion, such that for each spooling revolution made by KJL 200 onto reel 300, (a) KJL segments 203 stack in circumferential registered layers around reel 300 and (b) pinned connections trace substantially radial vectors from the center of the reel 300. FIGS. 40 and 41 show that successive layers of KJL segments 203 stack compactly in register onto hub 320 as KJL 200 spools multiple times around reel 300. It will be seen on FIGS. 40 and 41 that when properly nested, the pinned connections in successive layers of KJL segments 203 on reel 300 trace generally radial pathways between hub 320 and rim 305. To enable such nesting, the lengths of individual KJL segments 203 are preselected according a pre-ordained position for each KJL segment 203 in the concatenated string of KJL segments 203 that forms KJL 200. As seen on FIGS. 40 and 41, the lengths of KJL segments 203 that stack closer to rim 305 are pre-selected to be longer than the lengths of corresponding KJL segments 203 that stack closer to hub 320.

FIG. 41 further illustrates that transitional KJL segments 203A and 203B have preselected transitional lengths, and are also placed in pre-ordained positions in overall KJL 200. Transitional KJL segments 203A and 203B have preselected transitional lengths that enable one stacked layer of KJL segments 203 to transition smoothly onto the next, thus allowing compact nesting of multiple stacked layers.

Example 1 now follows, setting forth preselected lengths of KJL segments 203 and transitional KJL segments 203A, 203B in pre-ordained positions in one exemplary KJL 200. The KJL according to Example 1 will nest generally in accordance with FIGS. 40 and 41. In Example 1, KJL 200 has a nominal length of 75 feet. Before discussing Example 1 in detail however, it must be emphasized that Example 1 is just one example of many configurations of KJL segments within the scope of this disclosure that may be user-designed and then concatenated into a customized KJL. Variables such as KJL segment length, number of transition length segments and location thereof in a concatenated string, KJL segment diameter, KJL segment thickness, overall desired KJL length, diameter of reel, and desired amount of angular displacement between neighboring KJL segments, just for example, are all parameters that may go into a user design of a configuration of KJL segments that will nest on a reel generally in accordance with the principle illustrated on FIGS. 40 and 41. All such designs of KJL segment configurations that will nest on a reel generally in accordance with the principle illustrated on FIGS. 40 and 41 are considered to be within the scope of this disclosure.

Turning now to Example 1 and with reference to FIG. 41, it will be seen from FIG. 41 that KJL 200 provides eighteen numbered sectors (1-18) of stacked KJL segments 203 in nested layers. FIG. 41 also shows that KJL segments 203 in a particular layer position in one numbered sector have the same length as KJL segments 203 in the same layer position in the other numbered sectors. This design promotes ease and economy of KJL segment manufacturing by increasing the number of KJL segments 203 that share a common length. FIG. 41 also shows transitional sector T1 providing stacked layers of transitional KJL segments 203A, and transitional sector T2 providing stacked layers of transitional KJL segments 203B. Transitional KJL segments 203A, 203B are of different user-selected lengths than KJL segments 203 nested in their corresponding sectors 1-18, but are otherwise are the same overall design. Transitional KJL segments 203A, 203B, at their pre-ordained position in the overall KJL 200, allow for make-up and adjustment of length for each stacked layer in order to provide compact nesting around the circumference of reel 300.

In Example 1, KJL segments 203 are 1.75" nominal OD, and 1.125" nominal ID. The length of KJL 200 is nominally 75 feet, and hub 320 on FIG. 40 is nominally 35.5 inches in outside diameter. The table below shows segment lengths according to Example 1, including for KJL stinger 240 on FIGS. 40 and 41, and for KJL segment adapter 257 on FIG. 43.

EXAMPLE 1

Segment Lengths as Illustrated on FIGS. 40 and 41 for 75 Foot (Nominal) Lance (Segment Lengths in Inches)

| KJL segment adapter (Item 257 on FIG. 43) | Uniform length segments in sectors 1 thru 18 | Transition segment layers T1 | Transition segment layers T2 | KJL stinger (Item 240 on FIGS. 40 and 41) |
|---|---|---|---|---|
| 4.925 | 5.979 | 7.729 | 5.702 | |
| | 6.533 | 8.283 | 6.256 | |
| | 7.088 | 8.838 | 6.811 | |
| | 7.642 | 9.392 | 7.365 | |
| | 8.196 | 9.946 | 7.919 | |
| | 8.751 | 10.501 | 8.474 | |
| | | | 9.028 | 60.000 |

Previously-described nesting embodiments of KJL 200, including with reference to FIGS. 40, 41 and Example 1, have focused on nesting embodiments that stack one layer of KJL segments 203 at a time on top of one another on reel 300. The scope of this disclosure is not limited in this regard, however. Other embodiments (not illustrated) may provide reel hub 320 wide enough to accommodate more than one revolution of spooled KJL segments 203 onto reel hub 320 in each layer. Thus, as KJL 200 spools onto reel 300, KJL segments 203 make two or more revolutions of reel 300 side-by-side in each layer before beginning the next layer on top of the immediately previous layer. Alternatively stated KJL 200 makes at least two spooling revolutions onto the reel 300 before KJL segments 203 increment a further stacked circumferential registered layer thereof. In such "multi-revolution layer" embodiments, KJL design would be analogous to the illustrated "single-revolution layer" embodiments described above, in that the lengths of KJL segments 203 would still have to be calculated and selected for their individual pre-ordained positions in overall KJL 200. The lengths and locations of transitional KJL segments would also still have to be calculated and ordained. However, the KJL design would have to account for multiple reel revolutions for each layer, as well as for multiple layers.

"Multi-revolution layer" embodiments of KJL 200 (as described in above) provide spooling compactness advantages generally, and in particular for applications in which KJL 200 must be unusually long. With two or more revolutions per stacked layer, a longer KJL may be spooled onto a reel of physically manageable size and diameter. Further, in a "single-revolution layer" deployment on a reel, an unusually long KJL may cause the outer nested layers on the reel to require unusually long KJL segments. Such long KJL segments may be more difficult or expensive to make, or may provide a limited radius of curvature for the overall KJL in the application in which the long KJL is being used. In contrast, a "multi-revolution layer" deployment on a reel allows KJL segments on the outer nested layers on the reel to remain comparatively short.

FIG. 42 a vertical section as shown on FIG. 40, and illustrates the spooling notch feature provided by embodiments of KJL 200. The spooling notch assists KJL segment nesting on reel 300 (as seen on FIG. 40) when neighboring KJL segments 203 are in curved mode.

Reference is made to FIGS. 34 and 35 in order to assist understanding of the spooling notch feature illustrated on FIG. 42. FIG. 34 is an isometric view of FIG. 29 from underneath, and depicts the pinned connection between neighboring KJL segments 203 when in curved mode. FIG. 35 is an enlargement as shown on FIG. 34. FIG. 35 shows that toothed connection 210 separates when KJL segments 203 are in curved mode, causing first teeth 211A to protrude out. Referring momentarily to FIGS. 40 and 41 in addition to FIG. 35, it will be appreciated that such protrusion of first teeth 211A when KJL 200 is in curved mode may cause interference with compact nesting of layers of KJL segments 203.

FIG. 29 (and other Figures) depict spooling notch 214 provided on the second end of KJL segments 203 at a location opposite second tooth 212A and first tooth recesses 211B. FIG. 42 shows that when KJL segments 203 are nested, spooling notches 214 on one stacked layer coincide with and receive protruding first teeth 211A on the next innermost stacked layer. As a result, neighboring layers of KJL segments 203 are able to nest compactly, free from interference caused by protruding first teeth 211A on one layer adversely contacting KJL segments 203 on the next outermost layer.

FIG. 43 is an exploded isometric view of KJL hub adapter 250 as shown assembled on FIG. 41. FIGS. 40 and 41 depict KJL hub adapter 250 provided on reel hub 320, although reel hub 320 is obscured from view on FIG. 40 by KJL hub adapter cover 251. KJL hub adapter 250 selves as the anchor point for KJL 200 onto reel hub 320. Referring to FIG. 43, KJL hub adapter 250 includes KJL adapter block 252 and KJL segment adapter 257. KJL adapter block 252 is configured for rigid attachment to reel hub 320. Such rigid attachment is conventional and not illustrated, and may include rigid attachment by welding or fasteners, for example. KJL adapter block 252 provides KJL adapter block receptacle 253, into which KJL segment adapter 257 is received by threaded engagement between KJL adapter block threads 254 and KJL segment adapter threads 258. KJL segment adapter 257 further provides a complete "first end" of a KJL segment 203 as illustrated on FIG. 29, including ear cutouts 213, trunnion holes 204, ear ledge recesses 207, first sloped portion 215, first teeth 211A and second tooth recess 912B. In this way, a second end of any KJL segment 203 may form a pinned connection and interoperate with KJL segment adapter 257 in the same way as other pinned connections are formed between neighboring KJL segments 203 elsewhere on KJL 200.

With further reference to FIG. 43, it will be understood that fine positional adjustment of KJL segment adapter 257 relative to KJL adapter block 252 may be made by rotating KJL segment adapter 257 into and out of KJL adapter block 252 on KJL adapter block threads 254 and KJL segment adapter threads 258. Once a desired position is selected for KJL segment adapter 257, set screws 255 are inserted through set screw holes 256 and are tightened down on set screw slot 259, thereby locking KJL segment adapter 257 in its selected position.

Earlier description in this disclosure highlighted that hoses, cables or other types of flexible supply products carried inside KJL 200 may be high-specification products provided for high-end performance or extended service life, for example. The unit cost of such high-specification supply products may be significantly higher than the corresponding cost of conventional products. It is therefore highly advantageous to protect the integrity of the supply hoses, cables and related products carried inside KJL 200 from incidental damage caused by the interior of KJL 200. Preferably, sharp bends should be minimized in the interior of KJL 200, and particularly at the pinned connections between neighboring KJL segments 203 when in curved mode. Any such sharp bends may transfer into the flexible supply products inside KJL 200, and cause bending damage. Further, sharp edges on the interior of KJL 200 may cause cuts or gouges on the hoses, cables or other flexible supply products.

FIGS. 33 and 42 show wall thickness tapers 220 provided on the interior wall of the first end of KJL segments 203, at a location opposite first teeth 211A and second tooth recess 912B. As shown on FIG. 42 when layers of KJL segments 203 are nested in curved mode, wall thickness tapers 220 smooth out the pathway of the interior wall as the wall transitions from the first end of one KJL segment 203 in a neighboring pair thereof into the second end of the other KJL segment 203. As a result, sharp bends and sharp edges inside the interior of KJL 200 are minimized. Further, the hoses, cables and other flexible supply products inside KJL 200 can bend more smoothly around pinned connections in neighboring KJL segments 203 when in curved mode, which in turn preferably allows such flexible supply products to stay within their individual safe minimum bend radius specifications. It will be appreciated that although illustrated and described embodiments in this disclosure show wall thickness taper 220 provided on the first end of KJL segments 203, this disclosure is not limited in this regard. Other embodiments (not illustrated) could provide wall thickness tapers on the second end of KJL segments 203, or cooperating wall thickness tapers on both first and second ends.

For the avoidance of doubt, it will be understood that throughout this disclosure, certain conventional structure has been omitted for clarity. For example, and without limitation, features of MLI assembly 100 are, in either curved or straight mode, advantageously supported by structural steel and other conventional support means, all of which has been omitted for clarity. Operation of MLI assembly 100 (including at adjustment assembly 120) is advantageously accomplished using conventional hydraulic, pneumatic or electrical apparatus, all of which has been also omitted for clarity.

Currently preferred embodiments of MLI assembly 100 may further be controlled to operate in user-selected options of manual, semi-automatic and automatic modes. A paradigm for optimal Scorpion System operating efficiency includes being able to program the MLI to run automatically. That is, to repeat a cycle of tubular interior processing operations (including cleaning and data acquisition operations) as a series of tubulars W are automatically and synchronously: (1) placed into position at the beginning of the cycle, (2) ejected at the end of the cycle, and then (3) replaced to start the next cycle. In automatic mode, the user may specify the sequence of operations of KJL assemblies 103 in a cycle on each tubular W. The cycle of lance operations will then be enabled and controlled automatically, including insertion and retraction of KJL assemblies 103 in sequence in and out of the tubular W, with corresponding repositioning of guide tubes 101 and stabbing guide 102 with respect to tubular W between each lance operation. The cycle may be repeated in automatic mode, as tubulars W are sequentially placed into position. In semi-automatic mode, the operation may be less than fully automatic in some way. For example, a cycle may be user-specified to only run once, so that tubulars W may be manually replaced between cycles. In manual mode, the user may dictate each lance operation individually, and the MLI may wait for further instruction after each lance operation.

Although the present invention and its advantages have been described in detail, it should be understood that various changes, substitutions and alternations can be made herein without departing from the spirit and scope of the invention as defined by the appended claims.

I claim:

1. A Knuckle Jointed Lance (KJL), comprising:
a segmented lance, the lance including a plurality of elongate and hollow KJL segments in a concatenated string thereof, the string divided into a concatenated plurality of discrete segment groups each segment group including a plurality of KJL segments, the string having first and second string ends wherein a first bookend segment group is at the first string end and a second bookend segment group is at the second string end, wherein further:
 (A) each segment group includes a plurality of uniform-length KJL segments and at least one transitional-length KJL segment;
 (B) for each segment group, each of the at least one transitional-length KJL segments therein has a different length than the uniform-length KJL segments therein;
 (C) the uniform-length KJL segments in the first bookend segment group have a smaller uniform length than the uniform-length KJL segments in the second bookend segment group;
wherein each KJL segment has a longitudinal axis, and has first and second segment ends;
wherein, for each neighboring pair of KJL segments in the concatenated string:
 (1) the first segment end of one KJL segment in the pair is rotatably connected to the second segment end of the other KJL segment in the pair via a pinned connection such that when the pair of KJL segments is in longitudinal axis alignment, the KJL segments are restrained from relative rotation about the pinned connection except in a first rotational direction only; and
 (2) the first segment end of the one KJL segment in the pair provides a first sloped portion, the first sloped portion facing a second sloped portion provided on the second segment end of the other KJL segment in the pair, such that contact between the first and second sloped portions limits relative rotation about the pinned connection in the first rotational direction.

2. The KJL of claim 1, in which, for at least one neighboring pair of KJL segments, the first segment end on the one KJL segment and the second segment end on the other KJL segment together provide an interlocking toothed connection such that the interlocking toothed connection restrains relative torsional displacement between the at least one neighboring pair of KJL segments about the longitudinal axes of the KJL segments.

3. The KJL of claim 2, in which the interlocking toothed connection is in full interlocking enmeshment when the at least one neighboring pair of KJL segments is in longitudinal axis alignment.

4. The KJL of claim 2, in which the interlocking toothed connection is in at least partial interlocking enmeshment when the first and second portions surfaces make contact.

5. The KJL of claim 2, in which KJL segments each provide a spooling notch such that when KJL segments are stacked in concentric radial layers, spooling notches on a first radial layer each receive a corresponding interlocking toothed connection in partial interlocking enmeshment on a second radial layer, wherein the second radial layer is stacked immediately adjacent to and concentrically inside the first radial layer.

6. The KJL of claim 1, in which at least one of the pinned connections further includes:
 two opposing ears extending from the second segment end of the other KJL segment, each ear providing one ear hole, each ear further providing an ear ledge at distal end thereof;
 two opposing ear cutouts in the first segment end of the one KJL segment, each ear cutout providing one trunnion hole, each ear cutout further providing an ear ledge recess formed therein;
 a pair of trunnions, each trunnion received through a corresponding ear hole and fixed into a corresponding trunnion hole when the ears are received over the ear cutouts;
 wherein each ear ledge recess is configured and shaped to slidably receive a corresponding ear ledge when the trunnions are received through the ear holes and fixed into the trunnion holes; and
 wherein the ear ledges and ear ledge recesses cooperate to restrain displacement of the ears with respect to the ear cutouts except for relative rotation between the ears and the ear cutouts about the pinned connection.

7. The KJL of claim 6, in which the ear ledges are retained by the ear ledge recesses at all times.

8. The KJL of claim 6, in which the ear ledge recesses have a preselected depth, and in which the ear ledges are at all times received into the ear ledge recesses at depths that are less than the preselected depth.

9. The KJL of claim 1, in which, for selected neighboring pair, of KJL segments, at least of one of (a) the first segment end on the one KJL segment in each selected neighboring pair, and (b) the second segment end on the other KJL segment in each selected neighboring pair, provides a wall thickness taper.

10. The KJL of claim 5, in which at least one pinned connection further includes:
 two opposing ears extending from the second segment end of the other KJL segment, each ear providing one ear hole, each ear further providing an ear ledge at a distal end thereof;
 two opposing ear cutouts in the first segment end of the one KJL segment, each ear cutout providing one trunnion hole, each ear cutout further providing an ear ledge recess formed therein;
 a pair of trunnions, each trunnion received through a corresponding ear hole and fixed into a corresponding trunnion hole when the ears are received over the ear cutouts;
 wherein each ear ledge recess is configured and shaped to slidably receive a corresponding ear ledge when the trunnions are received through the ear holes and fixed into the trunnion holes;
 wherein the ear ledges and ear ledge recesses cooperate to restrain displacement of the ears with respect to the ear cutouts except for relative rotation between the ears and the ear cutouts about the pinned connection; and
 wherein, for selected neighboring pairs of KJL segments, at least of one of (a) the first segment end on one KJL segment in each selected neighboring pair, and (b) the second segment end on the other KJL segment in each selected neighboring pair, provides a wall thickness taper.

11. The KJL of claim 1, in which contact between the first and second sloped portions limits relative rotation of neighboring KJL segments about the pinned connection in the first rotational direction to a preselected angular KJL segment deflection.

* * * * *